US012575966B2

(12) United States Patent
Suen et al.

(10) Patent No.: US 12,575,966 B2
(45) Date of Patent: *Mar. 17, 2026

(54) SYSTEM AND METHOD FOR ULTRASOUND-ENHANCED DELIVERY OF DRUGS

(71) Applicant: Sonikure Holdings Limited, Wan Chai (HK)

(72) Inventors: Wai Leung Langston Suen, Sai Wan Ho (HK); Sin Hang Sarah Cheung, Ngau Chi Wan (HK); Jan Frederik Engels, Kowloon Bay (HK)

(73) Assignee: Sonikure Holdings Limited, Wan Chai (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/515,771

(22) Filed: Nov. 21, 2023

(65) Prior Publication Data

US 2024/0164941 A1 May 23, 2024

Related U.S. Application Data

(63) Continuation of application No. 16/194,179, filed on Nov. 16, 2018, now Pat. No. 11,857,459, which is a
(Continued)

(30) Foreign Application Priority Data

May 18, 2016 (EP) ..................................... 16170141

(51) Int. Cl.
    *A61F 9/00*       (2006.01)
    *A61M 37/00*     (2006.01)

(52) U.S. Cl.
    CPC ....... *A61F 9/0008* (2013.01); *A61M 37/0092* (2013.01); *A61F 2250/0093* (2013.01)

(58) Field of Classification Search
    CPC ............ A61F 9/0008; A61F 2250/0093; A61F 9/0017; A61M 37/0092;
(Continued)

(56) References Cited

U.S. PATENT DOCUMENTS 4,976,150 A    12/1990  Deka
5,016,615 A  *  5/1991  Driller ................... A61M 37/00
                                       604/20
(Continued)

FOREIGN PATENT DOCUMENTS

CN     203494051 U    3/2014
EP     1471848 B1    5/2006
(Continued)

OTHER PUBLICATIONS

Chen, et al. The size of blood-brain barrier opening induced by focused ultrasound is dictated by the acoustic pressure. J Cereb Blood Flow Metab. Jul. 2014;34(7):1197-1204.
(Continued)

*Primary Examiner* — Lauren P Farrar
(74) *Attorney, Agent, or Firm* — Wilson Sonsini Goodrich & Rosati

(57) ABSTRACT

A drug applicator for a system for ultrasound-enhanced delivery of at least one drug to a target site in a intraocular space, the system comprising a signal generating unit operationally connected to an ultrasound transducer, wherein the drug applicator comprises at least one space hold the drug, is made from a low ultrasound attenuation material, is configured to provide low ultrasound loss coupling of the system to the sclera, and is configured to be mechanically coupled to the system and further configured to be coupled to the ultrasound transducer with low ultrasound loss. The signal generating unit and/or the ultrasound transducer are configured to emit an ultrasound wave form in at least one
(Continued)

application cycle, the application cycle comprising at least one ultrasound emitting event with a time duration TA and a waiting period with a time duration TW.

20 Claims, 30 Drawing Sheets

Related U.S. Application Data continuation-in-part of application No. PCT/EP2017/061983, filed on May 18, 2017.

(58) Field of Classification Search
CPC .. A61M 2205/3576; A61M 2210/0612; A61M 2230/50; A61K 31/525; A61K 9/0048
See application file for complete search history.

(56) References Cited

U.S. PATENT DOCUMENTS

| | | | |
|---|---|---|---|
| 5,158,071 A | 10/1992 | Umemura et al. | |
| 5,230,334 A | 7/1993 | Klopotek | |
| 5,421,816 A | 6/1995 | Lipkovker | |
| 5,433,702 A | 7/1995 | Zelman et al. | |
| 5,460,595 A | 10/1995 | Hall et al. | |
| 5,658,892 A | 8/1997 | Flotte et al. | |
| 5,906,580 A | 5/1999 | Kline-Schoder et al. | |
| 6,173,202 B1 | 1/2001 | Eppstein | |
| 6,579,519 B2 | 6/2003 | Maitra et al. | |
| 6,837,855 B1 | 1/2005 | Puech | |
| 7,033,598 B2 | 4/2006 | Lerner | |
| 7,497,119 B2 | 3/2009 | Brooks et al. | |
| 7,699,780 B2 | 4/2010 | Vitek et al. | |
| 7,785,578 B2 | 8/2010 | Miller et al. | |
| 7,972,286 B2 | 7/2011 | Prausnitz et al. | |
| 8,231,564 B2 | 7/2012 | Kadziauskas et al. | |
| 8,652,073 B2 | 2/2014 | Romano et al. | |
| 8,697,109 B2 | 4/2014 | Garner et al. | |
| 8,721,572 B1 | 5/2014 | Linder et al. | |
| 8,852,138 B2 | 10/2014 | Kadzlauskas et al. | |
| 8,867,314 B2 | 10/2014 | Murakami | |
| 8,905,949 B2 | 12/2014 | Romano et al. | |
| 8,951,547 B2 | 2/2015 | Whitmore | |
| 9,028,860 B2 | 5/2015 | Shalaby et al. | |
| 9,067,060 B2 | 6/2015 | Neev | |
| 9,125,722 B2 | 9/2015 | Schwartz | |
| 9,259,597 B2 | 2/2016 | Romano et al. | |
| 9,308,126 B2 | 4/2016 | Kahook et al. | |
| 9,314,421 B2 | 4/2016 | Chau et al. | |
| 9,352,171 B2 | 5/2016 | Gertner | |
| 9,403,039 B2 | 8/2016 | Romano et al. | |
| 9,517,359 B2 | 12/2016 | Romano et al. | |
| 9,572,711 B2 | 2/2017 | Raney et al. | |
| 11,857,459 B2 | 1/2024 | Suen et al. | |
| 2002/0138037 A1 | 9/2002 | Weimann | |
| 2003/0229331 A1* | 12/2003 | Brisken | A61M 37/0092 |
| | | | 600/459 |
| 2008/0177220 A1 | 7/2008 | Lindgren et al. | |
| 2010/0143241 A1 | 6/2010 | Johnson et al. | |
| 2010/0226971 A1* | 9/2010 | Chau | A61K 9/0009 |
| | | | 424/130.1 |
| 2011/0301469 A1 | 12/2011 | Romano et al. | |
| 2012/0109045 A1 | 5/2012 | Wrenn et al. | |
| 2012/0215160 A1 | 8/2012 | Valenti et al. | |

| | | | |
|---|---|---|---|
| 2013/0046179 A1 | 2/2013 | Humayun | |
| 2013/0211395 A1 | 8/2013 | Schwartz | |
| 2013/0245545 A1 | 9/2013 | Arnold et al. | |
| 2014/0276247 A1 | 9/2014 | Hall et al. | |
| 2015/0018752 A1 | 1/2015 | Unger et al. | |
| 2015/0148711 A1* | 5/2015 | Bujak | A61F 9/007 |
| | | | 601/2 |
| 2015/0174387 A1 | 6/2015 | McInnes et al. | |
| 2015/0174388 A1 | 6/2015 | Slayton | |
| 2015/0276685 A1* | 10/2015 | Yasuhara | G01N 29/24 |
| | | | 73/632 |
| 2015/0374540 A1 | 12/2015 | Lopath et al. | |
| 2017/0043149 A1 | 2/2017 | Liu et al. | |
| 2018/0280735 A1* | 10/2018 | Khuri-Yakub | A61N 7/02 |

FOREIGN PATENT DOCUMENTS

| | | |
|---|---|---|
| EP | 2092916 A1 | 8/2009 |
| EP | 2257251 B1 | 7/2013 |
| EP | 1983949 B1 | 8/2013 |
| EP | 2601918 B1 | 6/2014 |
| EP | 2693998 B1 | 3/2017 |
| EP | 3245988 A1 | 11/2017 |
| JP | 2002501796 A | 1/2002 |
| JP | 2009539508 A | 11/2009 |
| JP | 3158398 U | 4/2010 |
| JP | 2013518672 A | 5/2013 |
| JP | 2014503317 A | 2/2014 |
| SU | 591186 A1 | 2/1978 |
| WO | WO-2000048518 A1 | 8/2000 |
| WO | WO-2007143796 A1 | 12/2007 |
| WO | WO-2011020097 A2 | 2/2011 |
| WO | WO-2011138783 A1 | 11/2011 |
| WO | WO-2013126799 A1 | 8/2013 |
| WO | WO-2014008405 A2 | 1/2014 |
| WO | WO-2014137835 A1 | 9/2014 |
| WO | WO-2014144923 A1 | 9/2014 |
| WO | WO-2014146125 A1 | 9/2014 |
| WO | WO-2014179840 A1 | 11/2014 |
| WO | WO-2015026787 A2 | 2/2015 |
| WO | WO-2016123079 A1 | 8/2016 |
| WO | WO-2017198773 A2 | 11/2017 |

OTHER PUBLICATIONS

European partial international search report and provisional opinion dated Oct. 2, 2017 for EP Application No. 17729392.5.

European search report and opinion dated Nov. 24, 2016 for EP Application No. 16170141.2.

International search report with written opinion dated Nov. 27, 2017 for PCT/EP2017/061983.

AU Serial No. 2023203148 Examination Report dated Aug. 27, 2025.

PCT/EP2017/061983 International Preliminary Report on Patentability dated Nov. 20, 2018.

Notice of Allowance dated Aug. 22, 2023 for U.S. Appl. No. 16/194,179.

Office action dated Feb. 2, 2022 for U.S. Appl. No. 16/194,179.

Office action dated Mar. 30, 2023 for U.S. Appl. No. 16/194,179.

Office action dated Jun. 15, 2022 for U.S. Appl. No. 16/194,179.

Office action dated Oct. 6, 2022 for U.S. Appl. No. 16/194,179.

U.S. Appl. No. 16/194,179 Notice of Allowance dated Sep. 20, 2023.

U.S. Appl. No. 19/357,014 Office Action dated Jan. 2, 2026.

* cited by examiner

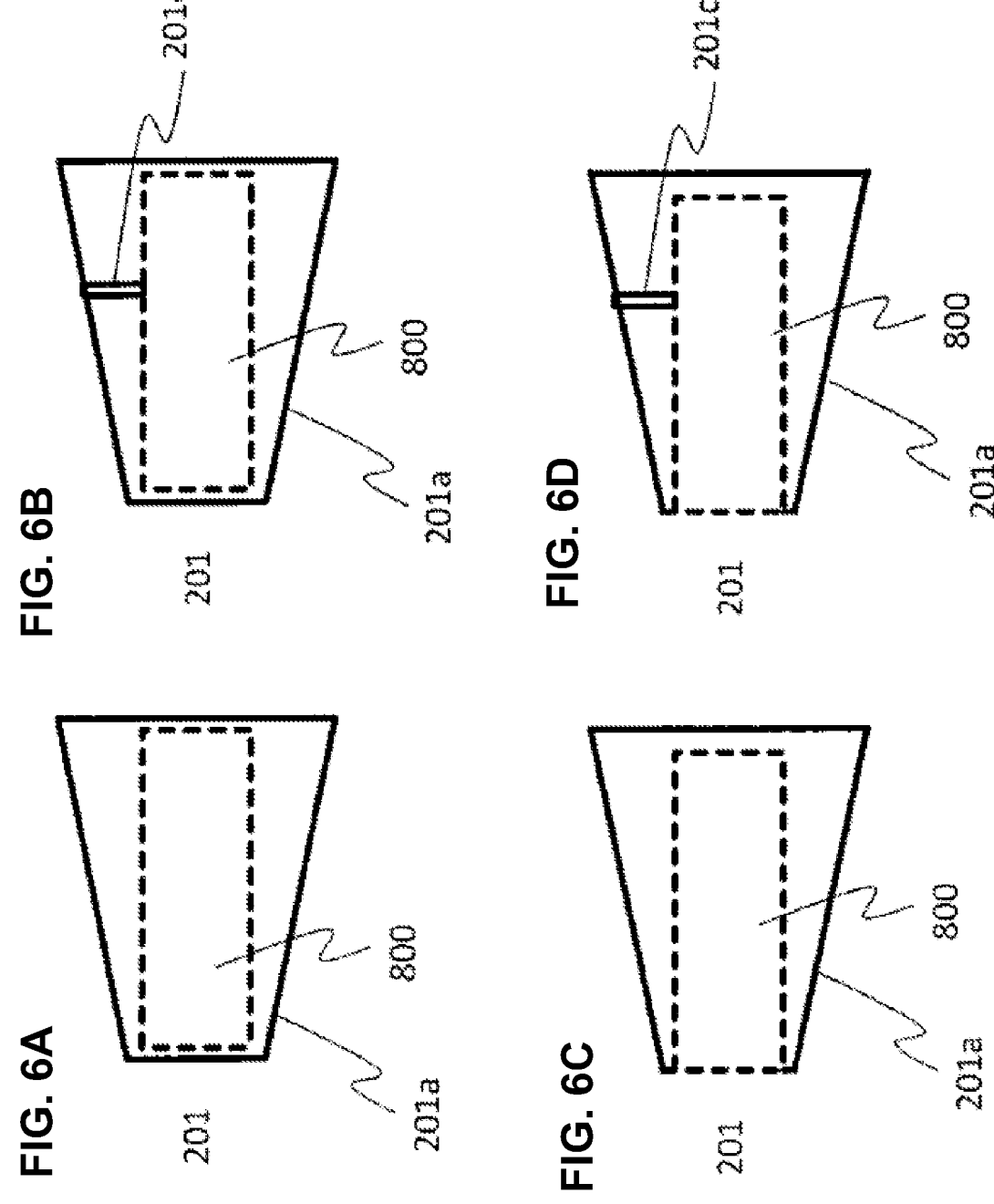

| Conditions | Static Cavitation | | | Transient Cavitation | |
|---|---|---|---|---|---|
| Peptide Mechanical Index | MI = 0.03 | MI = 0.06 | MI = 0.136 | MI = 0.38* | MI = 0.8* |
| Clusterin RNA Purification Units (a.u. ctrl) | 1.21 ± 0.97 | 1.71 ± 0.72 | 1.41 ± 0.81 | 2.06 ± 0.94 | 3.52 ± 0.72 |

FIG. 23

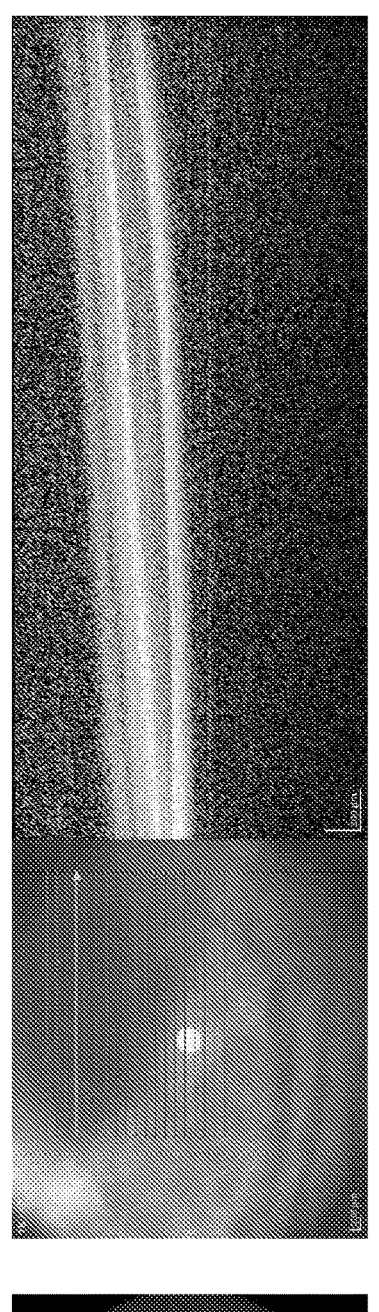
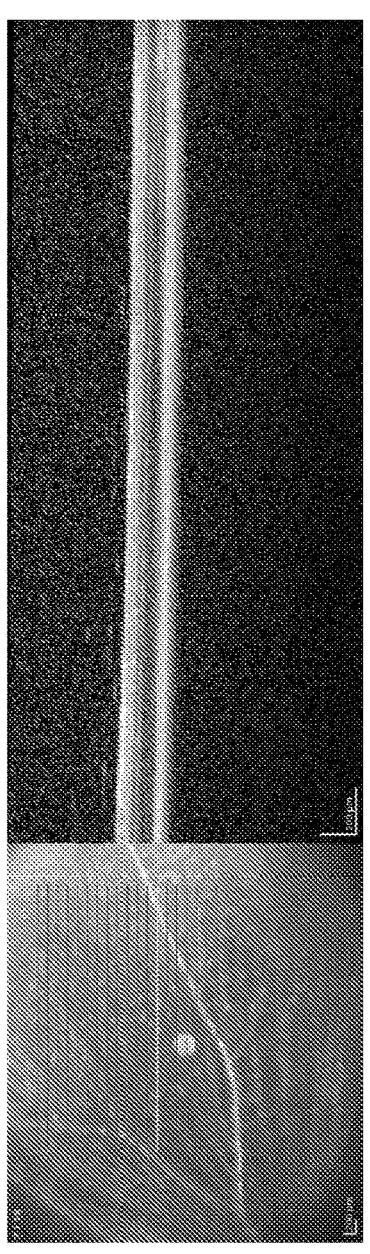
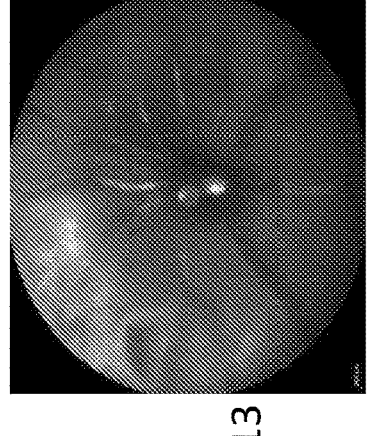
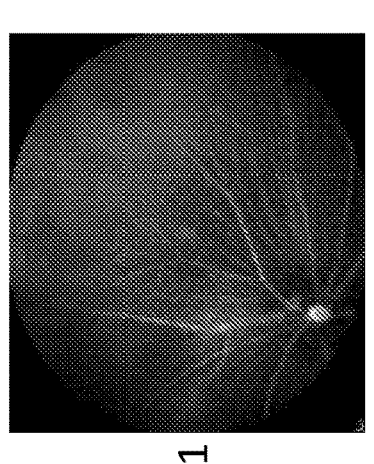
d13
d21
FIG. 30

SYSTEM AND METHOD FOR ULTRASOUND-ENHANCED DELIVERY OF DRUGS

CROSS-REFERENCE

This application is a Continuation of U.S. Application Ser. No. 16/194,179, filed Nov. 16, 2018, which is a Continuation-In-Part of International Appln. Ser. No. PCT/EP2017/061983, filed May 18, 2017, which claims the benefit of European Application Serial No. 16 17 0141.2, filed May 18, 2016, which are incorporated herein by reference in their entirety and to which applications we claim priority.

BACKGROUND OF THE INVENTION

The transscleral delivery of drugs is an important aspect of ophthalmic care. For the treatment of many diseases and/or conditions such as central retinal vein occlusion (CRVO), branch retinal vein occlusion (BRVO), central serous retinopathy, cytomegalovirus retinitis (CMV retinitis), retinoblastoma, intraocular lymphoma, ocular melanoma, giant cell arteritis (GCA), histoplasmosis, ischemic optic neuropathy (ION), macular pucker, macular telangiectasia, uveitis, choroidal neovascularization, age-related macular degeneration, diabetic retinopathy, glaucoma, retinitis pigmentosa, macular edema, macular degeneration, multirecurrent pterygia, ocular toxoplasmosis, proliferative vitreoretinopathy (PVR), Stevens-Johnson syndrome (SJS), ocular cicatricial pemphigoid (OIP), ocular degenerative conditions, and a post-surgery conditions, the delivery of at least one drug into an intrascleral space is necessary.

However, the eye is a well-protected organ having several natural barriers to prevent foreign substances from entering the anterior and/or posterior segment of the eye. In addition, many of the therapeutic agents for treating posterior segment eye diseases have a high molecular weight and therefore can hardly diffuse across the ocular tissues when applied to the surface of the sclera. In other words an external application is without effect.

An intravitreal injection is the most commonly used method for drug delivery into an intrascleral space. Although it is accepted by most ophthalmologists as a method of treatment, it is a surgical-level procedure. The intravitreal injection brings risks and problems such as low patient compliance and high time consumption. Furthermore it can only be performed by surgeons and it causes an open wound to the eye that it is prone to infections, and may produce side-effects.

US 2008 0177220 A1 relates to processes, systems, and apparatuses for transscleral delivery of pharmaceutical formulations to the eye using ultrasound. In one embodiment, a transducer is placed in contact with a coupling media contained in a coupling well in contact with the sclera. When the transducer is placed at a desired standoff distance, ultrasonic waves are emitted to increase tissue porosity and to transport a therapeutic agent through the sclera tissue and into the eye. In another embodiment, a function generator is coupled to an amplifier, a matching network, and a transducer configured to maximize the cavitation effect of ultrasonic waves for drug delivery across a sclera.

US 20100226971 A1 relates to a system and method for transscleral delivery of therapeutic agents, including macromolecules, into a target site in intrascleral space using ultrasound. The system enhances transscleral diffusivity of macromolecular therapeutic agents and causes little damages to ocular tissues and structure.

The corresponding apparatuses for ultrasound-based drug delivery are complex and expensive and the corresponding method of use is inconvenient for the patient and the doctor. For example the ultrasound emission from the state of the art is intense and generates cavitation effects and/or heating of the eye tissue. Both of the latter are dangerous and uncomfortable for the patient.

SUMMARY OF THE INVENTION

A need exists for an improved and non-invasive method for delivering drugs to the posterior segment of the eye is needed.

Additional advantages, objects, and features of the present invention will be set forth in part in the description which follows and in part will become apparent to those having ordinary skill in the art upon examination of the following or may be learned from practice. The objectives and other advantages may be realized and attained by the structure particularly pointed out in the written description and claims hereof as well as the appended drawings. The above problems are solved by the subject-matter of the independent claims. The dependent claims relate to further aspects of the invention.

In one aspect of the invention relates to a drug applicator for a system for ultrasound-enhanced delivery of at least one drug to a target site in an intraocular space, the system comprising a signal generating unit operationally connected to an ultrasound transducer. The drug applicator comprises at least one space holding the drug. The drug applicator is made from a low ultrasound attenuation material. Further, the drug applicator is configured to provide low ultrasound loss coupling of the system to the sclera, and the drug applicator is configured to be mechanically coupled to the system and further configured to be coupled to the ultrasound transducer with low ultrasound loss. The signal generating unit and/or the ultrasound transducer are configured to emit an ultrasound wave form in at least one application cycle, the application cycle comprising at least one ultrasound emitting event with time duration TA and a waiting period with time duration TW.

One aspect of the invention relates to a system for ultrasound-enhanced transscleral delivery of at least one drug (molecules) to a target site in an intraocular space. The system comprises a signal generating unit operationally connected to an ultrasound transducer and a drug applicator. The drug applicator comprises at least one space holding the drug. The drug applicator is made from a low ultrasound attenuation material. Further, the drug applicator is configured to provide low ultrasound loss coupling of the system to the sclera, and the drug applicator is configured to be mechanically coupled to the system and further configured to be coupled to the ultrasound transducer with low ultrasound loss. The signal generating unit and/or the ultrasound transducer are configured to emit an ultrasound wave form in at least one application cycle, the application cycle comprising at least one ultrasound emitting event with a time duration TA and a waiting period with time duration TW.

The term low ultrasound attenuation material relates to any material with an ultrasound attenuation of less than 10 dB/(MHz cm), preferably less than 6 dB/(MHz cm), and more preferably less than 5 dB/(MHz cm). The term low ultrasound coupling loss relates to a coupling between two elements with a loss of less than 20%, preferably less than 10% at the coupling interface. However, the skilled person realizes that the above numbers reflect what is commonly considered a low value for the respective property.

In an embodiment of the invention, the drug is provided in a liquid state. In an alternative embodiment, the drug can be encapsulated in hydrophilic substances, e.g., a hydrogel or another similar substance. In an alternative embodiment, the drug can be encapsulated in amphiphilic substances, e.g., amphiphilic nanoparticles or a gel matrix. In an alternative embodiment, the drug can be encapsulated in hydrophobic substances. In an alternative embodiment, the drug can in a solid form. Depending on the embodiment, it may be advantageous to provide an additional substance to alter at least one physical, chemical, and/or pharmaceutical property of the drug.

In an embodiment of the invention the drug is selected from the list: antibodies, biologics conjugates, protein drug conjugates, corticosteroid drug conjugates, drug-encapsulated nanoparticles, drug-conjugated nanoparticles, protein drugs, biologics, corticosteroid drugs, nonsteroidal anti-inflammatory drugs, charged molecules, uncharged molecules, nucleotides, DNA/RNA aptamers, and DNA/RNA aptamers conjugated to proteins/antibodies.

In an embodiment of the invention, the ultrasound application cycle is in fact be a single application cycle comprising one ultrasound emitting event with a time duration TA and one waiting period with a time duration TW.

In an embodiment of the invention, the application cycle is repeated a plurality of times, each of the application cycles comprising one ultrasound emitting event with a time duration TA and one waiting period with a time duration TW. Preferably the application cycle is repeated 2 to 10 times, more preferably 4 times.

In an embodiment of the invention the different application cycles have different ultrasound emitting durations and different wait time durations.

The drug applicator may be configured to be exchangeable and/or may be designed for a single use application.

In an embodiment of the invention, at least one surface of the drug applicator and at least one surface of the ultrasound transducer and/or an application head which comprises the ultrasound transducer are formed to receive each other and to facilitate a coupling. Preferably the coupling is a positive-fitting and/or a friction-locked connection; however, there are also other coupling methods to be used. An exchangeable drug applicator is designed to be coupled and decoupled multiple times to the system and a single use drug applicator is designed to be coupled and decoupled at least one time to the system.

In an embodiment of the invention, at least one surface of the ultrasound transducer and/or the application head comprising the ultrasound transducer is formed to receive differently formed drug applicators.

In an embodiment of the invention, the outer appearance of the drug applicator is indicating the contained drug. In this embodiment the outer appearance relates a shape of at least one surface, preferably the coupling surface, and/or at least one human- or machine-readable label. Additionally or alternatively color coding is used to indicate the contained drug.

In an embodiment of the invention, the drug receiving space is substantially sealed at a surface designated for coupling with the sclera and the seal is configured to allow for drug permeation.

In one embodiment of the invention, the drug applicator comprises a drug receiving space that is closed to an exterior space, thereby sealing off the drug from any undesired contact with outside gases or substances. In this embodiment the at least one of the sealing surfaces preferably is configured to allow for drug permeation preferably during the ultrasound application or wait period of the application cycle.

In another embodiment of the invention, the drug receiving space is substantially open at a surface designated for coupling with the sclera.

In one embodiments of the invention the drug receiving space is substantially sealed prior to use, i.e., during fabrication, storage, and/or transport. At least one surface is preferably configured such that the seal is completely or partially removed prior to use thereby forming an opening at a surface designated for coupling with the sclera.

In an embodiment of the invention, the drug applicator is configured to be filled and/or refilled, and wherein the drug applicator receives between 10 µL and 1 mL of the drug and optionally at least one additional substance.

In one embodiment of the invention, the drug receiving space is an empty space. The empty space is configured to be filled with the drug. The filling is, e.g., performed with an injection needle and the drug applicator is essentially self sealing the needle hole after the drug has been injected into the drug receiving space and the needle has been removed. Alternatively, the filling can be performed using a port structure formed at the drug applicator. The port structure is configured to receive a needle and/or drug container and has a channel allowing for filling the drug into the drug receiving space. Furthermore, the port structure is preferably configured to seal the drug receiving space after the drug has been inserted.

In one embodiment of the invention the drug receiving space is substantially open at a surface designated for coupling with the sclera. In this and any similar embodiment the drug receiving space is preferably filled directly using the opening at a surface designated for coupling with the sclera.

In one embodiment of the invention at least one additional substance is filled into the drug receiving space, e.g. an ultrasound coupling agent.

In the system according to any of the embodiments, the drug applicator may be made from an elastic material having Young's modulus of less than 10 GPa According to the present invention the design of the drug applicator is not dictated by the ultrasound transmission properties. In particular, no defined stand-off distance between the ultrasound transducer and the sclera has to be maintained. Instead the design is variable and is preferably optimized to enable a low loss coupling and a pleasant user experience.

In one embodiment of the invention, the drug applicator is relatively soft and adapts to different application angles and different shapes of the eye. Therefore the usability is optimized.

The drug applicator may be made from at least one of the following materials: epoxy resin, polyurethane rubber, polycarbonate, nylon 6-6, polyvinyl chloride, polyester, ultra-high molecular weight polyethylene, polypropylene, Teflon, polystyrene, neoprene rubber, polyvinyl alcohol, polydimethylsiloxane, silicone-containing rubber, silicon hydrogel, silicone rubber. Still in the same aspect of the invention the drug applicator is additionally or alternatively made from silicon rubber doped with at least one of the following materials: nickel, silver, palladium, tungsten, gold, platinum, silicon oxide, titanium oxide, aluminum oxide, barium sulphate, iron oxide, zirconium dioxide, cerium oxide, bismuth oxide, ytterbium oxide, lutetium oxide, hafnium oxide.

The system may further comprise a controller, wherein the controller is configured to control at least one of a plurality of parameters of the application cycle, the plurality parameters of the application cycle are selected from the following: the time duration TA of the ultrasound emitting event, the time duration TW of the wait period after the ultrasound emitting event, the number of application cycles, the intensity of the ultrasound emitting event, the central frequency of the ultrasound emitting event, the mechanical index of the ultrasound emitting system, and in case of a pulsed ultrasound emitting event: the repetition rate of the ultrasound emitting event and the duty cycle of the ultrasound emitting event.

In an embodiment of the invention, the controller is operationally connected with at least one of the following: the application head, the signal generating unit, the ultrasound transducer, and the drug applicator. The connection is preferably wireless or with a cable.

In an embodiment of the invention, the ultrasound signal has in sine wave form at a central frequency between 20 kHz and 100 kHz, preferably at 40 kHz. In one embodiment of the invention, the ultrasound signal has a spatial average temporal average intensity no greater than 4 $W/cm^2$, preferably in the range between 0.005 $W/cm^2$ and 1 $W/cm^2$. In one embodiment of the invention, the ultrasound emitting device and/or the controller is configured such that continuous or pulsating waves are generated and the ultrasound is applied as pulsating waves with a duty cycle preferably ranging from 30% to 0% with a pulse repetition rate preferably between 1 Hz to 100 Hz.

In an embodiment of the invention, the mechanical index of the ultrasound application cycle does not exceed 0.20 to avoid violent effects and tissue damage induced by the ultrasound. The mechanical index predicts the cavitation activities during the ultrasound application period at a particular combination of frequency and intensity. The mechanical index is therefore preferably controlled by the frequency and intensity of the ultrasound emission.

In an embodiment of the invention, the system may further comprise an information receiving and/or sending unit. The information receiving and/or sending unit may be configured to receive and/or send information related to the drug. The information receiving and/or sending unit can be operationally connected to the signal generating unit and/or the controller. Alternatively, the information receiving and/or sending unit can be operationally connected to the signal generating unit and/or the controller and the controller configured to control at least one of a plurality of parameters of the application cycle based on the information related to the drug. The information related to the drug is preferably stored on the drug applicator.

In order to be delivered effectively, different types of drug may require different parameters of the application cycle. In an embodiment of the invention, the system is able to receive information from the drug applicator and identify the drug applicator and thus identify the type of drug and control the different parameters of the application cycle accordingly.

The information related to the drug and/or the drug applicator can be stored in, at, and/or on the drug applicator using different methods and requiring different methods for the information sending and/or receiving unit to retrieve the information from the drug applicator.

In an embodiment of the invention a lock and key method is used to identify the drug applicator. At least one surface of the drug applicator and at least one corresponding surface of the application head having a matching shape to allow for a positive locking connection. Due to the positive locking the drug applicator is identified and the different parameters of the application cycle are controlled accordingly. Positive-locking of more than one different drug applicator is possible, preferably using different locking-surfaces on the application head. The different drug applicators lock in a different end position and the information about the drug applicator is coded in the different end positions and is retrieved by the information receiving and/or sending unit.

In an embodiment of the invention a human- and/or machine-readable label is used store the information about the drug applicator. Accordingly, the information receiving and/or sending unit would comprise respective means for reading the human- and/or machine-readable label.

Alternatively or additionally, an RFID chip in or on the drug applicator is preferably used to store the information about the drug applicator. Accordingly the information receiving and/or sending unit would comprise an RFID reader.

The information about the drug applicator preferably contains at least one of the following information: information about the drug in the drug applicator, information about the shelf life of the drug, information about the application cycle.

The above lists are not intended to limit the scope of the subject-matter protection is sought for. The skilled person will conceive a plurality of improvements and/or variations of the above solutions once presented with the problem of storing information on the drug applicator.

In an embodiment the drug applicator is filled with a drug from a container holding several doses of the drug. In this embodiment the information sending and/or receiving unit is configured to receive the information about the drug from the container.

In an embodiment of the invention, when the drug comprises molecules with a size of 70 kDa or less, the controller is configured to control the time duration TA to be between 30 s and 300 s and the drug applicator is configured such that the drug transit through the sclera during the time duration TA. Additionally or alternatively, when the drug comprises molecules with a size of more than 70 kDa, the controller is configured to control the time duration TW to be between 60 s and 600 s and the drug applicator is configured such that the molecules drug transit through the sclera during the time duration TW.

It is an embodiment of the invention that the effectiveness of the delivery is dependent on the molecule size. For relatively small molecules, preferably smaller than 70 kDa, the penetration rate and/or depth is effectively controlled by controlling the duration of the ultrasound emission event of the at least one application cycle. For relatively large molecules, preferably larger than 70 kDa, the penetration rate and/or depth is controlled effectively by controlling the duration of the wait period after the ultrasound emission event of the at least one application cycle. Therefore for each drug an optimal set of parameters for the application cycle can be found.

In an embodiment of the invention, optimal sets of parameters of the application cycle for different drugs are stored in the system. Additionally or alternatively, the optimal sets may be added, modified, or deleted by a user and/or a remote access using connecting means. The system is preferably further connected to a central database, the database being configured to manage and distribute the optimal sets.

In an embodiment of the invention, the optimal set of parameters of the application cycle for the respective drug that is contained within the drug applicator is stored at, in and/or on the drug applicator itself and can be retrieved with the information receiving/sending unit.

In an embodiment of the invention, the system further comprises display and/or manual input unit configured to display and/or manually set at least one of the plurality parameters of the application cycle.

In certain situations, e.g., specific individual conditions of the eye to be treated, it is necessary to change at least one of the plurality parameters of the application cycle manually. In one embodiment of the invention the system comprises a display unit that is configured to display the parameters of the application cycle and preferably other information assisting the user. In one embodiment of the invention the system comprises, additionally or alternatively to the display unit a manual input unit to set at least one of the plurality parameters of the application cycle.

The display unit and the manual input unit are preferably combined in one unit, e.g., in a touch-screen device. The display unit and/or the manual input unit are integrated with the system or coupled to the system with connecting means. Connecting means preferably comprise a cable and/or wireless connection.

In an embodiment of the invention, the system further comprises a temperature sensor configured to sense the temperature of the surface of the sclera, preferably a thermocouple and/or an infrared thermometer. And the controller is configured to control the ultrasound emission event such that during the time TA the temperature of the surface of the sclera does not increase by more than 1° ° C.

The heating of the sclera surface is a critical aspect of ultrasound enhanced delivery of drugs to a target site in the intraocular space. In one embodiment of the invention is the heating of this sclera is measured. The heating can be measured using different methods known to the skilled person.

In an embodiment of the invention and infrared thermometer is used for measuring the heating of an area of the sclera where the ultrasound applied, during a time when the ultrasound is applied. In one embodiment of the invention a thermocouple is used to measure the heating of an area of the sclera where the ultrasound is applied, during a time when the ultrasound is applied.

In an embodiment of the invention the parameters of the application cycle are controlled such that the heating of an area of the sclera where the ultrasound is applied, during a time when the ultrasound is applied, does not exceed 1° C., advantageously it does not exceed 0.5° C. Preferably, the intensity and/or the application time TA are controlled to control the heating of the sclera.

The invention further relates to a method for using the system of any one of the above aspects and embodiments of the invention to deliver drugs to a target site in the intraocular space. In one aspect of the invention, the method for the delivery of a drug to a target site in a intraocular space comprises the steps of providing a drug applicator and/or a system according any one of the above aspects and/or embodiments, coupling the drug applicator to a surface of the sclera, and applying at least one ultrasound application cycle, wherein the application cycle comprises an ultrasound application with a time duration TA and a waiting period with a time duration TW.

In an embodiment of the invention, the step of coupling the system to the eye comprises applying a pressure to the drug applicator and pressing the drug applicator to the surface of the sclera.

In an embodiment of the invention the drug applicator is formed from a soft and elastic material. To couple the drug applicator to the eye, the user and/or doctor may press the drug applicator to the eye. The drug applicator is elastically deformed upon contact with the surface of the sclera and thereby forming an interface between the drug applicator and the surface of the sclera. The interface is preferably increased in size when the pressure is increased. The material of the drug applicator has to be adapted to not cause an unpleasant sensation to the eye. Adaptation preferably comprises any selection of the following: adapting the elasticity, adapting the temperature and/or adapting the structure.

In an embodiment of the invention, the step of coupling the system to the eye additionally comprises the step of applying an ultrasound coupling agent to the drug applicator and/or to the surface of the sclera prior to pressing the drug applicator to the surface of the sclera. In an embodiment of the invention applying an ultrasound coupling agent to the drug applicator and/or to the surface of the sclera prior to pressing the drug applicator to the surface of the sclera improves the transmission of the ultrasound signal to the sclera tissue.

In an embodiment of the invention, the step of providing a drug applicator and/or a system additionally comprises the step of loading a drug into the drug applicator.

In an embodiment the drug applicator forms a cartridge that is designed to be attached to the system.

In an embodiment of the invention the drug applicator does not permanently hold a drug. The drug is loaded into the drug applicator prior to the ultrasound application. The loading can be performed using any of the above described methods of filling the drug applicator with an injection needle, a port structure, and/or a direct filling method.

In an embodiment of the invention, the step of providing a drug applicator and/or a system additionally or alternatively comprises the step replacing an empty drug applicator with pre-loaded drug applicator.

In an embodiment of the invention, the drug applicator is pre-loaded with the drug. An empty or blank drug applicator and/or empty previous used drug applicator is removed from the system and a pre-loaded drug applicator is coupled to the system prior to the ultrasound application.

In an embodiment of the invention, the method additionally comprises the step of determining the plurality of parameters of the application cycle, comprising at least the number of application cycles the time durations TA and TW, by the information about the drug received from the information sending and/or receiving unit.

In an embodiment of the invention, the plurality of parameters of the application cycle, comprising at least the number of application cycles the time durations TA and TW, is manually inputted by a user.

In an embodiment of the invention, the temperature of the surface of the sclera is measured during the application time TA, and the controller controls the ultrasound emission such that the temperature increase of the surface of the sclera does not exceed 1° C., advantageously it does not exceed 0.5° C.

Aspects of the invention are directed to a device for delivery of at least one drug to a target side in an intraocular space of an eye, wherein the device comprises: an ultrasound-generating device configured to generate ultrasound that is delivered to a desired site of the eye; and an interface configured to couple the device, without the use of tools, to a drug applicator comprising the at least one drug, wherein the drug applicator is configured to aid in the delivery of the ultrasound to the desired site of the eye, wherein the device has a volume of less than 2500 cm³.

In an embodiment of the invention, the device and drug applicator, when the drug applicator is coupled via the interface, has a volume of less than 3000 cm³. In an embodiment of the invention, the device has a volume of less than 1000 cm³. In an embodiment of the invention, the device has a maximum dimension of less than 25 cm. In an embodiment of the invention, the device and drug applicator, when the drug applicator is coupled via the interface, has a maximum dimension of less than 30 cm. In an embodiment of the invention, the device has a maximum dimension of less than 15 cm. In an embodiment of the invention, the device has a weight of less than 9 kg. In an embodiment of the invention, the device and drug applicator have a collective weight of less than 10 kg.

In an embodiment of the invention, the device further comprises a housing that at least partially encloses the ultra-sound generating device. In an embodiment of the invention, the device further comprises a signal generating unit in communication with the ultrasound-generating unit. In an embodiment of the invention, the signal generating unit comprises a controller configured to control the signal generating unit and an amplifier configured to generate an ultrasound signal. In an embodiment of the invention, the device is a handheld device. In an embodiment of the invention, the device is a wearable device. In an embodiment of the invention, the device is configured to be worn on a user's head at least partially over an eye of the user.

In an embodiment of the invention, the ultrasound-generating device is configured to operate at a frequency between 20 kHz and 100 kHz. In an embodiment of the invention, wherein the ultrasound-generating device operates at an excitation voltage of less than 30 $V_{RMS}$. In an embodiment of the invention, the ultrasound-generating device comprises a flexural transducer. In an embodiment of the invention, the ultrasound-generating device weighs less than 200 g. In an embodiment of the invention, the ultrasound-generating device has a maximum dimension less than 3 cm.

In an embodiment of the invention, the interface permits repeatable coupling and decoupling of the drug applicator with the device. In an embodiment of the invention, the drug applicator is configured to hold at least 100 µl of the at least one drug. In an embodiment of the invention, the device is powered by an on-board power source. In an embodiment of the invention, the power source comprises primary cell batteries.

Further aspects of the invention are directed to a method for generating instructions for delivery of at least one drug to a target site in an intraocular space of an eye, said method comprising: obtaining a signal indicative of an identity of the at least one drug to be delivered or an identity of a treatment plan for the eye; and generating, with aid of one or more processors, instructions for operation of an ultrasound-generating device based on the signal indicative of the identity of the at least one drug to be delivered or the identity of a treatment plan for the eye.

The method may further comprise applying ultrasound using the ultrasound-generating device in accordance with the instructions to effect delivery of the at least one drug to the target site in the intraocular space of the eye. In an embodiment of the invention, the signal is provided in response to a user input of the identity of the at least one drug or the identity of the treatment plan for the eye. In an embodiment of the invention, the at least one drug is contained in a drug applicator operably coupled to the ultrasound-generating device. In an embodiment of the invention, the drug applicator is removably coupled to the ultrasound-generating device. In an embodiment of the invention, the drug applicator is coupled to the ultrasound-generating device in a removable fashion. In an embodiment of the invention, the signal is provided in response to a label on-board the drug applicator indicative of the at least one drug to be delivered or the identity of the treatment plan for the eye. In an embodiment of the invention, the drug applicator is pre-loaded with the at least one drug.

In an embodiment of the invention, the determination of the instructions comprises selecting the instructions from a plurality of instruction options for various drugs or treatment plans. In an embodiment of the invention, the one or more processors are on-board a device comprising the ultrasound-generating device. In an embodiment of the invention, the instructions comprise a frequency of the ultrasound. In an embodiment of the invention, the instructions comprise a mechanical index. In an embodiment of the invention, the instructions comprise a number of cycles and timing of the generation of the ultrasound.

In an embodiment of the invention, the generation of ultrasound permits draining of fluid from within the eye to reduce pressure within the eye. In an embodiment of the invention, the draining of fluid occurs concurrently with the delivery of the at least one drug. In an embodiment of the invention, the draining of fluid occurs prior to the delivery of the at least one drug. In an embodiment of the invention, the draining of fluid occurs subsequent to the delivery of the at least one drug. In an embodiment of the invention, the ultrasound operates at a frequency below 1 MHz when draining the fluid from within the eye. In an embodiment of the invention, a temperature of the eye is increased by no more than 2 degree C. when draining the fluid from within the eye. In an embodiment of the invention, the draining of fluid occurs during treatment of reducing intraocular pressure. In an embodiment of the invention, the draining of the fluid occurs during treatment of glaucoma.

In an embodiment of the invention, the identity of the treatment plan for the eye comprises an identity of a disease being treated.

Additional aspects of the invention are directed to a device for delivery of at least one drug to a target side in an intraocular space of an eye, wherein the device comprises: an ultrasound-generating device configured to generate ultrasound that is delivered to a desired site of the eye; and an interface configured to repeatedly couple the device to a drug applicator comprising the at least one drug, wherein the drug applicator is configured to aid in the delivery of the ultrasound to the desired site of the eye, wherein the interface comprises a coupling medium having a thickness that is a multiple of a propagation speed of the coupling medium over a resonance frequency.

In an embodiment of the invention, the coupling is effectuated without the use of a tool. In an embodiment of the invention, the coupling medium has a thickness that is an odd multiple of a propagation speed of the coupling medium over four times a resonance frequency. In an embodiment of the invention, the coupling medium is configured to optimize impedance matching of the ultrasound-generating device and the drug applicator. In an embodiment of the invention, the coupling medium is a solid. In an embodiment of the invention, the coupling medium is a liquid, suspension, or gel.

In an embodiment of the invention, the ultrasound-generating device is configured to be at least partially inserted into a drug applicator case. In an embodiment of the invention, the ultrasound-generating device comprises a pin configured to slide through a slot of the case to permit the ultrasound-generating device to lock into the case. In an embodiment of the invention, the drug applicator is configured to be at least partially inserted into an ultrasound-generating device case. In an embodiment of the invention, the interface comprises a first fastener configured to mate with a second fastener on-board the drug applicator. In an embodiment of the invention, the first fastener and the second fastener are configured to be screwed together. In an embodiment of the invention, the first fastener and the second fastener are configured to snap together. In an embodiment of the invention, the interface permits a magnetic connection between the ultrasound-generating device and the drug applicator.

In an embodiment of the invention, the drug applicator has an attenuation coefficient of 5 dB/MHz/cm or lower. In an embodiment of the invention, the interface provides a coupling loss of less than 10%. In an embodiment of the invention, the ultrasound-generating device is configured to operate at a frequency between 20 kHz and 100 kHz. In an embodiment of the invention, the ultrasound-generating device operates at an excitation voltage of less than 30 $V_{RMS}$. In an embodiment of the invention, the ultrasound-generating device comprises a flexural transducer.

In accordance with further aspects of the invention, a device for delivery of at least one drug to a target side in an intraocular space of an eye is provided. The device may comprise: an ultrasound-generating device configured to generate ultrasound that is delivered to a desired site of the eye; a light source configured to generate light that is delivered to the desired site of the eye; and an interface configured to couple the device to a drug applicator comprising the at least one drug, wherein the drug applicator is configured to aid in the delivery of the ultrasound to the desired site of the eye and is configured to permit the light from the light source to be delivered to the desired site of the eye.

In an embodiment of the invention, the light source is configured to generate UV light. In an embodiment of the invention, the light source is configured to emit light at UV-A wavelengths. In an embodiment of the invention, the light from the light source is configured to cause cross-linking of the at least one drug upon exposure of the at least one drug to the light. In an embodiment of the invention, the at least one drug comprises a light-sensitive molecule. In an embodiment of the invention, the at least one drug comprises riboflavin.

In an embodiment of the invention, the ultrasound-generating device and the light source are enclosed within a housing. In an embodiment of the invention, the light source is coupled to the ultrasound-generating device. In an embodiment of the invention, the light source has a fixed position relative to the ultrasound-generating device. In an embodiment of the invention, the ultrasound-generating device comprises an interior space within which the light source resides. In an embodiment of the invention, the ultrasound-generating device has a circular cross-section with a free space in the middle that forms the interior space. In an embodiment of the invention, the interior space further comprises an optical element that modifies light emitted by the light source. In an embodiment of the invention, the ultrasound-generating device comprises an interior space within which a data collection device resides. In an embodiment of the invention, the recording device is a camera or a microphone.

In an embodiment of the invention, the ultrasound-generating device weighs less than 200 g. In an embodiment of the invention, the ultrasound-generating device has a maximum dimension of less than 3 cm. In an embodiment of the invention, the light source is configured to direct light through the drug applicator when the drug applicator is coupled to the device.

Moreover, aspects of the invention may be directed to a drug applicator for delivery of at least one drug to a target site in an intraocular space of an eye, wherein the drug applicator comprises: a first portion formed from an opaque material configured to at least partially define at least one space configured to hold the at least one drug; a second portion formed from a material that is at least partially transparent to light of selected wavelengths, configured to permit light of the selected wavelengths to pass from one side of the drug applicator to another side of the drug applicator; and an interface configured to couple the drug applicator to an ultrasound-generating device configured to generate ultrasound that is delivered to a desired site of the eye via the drug applicator.

In an embodiment of the invention, the ultrasound-generating device is operably coupled to a light source configured to provide the light of selected wavelengths. In an embodiment of the invention, the light source is configured to generate UV light. In an embodiment of the invention, the light from the light source is configured to cause cross-linking of the at least one drug upon exposure of the at least one drug to the light. In an embodiment of the invention, the at least one drug comprises riboflavin. In an embodiment of the invention, the ultrasound-generating device and the light source are enclosed within a housing. In an embodiment of the invention, the ultrasound-generating device comprises an interior space within which the light source resides.

In an embodiment of the invention, the at least one space is a single continuous space. In an embodiment of the invention, the at least one space comprises multiple discontinuous spaces. In an embodiment of the invention, the multiple discontinuous spaces comprises pores.

In an embodiment of the invention, the first portion comprises an outer surface that is coated with a material that reflects the light of selected wavelengths. In an embodiment of the invention, the material is configured to reflect UV light to reduce any UV exposure to an outer environment. In an embodiment of the invention, the first portion comprises a target side configured to contact a desired site of the eye. In an embodiment of the invention, the target side is formed from a soft biocompatible material. In an embodiment of the invention, the target side is configured to deliver reagents that improves delivery of the at least one drug to the target site.

In an embodiment of the invention, the first portion is formed from an elastic material. In an embodiment of the invention, the second portion is transparent to ultraviolet light. In an embodiment of the invention, the second portion is surrounded by the first portion.

In an embodiment of the invention, the drug applicator is configured to be pre-loaded with the at least one drug. In an embodiment of the invention, the drug applicator comprises a sealing material configured to prevent contamination. In an embodiment of the invention, the drug applicator is configured to receive in situ loading of the at least one drug.

An aspect of the invention provides a method for delivery of at least one drug to a target site in an intraocular space of an eye, said method comprising: applying a drug-holding overlay to a surface of the eye comprising the at least one drug, wherein the drug-holding overlay is configured to permit closure of the eye while the drug-holding overlay is applied to the surface; positioning an ultrasound-generating device to a desired site of the eye; and generating ultrasound using the ultra-sound generating device and applying the ultrasound to the desired site, wherein the generation of the ultrasound delivers the at least one drug to the target site in the intraocular space of the eye without damaging tissue of the eye.

In an embodiment of the invention, the drug-holding overlay is a contact lens or a film. In an embodiment of the invention, the drug-holding overlay is formed of a porous material. In an embodiment of the invention, the drug-holding overlay is formed of a hydrophilic, hydrophobic, amphiphilic, and sterile material. In an embodiment of the invention, the at least one drug is encapsulated in the drug-holding overlay. In an embodiment of the invention, the at least one drug is adhered on a surface of the drug-holding overlay. In an embodiment of the invention, the drug-holding overlay has an attenuation coefficient of 5 dB/MHz/cm or lower.

In an embodiment of the invention, the ultrasound-generating device is positioned over an eyelid of the eye. In an embodiment of the invention, the ultrasound-generating device is positioned on a sclera of the eye. In an embodiment of the invention, the ultrasound-generating device is positioned on a cornea of the eye. In an embodiment of the invention, the ultrasound-generating device comes into contact with the drug-holding overlay.

The method may further comprise providing a drug applicator that is operably coupled to the ultrasound-generating device. In an embodiment of the invention, the drug applicator is positioned over an eyelid of the eye. In an embodiment of the invention, the drug applicator is positioned over a sclera of the eye. In an embodiment of the invention, the drug applicator is positioned over a cornea of the eye.

Aspects of the invention are also directed to a device for delivery of at least one drug to a target side in an intraocular space of an eye, said device comprising: an eyewear frame comprising at least one extension configured to extend behind a wearer's ear when the device is worn by the wearer; and one or more ultrasound-generating devices supported by the eyewear frame, wherein each ultrasound-generating device is configured to generate ultrasound that is delivered to a desired site of the eye when the device is worn by the wearer, wherein the generation of the ultrasound delivers the at least one drug to the target site in the intraocular space of the eye without damaging tissue of the eye.

The device may further comprise a drug applicator supported by the eyewear frame, said drug applicator comprising the at least one drug. In an embodiment of the invention, the drug applicator is operably coupled to the one or more ultrasound-generating devices. In an embodiment of the invention, the drug applicator is located to at least partially cover the eye when the device is worn by the wearer.

In an embodiment of the invention, the eyewear frame comprises a glasses frame. In an embodiment of the invention, the eyewear frame forms goggles. In an embodiment of the invention, the eyewear frame forms a helmet comprising a portion that covers at least one eye.

In an embodiment of the invention, the ultrasound-generating device is affixed to the eyewear frame. In an embodiment of the invention, the ultrasound-generating device is removable from the eyewear frame. In an embodiment of the invention, the ultrasound-generating device is movable from one portion of the eyewear frame to another portion of the eyewear frame. In an embodiment of the invention, the ultrasound-generating device is located to at least partially cover the eye when the device is worn by the wearer.

A method for delivery of at least one drug to a target site in an intraocular space of an eye is provided in accordance with aspects of the invention. The method may comprise: positioning an ultrasound-generating device and a drug applicator relative to a desired site of a sclera of the eye, wherein the drug applicator comprises the at least one drug; and generating ultrasound using the ultra-sound generating device and applying the ultrasound to the desired site of the sclera at a frequency of about 30 to 60 KHz and a mechanical index of between 0.1 and 0.3, wherein the generation of the ultrasound delivers the drug to the target site in the intraocular space of the eye at a concentration of at least 1.3 $\mu$g/ml at a speed of at least 90 $\mu$m$^2$/s without damaging tissue of the eye.

The method may further comprise at least partially enclosing the ultra-sound generating device within a housing. In an embodiment of the invention, the housing permits the ultrasound-generating device to be handheld. In an embodiment of the invention, the housing permits the ultrasound-generating device to be worn. The method may further comprise providing communications from a signal generating unit to the ultrasound-generating unit. In an embodiment of the invention, the signal generating unit comprises a controller configured to control the signal generating unit and an amplifier configured to generate an ultrasound signal.

In an embodiment of the invention, the ultrasound-generating device operates at an excitation voltage of less than 30 $V_{RMS}$. In an embodiment of the invention, the ultrasound-generating device comprises a flexural transducer. In an embodiment of the invention, the ultrasound-generating device weighs less than 200 g. In an embodiment of the invention, the ultrasound-generating device has a maximum dimension less than 3 cm. In an embodiment of the invention, the drug applicator and the ultrasound-generating device are configured to coupled and decoupled from one another.

In an embodiment of the invention, the drug applicator is positioned to contact the eye at the desired site. In an embodiment of the invention, the drug applicator is positioned to contact a different portion of the eye than the desired site. In an embodiment of the invention, the drug applicator is configured to hold at least 100 $\mu$l of the at least one drug. In an embodiment of the invention, the drug delivered to the target site comprises molecules of at least 70 kDa. In an embodiment of the invention, the ultrasound is generated for a time duration of less than 300 s.

Also, aspects of the invention may be directed to a method for ultrasound-enhanced delivery of at least one drug to a target site in an intraocular space of an eye, said method comprising: positioning an ultrasound-generating device and a drug applicator relative to a desired site of a sclera of the eye, wherein the drug applicator comprises the at least one drug; and generating ultrasound using the ultra-sound generating device and applying the ultrasound to the desired site of the sclera with a mechanical index of between 0.1 and 0.3, wherein the generation of the ultrasound delivers the drug to the target site in the intraocular space of the eye at a concentration of at least 1.3 $\mu$g/ml at a speed of at least 90 $\mu$m$^2$/s without damaging tissue of the eye and without increasing temperature of the tissue by more than 1 degree C.

The method may further comprise at least partially enclosing the ultra-sound generating device within a housing. In an embodiment of the invention, the housing permits the ultrasound-generating device to be handheld. In an embodiment of the invention, the housing permits the ultrasound-generating device to be worn.

The method may further comprise providing communications from a signal generating unit to the ultrasound-generating unit. In an embodiment of the invention, the signal generating unit comprises a controller configured to control the signal generating unit and an amplifier configured to generate an ultrasound signal.

In an embodiment of the invention, the ultrasound-generating device operates at an excitation voltage of less than 30 $V_{RMS}$. In an embodiment of the invention, the ultrasound-generating device comprises a flexural transducer. In an embodiment of the invention, the ultrasound-generating device weighs less than 200 g. In an embodiment of the invention, the ultrasound-generating device has a maximum dimension less than 3 cm. In an embodiment of the invention, the drug applicator and the ultrasound-generating device are configured to coupled and decoupled from one another.

In an embodiment of the invention, the drug applicator is positioned to contact the eye at the desired site. In an embodiment of the invention, the drug applicator is positioned to contact a different portion of the eye than the desired site. In an embodiment of the invention, the drug applicator is configured to hold at least 100 μl of the at least one drug. In an embodiment of the invention, the drug delivered to the target site comprises molecules of at least 70 kDa. In an embodiment of the invention, the drug delivered to the target site comprises small molecules below 900 Da. In an embodiment of the invention, the drug delivered to the target site comprises large molecules below 250 kDa. In an embodiment of the invention, the ultrasound is generated for a time duration of less than 300 s.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

FIGS. 6A to 6D show various embodiments of a drug applicator;

FIG. 23 shows further examples of effects of various mechanical indexes;

FIG. 30 shows an illustration of a second mouse left eye from the experimental procedure.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The application of ultrasound to a surface of an eye may aid in delivery of drugs. A system may comprise an ultrasound-generating device that may be coupled to drug applicator. The ultrasound may aid in causing the drugs to penetrate to a target site within an intraocular space. The drug applicator may hold one or more drugs that may be delivered. The ultrasound will be delivered through the drug applicator to the eye. In some embodiments, the drug applicator may be separable from the device. The drug applicator may be formed from a material and have a design that may allow for low attenuation of the ultrasound delivered to the eye, while providing a comfortable connection with the eye. The drug applicator may be preloaded with a drug or a drug may be loaded in situ.

Figure 1:
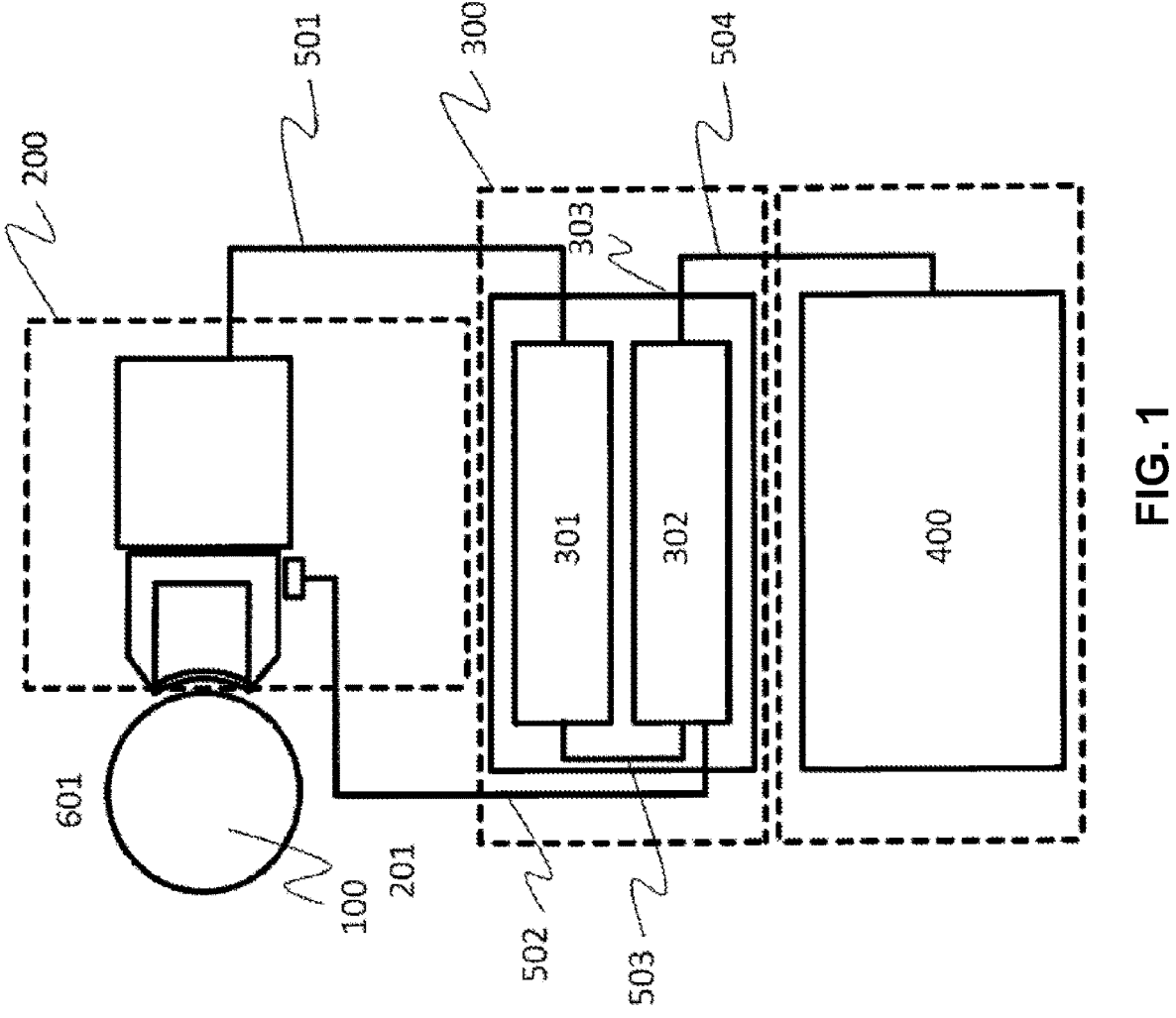
FIG. 1 shows an embodiment of the system for ultrasound enhanced delivery of drugs.

FIG. 1 shows one embodiment of a system for ultrasound enhanced delivery of drugs. The system may comprise a delivery unit 200, a signal generating unit 300, and/or an input and control unit 400.

The delivery unit 200, the generating unit 300, and the input and control unit 400 may be operationally interconnected by communication links 501, 503, 504. Communication links may comprise wired and wireless communications. Preferable communication mechanisms may include direct communication link, such as a WiFi, infrared, optical, radio, or Bluetooth communication link. Preferable communication links may also comprise wired communications, such as any kind of bus connection.

The delivery unit 200, the generating unit 300, and the input and control unit 400 are preferably integrated together into a single housing and/or are optionally arranged into functional groups and integrated into a number of housings. A single housing may partially or completely enclose the delivery unit, the generating unit, and/or the input and control unit. A housing may or may not comprise one or more internal spaces within which the delivery unit, the generating unit and/or the input control unit may be provided. The delivery unit, the generating unit, and/or input control unit may or may not share one or more internal spaces. In some instances, the units may be separated from one another. The housing may or may be fluid tight (e.g., airtight, watertight). The housing may protect one or more components within from dust, particulates, light, or other external environmental conditions. Similarly, the housing may or may not prevent emissions (e.g., light) or substances from within the housing from leaving the housing.

The delivery unit, the generating unit, and/or the input and control unit may share a common support. The common support may bear weight of the delivery unit, the generating unit, and/or the input and control unit. The common support may permit the delivery unit, the generating unit, and/or the input control unit to move together. The common support may maintain a fixed position between the delivery unit, the generating unit and/or the input control unit. The common support may or may not be a housing.

Optionally, the delivery unit, the generating unit, and the input and control unit may be part of a housing that is formed as a handheld device. The various units may be integrated into various portions of the handheld device. The various units may or may not be removable or separable from the handheld device.

In one example, the input and control unit 400 may be formed as a hand-held device comprising display and input means; the delivery unit 200 is preferably formed as a compact, optionally a hand-held, device that is configured to be ergonomically placed in front of the eye 100 and is further configured to touch the surface (e.g., scleral surface, corneal surface, limbus); and the signal generating unit 300 is preferably formed in a rugged housing, preferably having a rack compatible form factor.

The various units may form a drug delivery device. For instance, the drug delivery device may comprise the delivery unit, the generating unit, and/or the input and control unit. The drug delivery device may comprise a housing. The drug delivery device may or may not comprise an entirety of a drug delivery unit or a portion of the drug delivery unit. The drug delivery device may or may not comprise a drug applicator. The drug delivery device may be reusable. A drug applicator may or may not be reusable. For instance, a drug applicator may be reusable when it is refilled with the same drug or a different drug. The drug applicator may be disposable. In some embodiments, the drug applicator may be a single-use disposable.

The signal generating unit 300, may comprise a controller 302 and a signal generator and/or amplifier 301. The controller 302 may be operationally connected to the signal amplifier 301. The signal generator and/or amplifier 301 are operationally connected with the ultrasound transducer 202 by communication link 501. The signal generator and/or amplifier 301 and the controller 302 may be arranged in a common housing 303 of the signal generating unit 300. The housing of the signal generating unit may be separate from a housing of a delivery unit 200. Alternatively or in addition, the signal generating unit and the delivery unit may share a common housing.

In an embodiment of the invention, the controller 302 may be configured to control the signal generator and/or amplifier 301 to generate the ultrasound signal. The controller may comprise one or more processors that may generate instructions that are sent to the signal generator and/or amplifier to generate the desired ultrasound signal. The controller may determine desired ultrasound characteristics as described in greater detail elsewhere herein. Additionally or optionally the signal generator and/or amplifier 301 is configured to amplify the ultrasound signal. The emitted ultrasound signal may have any desired characteristics. Examples of characteristics that may be controlled include wave form, frequency, and/or mechanical index. In one example, the emitted ultrasound may have a sine wave form and have a central frequency between 20 kHz and 100 kHz, more preferably at 40 kHz. Any other wave forms, frequencies, and/or mechanical indexes may be provided, as described elsewhere herein.

In an embodiment of the invention, the emitted ultrasound signal may comprise pulsating waves with a duty cycle preferably ranging from 30% to 70% at a preferred pulse repetition rate between 1 Hz and 100 Hz. Various examples of emitted ultrasound signal profiles are provided in greater detail elsewhere herein.

In an embodiment of the invention, the mechanical index of the emitted ultrasound signal is not exceeding 0.2 to avoid violent effects, e.g., cavitation effects, and/or tissue damages induced by the emitted ultrasound signal. In some embodiments, the mechanical index of the emitted ultrasound is about 0.2. In some embodiments, the mechanical index may be less than or equal to about 0.01, 0.05, 0.1, 0.12, 0.15, 0.17, 0.18, 0.19, 0.2, 0.21, 0.22, 0.23 0.25, 0.27, 0.3, 0.4, 0.5, 0.6, 0.7, 0.8, or 0.9. In some instances, the mechanical index may be greater than or equal to any of the values provided, or fall within a range between any two of the values provided. The mechanical index predicts the cavitation activities during the ultrasound application at a particular combination of frequency and intensity. The mechanical index is preferably controlled by a controlling the frequency and/or intensity of the emitted ultrasound signal.

In an embodiment of the invention, the emitted ultrasound signal has a spatial average temporal average intensity of less than 4 W/cm². It is preferred that the intensity is in the range between 0.005 W/cm² and 1 W/cm². In some embodiments, the spatial average temporal average intensity may be less than or equal to about 0.001, 0.003, 0.005, 0.01, 0.03, 0.05, 0.07, 0.1, 0.15, 0.2, 0.25, 0.3, 0.35, 0.4, 0.45, 0.5, 0.6, 0.7, 0.8, 0.9, 0.95, 1, 2, 3, 4, or 5 W/cm². The intensity may be greater than any of the values provided, or may fall within a range between any two of the values provided.

The controller 302, the signal generator and/or amplifier 301, and the ultrasound transducer 202 may be collectively referred to as an ultrasound device.

The display and control unit 400 may further comprise display and a user interactive device. The display and control unit 400 is operationally connected to the ultrasound device and the information sending and/or receiving unit 203 via communication links 501, 503, 504. The communication links may comprise a cable and/or a wireless connection, or any other type of connection as described in greater detail elsewhere herein. The display and control unit may comprise a separate housing from the ultrasound device, or may share a common housing.

In an embodiment of the invention, the display and control unit 400 may be implemented as an application on a tablet computer, a laptop computer, a desktop computer, a smart phone, or a personal digital assistant. Alternatively or in addition, the display and control unit 400 may be designed as a standalone device optionally comprising a battery.

One or more portions of the drug delivery device may be powered by an on-board power source. For instance, a delivery unit, signal generating unit, and/or display and control unit may be powered by an on-board power source. The power source may comprise one or more batteries. For instance, the power source may comprise one or more primary cell batteries. The power source may comprise one or more rechargeable batteries. The power source may be used to power an ultrasound-generating device. The power source may be within a housing of a drug delivery device. The power source may or may not be removable or detachable from the drug delivery device.

In some embodiments, a delivery unit 200 may comprise multiple portions that may be coupled to one another. For instance, the delivery unit may comprise a drug applicator and an ultrasound-generating device. In some embodiments, the ultrasound-generating device may be part of the drug delivery device. The drug applicator may or may not be part of the drug delivery device. In some embodiments, the drug applicator may be provided separately from the drug delivery device. The drug applicator may be coupled to the drug delivery device. In some embodiments, the drug applicator may be coupled to the drug delivery device in a separable and/or repeatable manner.

Figure 2:
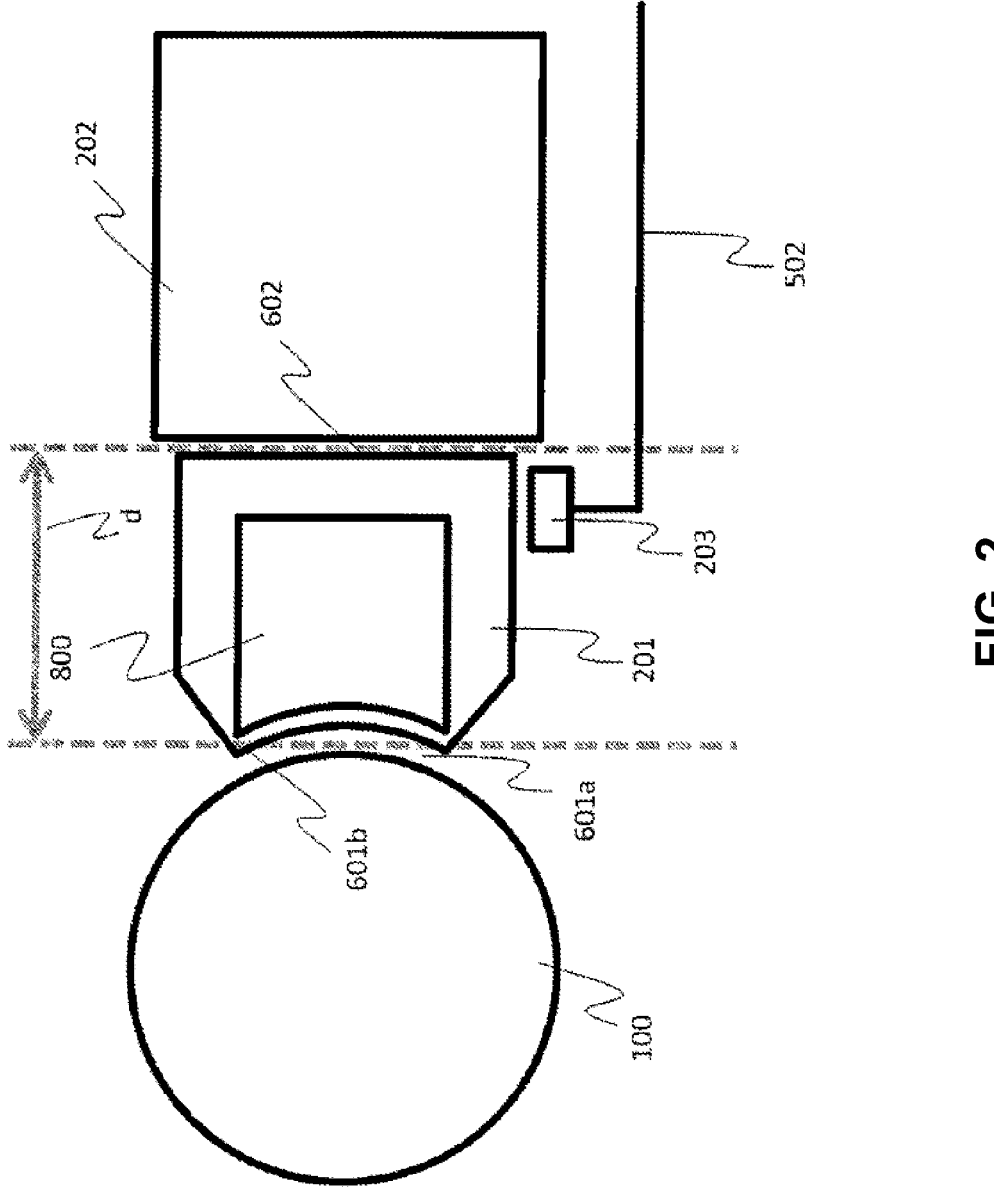
FIG. 2 shows an example of an embodiment of the delivery unit.

Details of one embodiment of the delivery unit 200 are shown in FIG. 2. The delivery unit 200 comprises a drug applicator 201, an ultrasound-generating device, such as an ultrasound transducer 202, and preferably an information sending and receiving unit 203. The drug applicator 201 comprises at least one space 800 to hold the drug. The term ultrasound transducer 202 is including any hardware to produce an ultrasound signal.

In an embodiment of the invention, the drug applicator 201 is formed from a low ultrasound attenuation material. The low ultrasound attenuation material can be at least one selected from the following list: epoxy resin, polyurethane rubber, polycarbonate, nylon 6-6, polyvinyl chloride, polyester, ultra-high molecular weight polyethylene, polypropylene, Teflon, polystyrene, neoprene rubber, polyvinyl alcohol, polydimethylsiloxane, silicone-containing rubber, silicon hydrogel, silicone rubber. Additionally or alternatively the drug applicator 201 can be formed from a silicon rubber doped with at least one of the following materials: nickel, silver, palladium, tungsten, gold, platinum, silicon oxide, titanium oxide, aluminum oxide, barium sulphate, iron oxide, zirconium dioxide, cerium oxide, bismuth oxide, ytterbium oxide, lutetium oxide, hafnium oxide.

The drug applicator may be formed from or may comprise a low ultrasound attenuation material having an ultrasound attenuation less than or equal to about 20, 15, 12, 10, 9, 8, 7, 6, 5, 4, 3, 2, 1, 0.5, or 0.1 dB/(MHz cm). The drug applicator may have an ultrasound attenuation greater than any of the values provided, or falling within a range between any two of the values provided. The low ultrasound attenuation may advantageously facilitate transport of ultrasound from the ultrasound-generating device to the drug applicator, and may eventually reach the target site. If the attenuation is too high, energy may be lost in the ultrasound transmission process, and acoustic output at the delivery site may be lower, which may impede the drug delivery process, or make the drug delivery process less effective.

The drug applicator 201 may be configured to be coupled with a surface of an eye. In an embodiment of the invention, the drug applicator 201 is configured to be coupled to the scleral surface with a low ultrasound loss at a surface 601b directed towards the eye 100. In some embodiments, the drug applicator may be configured to be coupled to a corneal surface. Any description herein of a scleral surface of the eye, may apply to any other portion of a surface of an eye, such as a corneal surface of the eye. In some embodiments, to enhance ultrasound coupling a substance may be applied to the surface 601b and/or the scleral surface of the eye 100. The substance is filling an optional gap 601a between the drug applicator 201 and the scleral surface of the eye 100. The substance can be, for example, an ultrasound coupling agent. The substance may have a gel or liquid form. An ultrasound coupling agent may have an acoustic impedance that is intermediate between a drug applicator and a surface of the eye (e.g., scleral surface, cornea surface, etc.). The acoustic impedance of the ultrasound coupling agent may fall between an acoustic impedance value of the drug applicator and an acoustic impedance value of the surface of the eye where the ultrasound coupling agent is configured to come into contact.

In an embodiment of the invention, coupling of the drug applicator 201 to a surface of the eye, such as the scleral surface, can be improved by the design of the drug applicator 201. The drug applicator 201 may be formed from an elastic material having a Young's modulus of less than 10 GPa. The drug applicator may be formed from an elastic material having a Young's modulus of less than or equal to 20 GPa, 15 GPa, 12 GPa, 10 GPa, 9 GPa, 8 GPa, 7 GPa, 6 GPa, 5 GPa, 4 GPa, 3 GPa, 2 GPa, 1.5 GPa, 1 GPa, 0.5 GPa, or 0.1 GPa. In some instances, the drug applicator may have a Young's modulus greater than any of the values provided, or falling between any two of the values provided. When the drug applicator 201 is made from a sufficiently elastic material, the drug applicator can be pressed against the eye 100 and, upon exerting a pressure, the drug applicator 201 will deform and adapt to the specific form of an individual eye 100. The pressure can be evenly distributed on the scleral surface and the user experience is improved. In some embodiments, a pressure variation over the sclera surface where the drug applicator contacts the eye may be less than 5 MPa, 4 MPa, 3 MPa, 2 MPa, 1 MPa, 500 kPa, 300 kPa, 200 kPa, 100 kPa, 50 kPa, 30 kPa, 20 kPa, 15 kpa, 10 kPa, 7 kPa, 5 kPa, 3 kPa, 2 kPa, 1 kPa, 0.5 kPa, 0.1 kPz, 0.05 kPa, or 0.01 kPa. In addition, the gap 601*a* between the scleral surface and the drug applicator 201 is minimized and the ultrasound coupling is improved.

In some embodiments, the drug applicator may directly contact the surface of the eye. The drug applicator may contact the surface of the eye without requiring an intermediary device or substance. In some embodiments, to enhance the contact between the drug applicator and the surface of the eye, the drug applicator may be shaped or formed to provide a large contact area with the surface of the eye. For instance, the drug applicator may be shaped or formed to have at least a $0.1$ mm$^2$, $0.5$ mm$^2$, $1$ mm$^2$, $1.5$ mm$^2$, $2$ mm$^2$, $3$ mm$^2$, $5$ mm$^2$, $7$ mm$^2$, $10$ mm$^2$, $15$ mm$^2$, $20$ mm$^2$, $30$ mm$^2$, $40$ mm$^2$, $50$ mm$^2$, $75$ mm$^2$, $1$ cm$^2$, $1.5$ cm$^2$, $2$ cm$^2$, or $3$ cm$^2$ area of contact between the drug applicator and a surface of the eye, such as the sclera of the eye.

It is an advantage of the present invention over the prior art, that the delivery performance is not influenced by the stand-off distance d of the drug applicator 201. Therefore, deformation of the drug applicator 201 is possible, without compromising the drug delivery performance.

In an embodiment of the invention, the drug applicator 201 is configured to be mechanically coupled to the drug delivery system. In an embodiment, the drug applicator 201 is configured to be coupled to the ultrasound transducer 202. The coupling may comprise a mechanical coupling and may hold the drug applicator 201 in a fixed position relative to the ultrasound transducer 202, preferably in a fixed position at the ultrasound transducer 202. The coupling may further comprise a low loss ultrasound coupling of the drug applicator 201 to the ultrasound transducer 202. The low loss ultrasound coupling is preferably improved by using a substance at an interface 602 between the drug applicator 201 and the ultrasound transducer 202. The substance is preferably an ultrasound coupling agent. The mechanical coupling preferably is a releasable mechanical coupling that is designed for coupling different drug applicators 201 to the ultrasound transducer 202. The different drug applicators 201 preferably have a different size and/or a different form factor. Further examples of couplings between the drug applicator and the ultrasound transducer are provided in greater detail elsewhere herein.

Any description herein of an ultrasound transducer 202 may apply to any type of ultrasound-generating device, and vice versa. The ultrasound transducer may be based on a design of flexural mode of vibration. A flexural transducer may advantageously produce a desired ultrasound frequency and/or intensity with a relatively low excitation voltage, low weight, and/or small size. In alternative embodiments, a stacked ceramic design of ultrasound transducer may be used.

The ultrasound transducer may produce any frequency of ultrasound. For instance, the ultrasound transducer may produce a frequency of less than or equal to about 1 kHz, 5 kHz, 10 kHz, 20 kHz, 25 kHz, 30 kHz, 35 kHz, 37 kHz, 39 kHz, 40 kHz, 41 kHz, 43 kHz, 45 kHz, 50 kHz, 55 kHz, 60 kHz, 65 kHz, 70 kHz, 80 kHz, 90 kHz, 100 kHz, 120 kHz, 150 kHz, 200 kHz, 300 kHz, 400 kHz, 500 kHz, 600 kHz, 700 kHz, 800 kHz, 900 kHz, 1 MHZ, 1.5 MHz, 2 MHZ, 3

MHZ, or 5 MHz. The ultrasound transducer may produce a frequency greater than any of the frequency values provided herein, or falling within a range between any two of the values provided herein.

The ultrasound transducer may produce any ultrasound intensity. For instance, the ultrasound transducer may produce an intensity of less than or equal to about 0.001, 0.005, 0.01, 0.03, 0.05, 0.07, 0.1, 0.11, 0.12 0.13, 0.14, 0.15, 0.17, 0.2, 0.25, 0.3, 0.35, 0.4, 0.5, 0.6, 0.7, 0.8, 0.9, 1, 1.2, 1.5, 2, 2.5, 3, 5, or 10 W/cm$^2$. The ultrasound transducer may produce an intensity greater than any of the intensity values provided herein, or falling within a range between any two of the values provided herein.

In some embodiments, the ultrasound transducer may have an excitation voltage of less than about 0.1, 0.5, 1, 3, 5, 10, 15, 20, 22, 25, 27, 30, 33, 35, 40, 45, 50, 60, 70, 80, 90, 100, 120, 150, 200, 300, 500 $V_{RMS}$. The excitation voltage may be less than any of these values while allowing the ultrasound transducer to operate at a frequency value as provided herein, or an intensity value as provided herein. In some embodiments, the excitation voltage may be greater than any of the values provided herein, or within a range falling between any two of the values provided herein.

The ultrasound transducer may be of a low weight. For instance, the ultrasound transducer may weigh less than 1 g, 5 g, 10 g, 20 g, 30 g, 40 g, 50 g, 60 g, 70 g, 80 g, 90 g, 100 g, 110 g, 120 g, 130 g, 150 g, 170 g, 200 g, 225 g, 250 g, 300 g, 350 g, 400 g, 500 g, 600 g, 700 g, 800 g, 1 kg, 2, kg, 3 kg, or 5 kg. The ultrasound may weigh less than any of these values while allowing the ultrasound transducer to operate a frequency value as provided herein, or an intensity value as provided herein. In some embodiments, the weight may be greater than any of the values provided herein, or within a range falling between any two of the values provided herein.

The ultrasound transducer may be of a small size. For instance, the ultrasound transducer may have a maximum dimension (e.g., length, width, height, diagonal, or diameter) of less than 1 mm, 3 mm, 5 mm, 7 mm, 10 mm, 12 mm, 15 mm, 17 mm, 20 mm, 22 mm, 25 mm, 27 mm, 30 mm, 35 mm, 40 mm, 45 mm, 50 mm, 60 mm, 70 mm, 80 mm, 90 mm, 100 mm, 120 mm, 150 mm, 175 mm, 200 mm, 250 mm, or 300 mm. The ultrasound may have a maximum dimension less than any of these values while allowing the ultrasound transducer to operate a frequency value as provided herein, or an intensity value as provided herein. In some embodiments, the maximum dimension may be greater than any of the values provided herein, or within a range falling between any two of the values provided herein.

In some embodiments, the ultrasound transducer may have a volume of less than 0.1 cm$^3$, 0.5 cm$^3$, 1 cm$^3$, 1.5 cm$^3$, 2 cm$^3$, 2.5 cm$^3$, 3 cm$^3$, 4 cm$^3$, 5 cm$^3$, 6 cm$^3$, 7 cm$^3$, 8 cm$^3$, 9 cm$^3$, 10 cm$^3$, 12 cm$^3$, 15 cm$^3$, 17 cm$^3$, 20 cm$^3$, 25 cm$^3$, 30 cm$^3$, 35 cm$^3$, 40 cm$^3$, 50 cm$^3$, 70 cm$^3$, 100 cm$^3$, 120 cm$^3$, 150 cm$^3$, 200 cm$^3$, 250 cm$^3$, 300 cm$^3$, 400 cm$^3$, 500 cm$^3$, 750 cm$^3$, or 1000 cm$^3$. The ultrasound may have volume less than any of these values while allowing the ultrasound transducer to operate a frequency value as provided herein, or an intensity value as provided herein. In some embodiments, the volume may be greater than any of the values provided herein, or within a range falling between any two of the values provided herein.

Providing an ultrasound transducer with any of these characteristics may advantageously permit the ultrasound transducer to be used in medical applications for the eye and other soft tissue. The compact size and/or weight may allow the ultrasound transducer to be used on a portable drug delivery device.

The ultrasound transducer may have any form factor. In some instances, the ultrasound transducer may have a form factor that may fit to a drug applicator. The ultrasound transducer may have a form factor that may allow the drug applicator to fit to the ultrasound transducer at an interface. An interface can be indirect contact with the drug applicator, or within a distance where the interface can be in contact with air, gas, water, gel, or other low ultrasound attenuation materials to prevent a reduction of the ultrasound. In some examples, the ultrasound transducer may have a triangle, square, round, ring shape, or other shape (such as those provided elsewhere herein) form factor at the interface. The interface of the ultrasound transducer can be formed of a single or multiple ultrasound transducers, which can be adjusted as necessary to achieve a desired shape. In some instances, the desired shape may include a circle or any other shape, as provided elsewhere herein. The desired shape may have an interior space. The interior space may be provided in the middle.

The interior space may allow for combinations of the ultrasound transducer with additional features. For instance, the added features in the interior space could be coupled with the ultrasound transducer 202 at an interface 202*c* inside the transducer to connect them to energy, control, or data transfer. Added features 202*c-e* can comprise an emitting device, such as a wavelength emitting device 202*c* such as an LED lamp, UV lamp, or light bulb, a wavelength recording device, such as a camera 202*d* or microphone 202*e*. Added features may be used in combination with a lens 202*f*, which may adjust wavelengths. For instance, emitted wavelengths may be adjusted (e.g., focused, condensed, diffracted, filtered, reflected, split, etc.). Measured wavelengths can also be adjusted (e.g., magnified, focused, diffracted, filtered, reflected, split, etc.). The added features to the ultrasound transducer can be used for a variety of applications, such as causing chemical reactions such as UV cross-linking, and/or target site illumination plus video recording with a camera as described in greater detail elsewhere herein. This may allow a practitioner to examiner an eye prior to, during, and/or after treatment, for instance cornea crosslink (CXL) through UV light or VEGF drug delivery treating diabetic retinopathy or macular degenerations.

In an embodiment of the invention, the information sending and/or receiving unit 203 is arranged and configured such that the information sending and/or receiving unit 203 can retrieve information about the drug applicator 201 and/or the drug when the drug applicator is coupled to the application head. In order to be able to identify the drug applicator 201, the information sending and/or receiving unit 203 comprises reading means configured to read information related to the drug applicator 201. The reading means preferably include a reader for a human- or machine-readable label and/or an RFID label.

Figure 3:
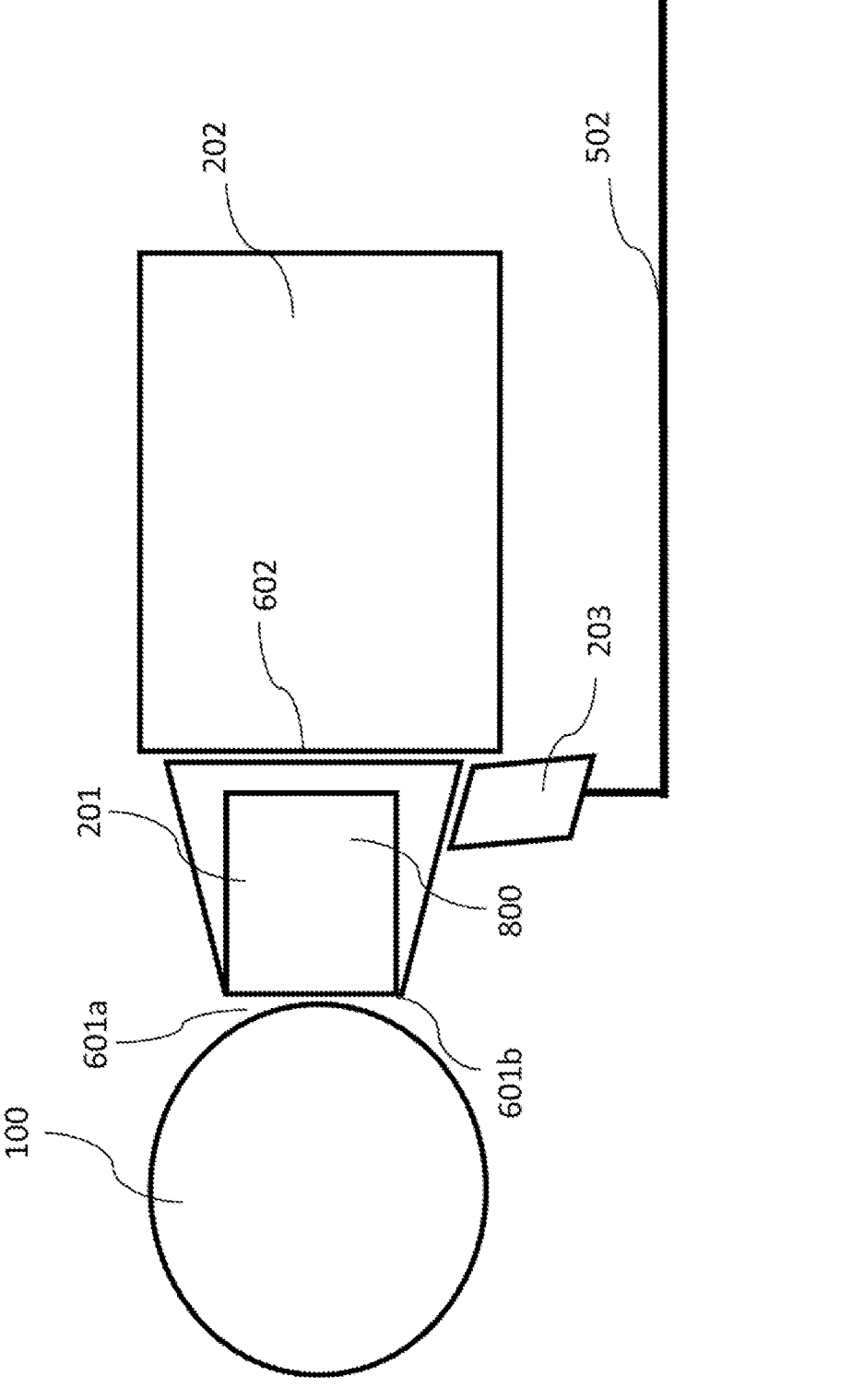
FIG. 3 shows an additional example of an embodiment of the delivery unit.

FIG. 3 shows an additional example of an embodiment of the delivery unit, in accordance with an embodiment of the invention. A delivery unit 200 may comprise a drug applicator 201, and an ultrasound-generating device, such as an ultrasound transducer 202, The delivery unit may also comprise an information sending and receiving unit 203. The drug applicator 201 comprises at least one space 800 to hold the drug. The delivery unit may be configured to come into contact with an eye 100. A surface 601*b* of the drug delivery unit may be configured to face the eye and/or deliver ultrasound to the eye. The surface may optionally be configured to deliver drugs to the eye. A gap 601*a* may or may not be provided between the eye-facing surface 601*b* of the delivery unit and a surface of the eye, such as the sclera or cornea.

The drug applicator 201 may or may not be removable from the ultrasound-generating device 202. The drug applicator may have any type of shape for a desired application. In some embodiments, different drug applicators with different form factors may be swapped in and out. Different drug applicators with different characteristics (e.g., size, shape, material, elasticity, holding different drugs, attenuation properties) may be exchanged for one another. For example, a first drug applicator having a first set of characteristics may be coupled to the ultrasound-generating device. The first drug applicator may be removed. A second drug applicator having a second set of characteristics may be coupled to the ultrasound-generating device. The first set and second set of characteristics may be different from one another. The first set and second set of characteristics may or may not share one or more of the same characteristics.

An information sending and/or receiving unit 203 may be operably coupled to the drug applicator and/or the ultrasound-generating device. The information sending and/or receiving unit may receive information about the drug applicator. The information sending and/or receiving unit may be able to sense, with aid of one or more sensors, when a drug applicator is coupled to the ultrasound-generating device and/or when a drug applicator is not coupled to the ultrasound-generating device. The presence and/or absence of a drug applicator may be detected. The information sending and/or receiving unit may be able to detect information about a drug applicator coupled to the ultrasound-generating device. The information may include type of drug applicator, one or more characteristics of the drug applicator, and/or an identifier or other information about the specific drug applicator (e.g., serial number, batch number, drug name, date of manufacture, etc.).

The information sending and/or receiving unit may include a sensor that may capture information about a presence and/or absence of the drug applicator, or that may be able to collect information about the drug applicator (e.g., read a label of the drug applicator, measure a characteristic of the drug applicator, receive information emitted by the drug applicator). Examples of sensor types may include vision sensors (e.g., imaging devices capable of detecting visible, infrared, or ultraviolet light, such as cameras), proximity sensors (e.g., ultrasonic sensors, lidar, time-of-movement cameras), inertial sensors (e.g., accelerometers, gyroscopes, inertial measurement units (IMUs)), pressure sensors (e.g., barometers), audio sensors (e.g., microphones) or field sensors (e.g., magnetometers, electromagnetic sensors). Any suitable number and combination of sensors can be used, such as one, two, three, four, five, or more sensors. Optionally, the data can be received from sensors of different types (e.g., two, three, four, five, or more types). Sensors of different types may measure different types of signals or information (e.g., images, sounds, signals, position, proximity, pressure, etc.) and/or utilize different types of measurement techniques to obtain data. For instance, the sensors may include any suitable combination of active sensors (e.g., sensors that generate and measure energy from their own source) and passive sensors (e.g., sensors that detect available energy). In some embodiments, multiple types of sensors may be used to detect information regarding the drug applicator. In one example, an optical sensor may read a visual marker on-board the drug applicator. Examples of visual markers may include labels, words, numbers, characters, shapes, symbols, icons, barcodes, QR codes, a sequence of one or more flashing lights, or any other type of visual marker. In another example, the drug applicator may be an RFID reader that may read RFID information from the drug applicator. In another example, the drug applicator may comprise an infrared reader that may read infrared information being emitted by the drug applicator. In some embodiments, the information sending and/or receiving unit may comprise a communication unit that may receive information from a separate sensor or from the drug applicator.

Additionally or alternatively to capturing information about the drug applicator, the information sending and/or receiving unit may capture information relating to the ultrasound-generating device. The information sending and/or receiving unit (and any sensors thereof) may be located in close proximity to the drug applicator and/or the ultrasound transducer. The information sending and/or receiving unit may aid in measurement and regulation of input cycle information. Information regarding a specific ultrasound cycle such as, but not limited to, single cycle time, cycle repetition, ultrasound intensity, ultrasound frequency and potential additional features may be sent from a signal generating unit 300. Information may be sent to the ultrasound generating device 202 from a signal amplifier 301 through a communication link 501. The information sending and/or receiving unit 203 may measure the ultrasound-generating device 202 output and send information back to the controller 302 which may back regulate the signal generator and/or amplifier 301. Next to the general regulation of the ultrasound output and input, the information sending and/or receiving unit 203 can comprise a sensor, such as any sensor as previously described. For instance, one or more sensors may measure temperature, ultrasound frequency and/or intensity. Additional sensors and/or device may comprise a camera, electrode, tonometer, timer, scanning device, or lamp. The signal generator and/or amplifier 301 may receive signals from any of the sensors and/or devices. The signal generator and/or amplifier 301 may send information to the signal generating unit 300 and/or the display and control unit 400, where parameters may be read and adjusted.

The information sending and/or receiving unit may or may not comprise one or more processors on-board the unit. The information sending and/or receiving unit may or may not process information gathered by the sensors. The information sending and/or receiving unit may determine the presence or absence of a drug applicator and/or information about the drug applicator. The information sending and/or receiving unit may or may not send raw or formatted data to another portion of the drug delivery device to be processed.

The information sending and/or receiving unit may be located anywhere on the drug delivery unit. In some embodiments, the information sending and/or receiving unit may be located on or near an ultrasound-generating device. The information sending and/or receiving unit may be located on or near an interface of the ultrasound-generating device configured to couple with the drug applicator. The information sending and/or receiving unit may be located on or at a side of the ultrasound-generating device configured to couple with the drug applicator. The information sending and/or receiving unit may be located on or in a surface of the ultrasound-generating device. An information sending and/or receiving unit may be embedded in the ultrasound-generating device. The information sending and/or receiving unit or a portion thereof may or may not be provided on the drug applicator.

The information sending and/or receiving unit 203 may be operably coupled with a communication link 502. The communication link may be a wired or wireless communication mechanism. The sending and/or receiving unit may send information about the drug applicator, which may include the presence or absence of the drug applicator, to another portion of the drug delivery device, via the communication the link. The information sending and/or receiving unit may or may not receive information via the communication link. In some embodiments, instructions may be sent to the information sending and/or receiving unit that may affect operation of the information sending and/or receiving unit.

Figures 4A, 4B, 4C:
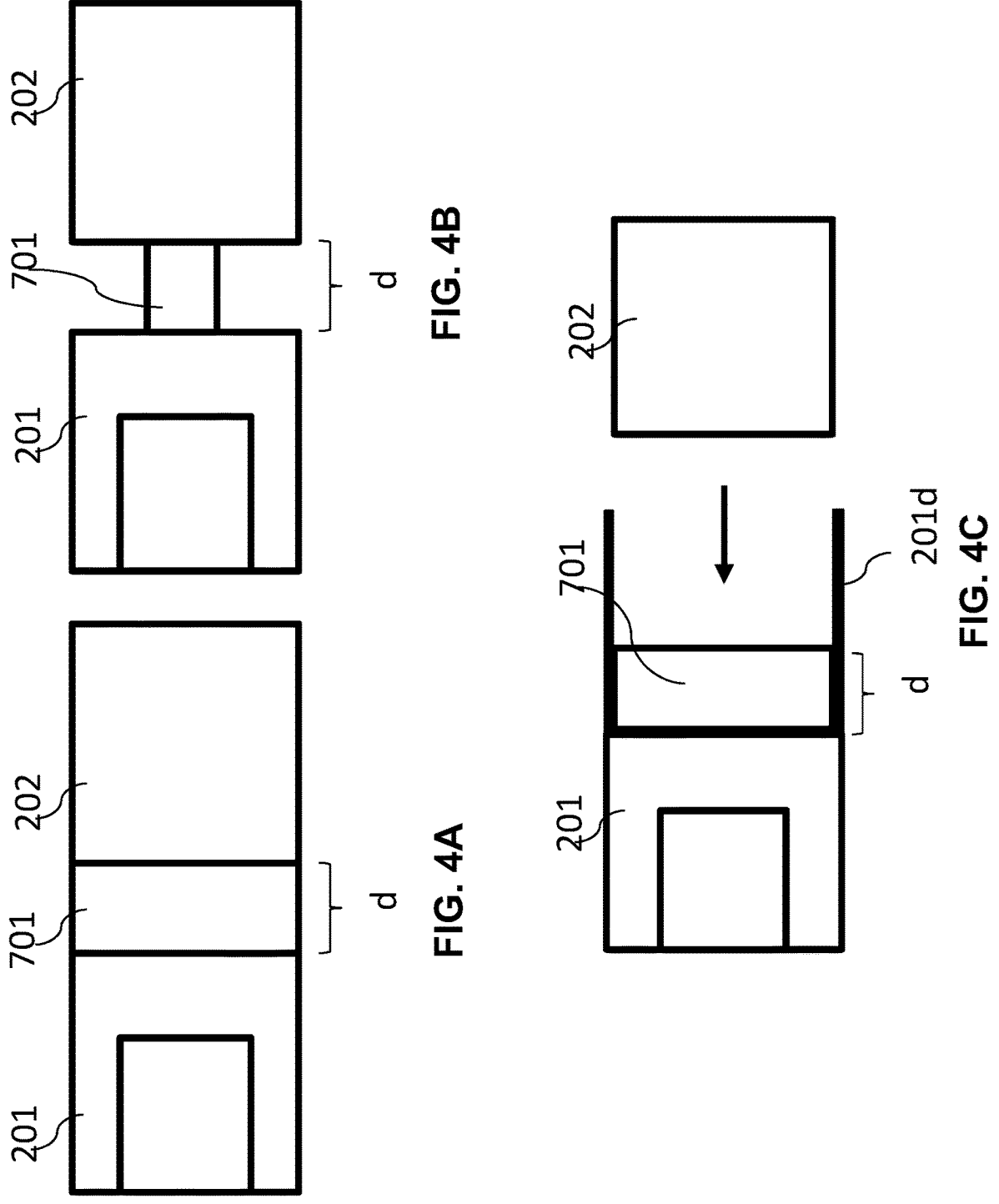
FIGS. 4A to 4C show examples of a coupling between a drug applicator and an ultrasound-generating device.

FIGS. 4A to 4C show schematic examples of a coupling 701 between a drug applicator 201 and an ultrasound-generating device 202, in accordance with embodiments, of the invention. The drug applicator may be coupled to the ultrasound-generating device prior to operation of the drug delivery device. The coupling may be an interface between the drug applicator and ultrasound-generating device. For instance, the drug applicator may directly contact the ultrasound-generating device via the interface, which may be the coupling. In other instances, the coupling may be an intermediary component. The drug applicator may contact the ultrasound generating device via the intermediary component.

The coupling may have any form or configuration between the ultrasound-generating device and the drug applicator. The schematics are provided to show a relationship between the ultrasound-generating device and the drug applicator, and coupling illustrated therein is not limited to the depictions provided. The ultrasound-generating device is operably coupled to the drug applicator via the coupling.

FIG. 4A shows a schematic example of a coupling 701 between a drug applicator 201 and an ultrasound-generating device 202. In some instances, the coupling may have a large surface area contact with the ultrasound-generating device and/or the drug applicator. For instance, the surface area contact may be maximized. For instance, the coupling may have a cross-sectional area greater than or equal to the cross-sectional area of the ultrasound-generating device, and/or the surface area of the drug applicator. The coupling may have a surface area that matches or is greater than the surface area of the ultrasound-generating device that comes into contact with the coupling, and/or the surface area of the drug applicator that comes into contact with the coupling. An increased surface area may allow the ultrasound signals from the ultrasound-generating device to be delivered to drug applicator in an increased manner. This may be desirable when less attenuation from the ultrasound-generating device to the drug applicator and/or the surface of the eye is desired.

FIG. 4B shows an additional schematic example of a coupling 701 between a drug applicator 201 and an ultrasound-generating device 202. In some instances, the coupling may have a smaller surface area contact with the ultrasound-generating device and/or the drug applicator. For instance, the surface area contact may be less than a total surface of the ultrasound-generating device and/or drug applicator. For instance, the coupling may have a cross-sectional area less than or equal to the cross-sectional area of the ultrasound-generating device, and/or the surface area of the drug applicator. The coupling may have a surface area that matches or is less than than the surface area of the ultrasound-generating device that comes into contact with the coupling, and/or the surface area of the drug applicator that comes into contact with the coupling. A decreased surface area may allow the ultrasound signals from the ultrasound-generating device to be delivered to drug applicator in a controlled manner. In some embodiments, the dimensions of the coupling mechanism may be selected to allow for a desired degree of ultrasound-attenuation. In some instances, the coupling mechanism may be selected to provide a desired form factor of the device. The desired form factor may depend on a design to permit the drug applicator to be attached or detached from the ultrasound-generating device in an easy and repeatable manner.

FIG. 4C shows a schematic example of a coupling 701 between a drug applicator 201 and an ultrasound-generating device 202. In some instances, the ultrasound-generating device may be coupled to a drug applicator by being inserted into a casing 201$d$ of the drug applicator. The coupling may be provided within the casing of the drug applicator. For instance, the surface area contact may or may not be maximized. In some embodiments, a drug applicator may be inserted into a casing of the ultrasound-generating device. The coupling may be provided within the casing of the ultrasound-generating device.

The coupling may be formed of or may comprise a coupling medium. A coupling medium may be provided in an interface between the drug applicator and the ultrasound transducer. The coupling medium may be in a solid, liquid, suspension, and/or gel form. The coupling may be formed from a rigid, semi-rigid, or elastic material. The coupling medium may be formed from a low attenuation material.

The coupling medium may have a thickness d. The thickness may be equal to a multiple of λ, where λ is a wavelength. The thickness may be a multiple of λ/4. The thickness may be an odd multiple of λ/4. An odd multiple may be an odd whole number (e.g., 1, 3, 5, 7, . . . ). This may improve or optimize impedance matching of the ultrasound-generating device (e.g., ultrasound transducer) and the drug applicator, thus allowing the ultrasound waves to transmit from the transducer to the target site.

The wavelength 2, may be calculated by the following: 2=c/fr where c is the propagation speed in the coupling medium, and fr is the resonance frequency. The propagation speed c may depend on the material type of the coupling medium. The propagation speed may depend on one or more physical characteristics of the coupling medium. For instance, the propagation speed may depend on elastic properties, density, or temperature of the coupling medium. Thus, the thickness of the coupling medium may be proportional to the wavelength. The thickness of the coupling medium may be directly proportional to the wavelength. The thickness of the coupling may be linearly proportion.al to the wavelength. The thickness of the coupling may be proportional (e.g., directly proportional, linearly proportional) to the propagation speed. The thickness may be proportional to the resonance frequency. The thickness may be inversely proportional to the resonance frequency. The thickness may be linearly inversely proportional to the resonance frequency.

An interface between the drug applicator and the ultrasound-generating device may comprise a coupling medium having a thickness that is a multiple of a propagation speed of the coupling medium over the resonance frequency of the coupling medium. The coupling medium may have a thickness that is an odd multiple of a propagation speed of the coupling medium over four times a resonance frequency.

In some embodiments, the stand-off distance between the drug applicator and the ultrasound-generating device may depend on the thickness as described. The stand-off distance between the drug applicator and the ultrasound-generating device may depend on a design of a casing of the drug applicator. Alternatively or in addition, the stand-off distance between the drug applicator and the ultrasound-generating device may depend on a design of a casing of the ultrasound-generating device. The stand-off distance may depend on a thickness of any component that may connect the drug applicator and the ultrasound-generating device.

A coupling between the drug applicator and the ultrasound-generating device may occur by hand. Manual attachment and/or detachment may occur between the drug applicator and the ultrasound-generating device. The coupling may require use of two hands, or may be completed using only a single hand. A coupling between the drug applicator and the ultrasound-generating device may be effectuated without use of a tool. The coupling between the drug applicator and the ultrasound-generating device may comprise a simple release mechanism (e.g., quick-release mechanism). The simple release mechanism may comprise less than or equal to one, two, three, four, five, or six motions by hand. Examples of a single motion by hand may comprise a twist, pull, push, movement of a lever, depression of a button, a flip of a switch, or any other simple motions. Each of the motions may be in a single direction (e.g., axial direction, lateral direction, vertical direction, rotational direction, etc.). One or more, or all of the motions may be executed manually without use of a tool. The user may not need to exert any excessive force in performing any of the motions. Easy manual attachment and detachment between the drug applicator and ultrasound-generating device may permit the use of the disposable drug applicators by a drug delivery device.

The various drug applicators can be swapped in and out as needed. The drug applicators can be easily attached for use with the drug delivery device, and then detached when the drug applicator is used and no longer needed. This may also advantageously allow for using different types of drug applicators with the same drug delivery device.

Figures 5A, 5B:
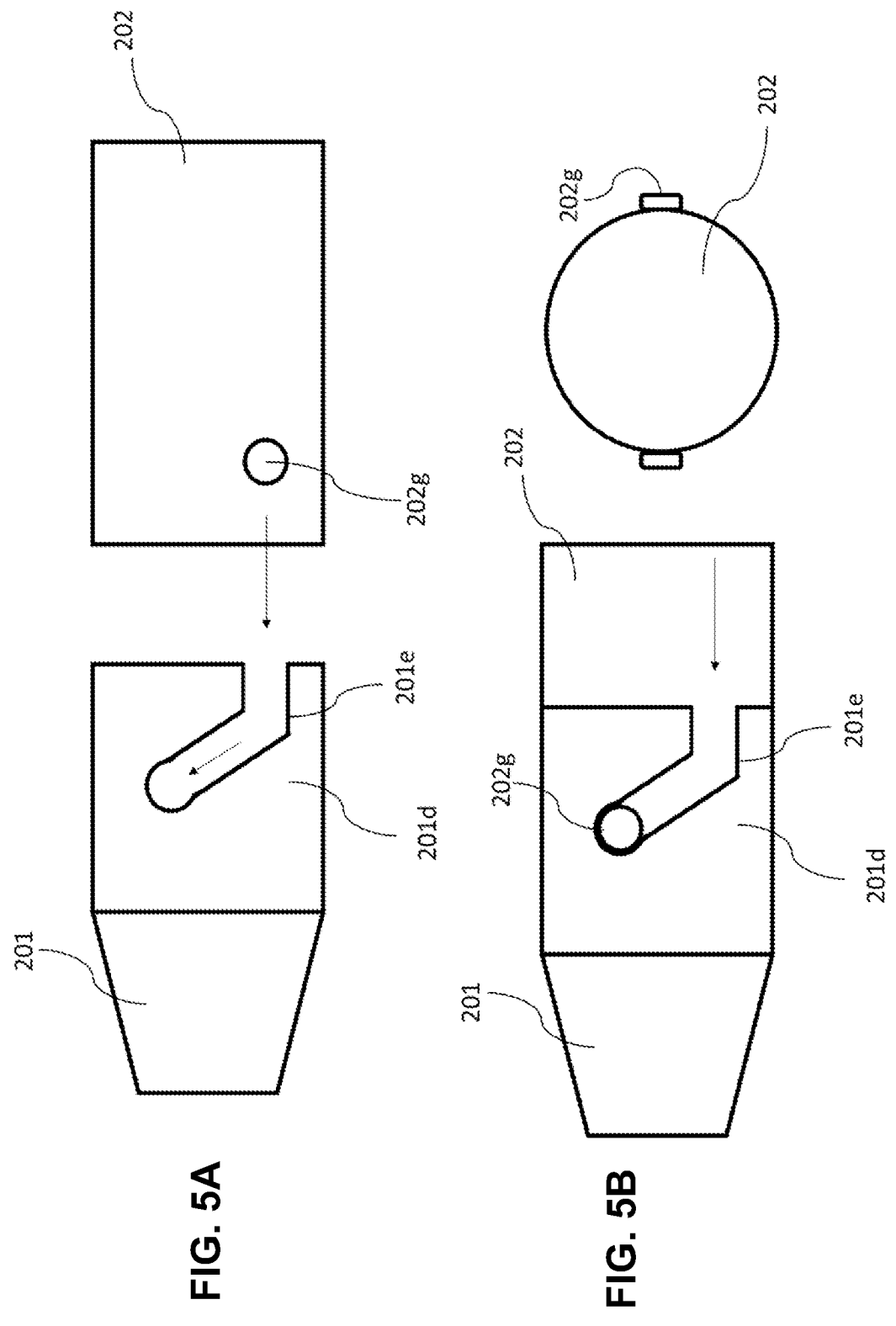
FIGS. 5A to 5B show examples of how a drug applicator and an ultrasound-generating device may be coupled to one another.

FIGS. 5A to 5B show examples of how a drug applicator and an ultrasound-generating device may be coupled to one another. In one example, at least one of the drug applicator or the ultrasound-generating device may be at least partially inserted into the other. A drug applicator case ben at least partially inserted into the ultrasound-generating device, or vice versa.

For instance, a drug applicator 201 may comprise a drug applicator case 201$d$. The drug applicator may couple with the ultrasound-generating device 202. The ultrasound-generating device may be at least partially inserted into the drug applicator case.

The ultrasound-generating device may comprise one or more pins 202$g$. The pins may protrude from an exterior surface of the ultrasound-generating device. The pins may be positioned so that they can click in a case lock 201$e$ of the drug applicator case 201$d$. In some embodiments, the case lock may comprise one or more slots, cut-outs, grooves, or other mechanisms that may receive the pins. The case lock may have a shape that may allow the pins to lock into the case lock. The case lock may guide the pins along at least two different directions. The case lock may terminate at a circle or hook that may aid in keeping the ultrasound-generating device and the drug applicator together. Any description herein of pins may apply to any protruding portions that may be accepted into the case lock of the drug applicator case. In other embodiments, the reverse may be provided wherein the ultrasound-generating device may comprise one or more slots, cut-outs, grooves or other mechanisms that may receive protruding portions, such as pins, from the drug applicator case. In some embodiments, the pins from the drug applicator case may be formed on an interior surface of the drug applicator case, so they may form the case lock of the ultrasound generating device when the ultrasound generating device is inserted into the drug applicator case.

In another example, an ultrasound-generating device 202 may comprise an ultrasound-generating device case. The ultrasound-generating device may couple with a drug applicator. The drug applicator may be at least partially inserted into the ultrasound-generating device case.

The drug applicator may comprise one or more pins. The pins may protrude from an exterior surface of the drug applicator. The pins may be positioned so that they can click in a case lock of the ultrasound-generating device. In some embodiments, the case lock may comprise one or more slots, cut-outs, grooves, or other mechanisms that may receive the pins. The case lock may have a shape that may allow the pins to lock into the case lock. The case lock may guide the pins along at least two different directions. The case lock may terminate at a circle or hook that may aid in keeping the ultrasound-generating device and the drug applicator together. Any description herein of pins may apply to any protruding portions that may be accepted into the case lock of the ultrasound-generating device case. In other embodiments, the reverse may be provided wherein the drug applicator may comprise one or more slots, cut-outs, grooves or other mechanisms that may receive protruding portions, such as pins, from the ultrasound-generating device case. In some embodiments, the pins from the ultrasound-generating device case may be formed on an interior surface of the ultrasound-generating device case, so they may form the case lock of the drug applicator when the drug applicator is inserted into the ultrasound-generating device case.

Alternatively or in addition, the interface of an ultrasound-generating device may comprise a first fastener configured to mate with a second fastener on-board the drug applicator. The first fastener and the second fastener may be configured to be screwed together. The ultrasound-generating device or the drug applicator may be screwed inside one another. In one example, the ultrasound-generating device or the drug applicator may be screwed inside the other through a case lock (e.g., of a drug applicator case or of an ultrasound-generating device case) and a pin (e.g., of an ultrasound-generating device or a drug applicator). The screwing together may permit direct or close contact between the drug applicator and the ultrasound-generating device. In some embodiments, the first fastener and the second fastener may be configured to snap together. Any interlocking mechanism or snap-fit mechanism may be employed to connect the ultrasound-generating device and the drug applicator. A case lock and/or pin may or may not be employed with the snapping mechanism. The mating between the first and second fasteners may or may not include a rotational component. The rotational component may include rotation about an axis extending along a length of the drug applicator and/or a length of the ultrasound-generating device. Axial rotation may occur about an axis extending through both the drug applicator and the ultrasound-generating device.

In some embodiments, an additional interface 602 may have a direct contact between the drug applicator 201 and the ultrasound-generating device 202, or may be filled with ultrasound-attenuation material such as, but not limited to, air, water, gel, and/or hydrogel to prevent any reduction of ultrasound intensity and to facilitate ultrasound transfer to the drug applicator. Improved ultrasound transfer to the drug applicator may result in improved ultrasound transfer to a delivery site 100.

A drug applicator and an ultrasound-generating device may snap together. In some embodiments, the drug applicator may snap onto the ultrasound-generating device or vice versa. They may snap together with aid of mechanical features. Various shapes may be provided that may aid in snapping together, such as interlocking or mating shapes. In some embodiments, magnets may aid in the coupling between the drug applicator and the ultrasound-generating device. In one example, a magnet may be placed on an ultrasound-generating device with a suitable metal or alloy on-board the drug applicator. Alternatively or in addition, a magnet may be placed on a drug applicator with a suitable metal or alloy on-board the ultrasound-generating device. This may allow the ultrasound-generating device and the drug applicator to be held together with aid of a magnetic force. This may be provided alternatively or in addition to any other connecting mechanism described elsewhere herein. This may be provided alternatively or in addition to any sorts of locks, screws, clips, or adhesives that may aid in coupling the drug applicator to the ultrasound-generating device.

A variety of coupling mechanisms may be provided between a drug applicator and an ultrasound-generating device. As previously described, the mechanisms may allow for manual coupling and decoupling between the drug applicator and the ultrasound-generating device. The coupling may allow for repeatable coupling and decoupling between the drug applicator and the ultrasound-generating device. The coupling may allow for low ultrasound attenuation from the ultrasound-generating device to the drug applicator. The coupling may allow for low ultrasound attenuation from the ultrasound-generating device to a delivery site. Low ultrasound attenuation may have any values or characteristics, as described elsewhere herein.

A drug applicator may be loaded with one or more drugs. The drug applicator may store the drugs in any manner within or on the drug applicator.

For instance, drugs may be provided on a surface of the drug applicator. In some embodiments, an entirety of the surface of the drug applicator may be coated with the drugs. In some embodiments, only a portion of the surface of the drug applicator may be coated with the drugs. For instance, a portion of the surface of the drug applicator that is configured to come into contact with a surface of the eye may be coated with the drug. An interface 601*a* between a delivery site on the eye and the drug applicator can be filled with reagents or material that may improve drug delivery to the targeted site. This may occur by coating the drug and/or reagents on the surface of the drug applicator. Alternatively or in addition, the interface may be filled with the drug itself, for delivery to the delivery site on the eye. In some embodiments, the reagents or materials that may improve drug delivery to the target site may comprise microspheres, micelles, nanoparticles, proteins, molecules, or chemicals that may be adsorbed or absorbed on its surface. The reagents may comprise any reagents as described elsewhere herein.

In another example, drugs may be incorporated into a porous material. For instance, the drugs may be soaked, encapsulated, adhered, or adsorbed on porous material. Examples of porous materials my include, but are not limited to, sponges, or polymer matrixes. Porous materials may have a porosity of at least 3%, 5%, 10%, 20%, 30%, 40%, 50%, 60%, 70%, 80%, 90%, 95%, 97%, or 99%. The porous materials may have a porosity less than any of the values provided, or falling within a range between any two of the values provided. The drugs may be provided within the pores of the porous materials.

Drugs may be enclosed in a compartment within the drug applicator. The drugs may be completely enclosed within the compartment. A seal or cover may be removed to provide access to the drugs during use on a subject. In some embodiments, application of ultrasound may allow the drugs to pass through a wall or portion of the drug applicator to be delivered to a delivery site of on an eye of a subject.

In some embodiments, the drugs may be provided within a compartment of the drug applicator that has an open or sealed end. The sealed end may be removed, ruptured, or pierced during use on a subject.

A drug applicator may have a single type of drug loaded thereon. Alternatively, the drug applicator may have multiple types of drugs loaded thereon. The multiple types of drugs may be loaded into a common space. Alternatively the multiple types of drugs may be loaded into different spaces or chambers. The multiple types of drugs may be in fluidic communication with one another. Alternatively, the multiple types of drugs may be fluidically isolated from one another while loaded on the drug applicator. The multiple types of drugs may or may not be delivered to the same site of the eye upon use of the drug delivery device.

Any description herein of the drugs may also apply to any reagents or materials that may aid in drug delivery. The reagents or materials that may aid in drug delivery may be stored with the drugs or may be stored separately from the drugs.

FIGS. 6A to 6D show different embodiments of the drug applicator 201 in accordance with embodiments of the invention. The drug applicator may comprise an interior space 800 that may hold a drug to be delivered. The interior space may be a single continuous interior space. The interior space may have any geometric shape, such as a substantially spherical shape, cylindrical shape, conical shape, prismatic shape, or any other shape. Alternatively, the interior space may comprise multiple chambers or sections. The interior space may comprise multiple discontinuous interior spaces. In some embodiments, the interior space may comprise one or more pores or channels.

The drug applicator may comprise one or more walls 201a or solid sections that may partially or completely surround the interior space. The walls may be solid and non-porous. Alternatively, one or more portion of the walls may be porous. The walls may be impermeable to the drug contained within the interior space. Alternatively, one or more sections of the wall may be permeable to the drug contained within the interior space. In some embodiments, one or more sections of the walls may be permeable to the drug contained within the interior space under particular conditions (e.g., temperatures, light, applied ultrasound vibrations, or pressure).

In some preferable embodiments, the drug held in the drug receiving space 800 may be sealed towards an exterior space, i.e. the ambient environment, to protect the drug from being polluted by any foreign substance or gas. The protection may be particularly desirable during production, transport, and/or storage of the drug applicator 201 or the system. Directly before use the seal may be broken to allow for the drug in the space 800 to be delivered.

FIG. 6A illustrates an embodiment where the drug applicator 201 may be sealed on all surfaces. The space 800 for holding the drug inside the drug applicator 201 of this embodiment may be filled with a drug during the production process of the drug applicator 201. The sealed drug applicator may be delivered and/or used with the drug delivery device.

FIG. 6B illustrates an embodiment where the drug applicator 201 is sealed on all surfaces and comprises a port structure 201c. The port structure 201c is configured to allow filling and/or refilling of this space 800 with a drug. The port structure may allow passage of the drug only when a filling device is inserted into the port. When the drug applicator is merely provided with the drug, the port structure may optionally not allow drug the leak out of the drug applicator. The port structure may reseal when the port structure is not in use. The port may allow the filling and/or refilling of the drug applicator at the manufacture stage, after delivery of the drug applicator, and/or immediately prior to use of the drug applicator. The drug may be delivered to the interior space while the drug applicator is attached to the drug delivery device, or while the drug applicator is separated from the drug delivery device.

As illustrated in FIG. 6C, the drug applicator 201 may optionally have at least one opening at a surface directed towards a surface of the eye (e.g., scleral surface, cornea surface). The opening may be provided at a surface opposite a surface that is configured to couple with the drug delivery device. In some embodiments, the drug receiving space 800 may be configured to be filled through at least one opening at the surface directed towards the scleral surface. The drug receiving space may be filled during production of the drug applicator, after delivery of the drug applicator, and/or immediately prior to use of the drug applicator. The drug may be delivered through the opening while the drug applicator is attached to the drug delivery device, or while the drug applicator is separated from the drug delivery device.

FIG. 6D illustrates an embodiment where the drug applicator has at least one opening at a surface directed towards the eye surface and a port structure 201c. The port structure 201c is configured to allow filling and/or refilling of this space 800 with a drug. This may comprise any characteristics or may be used in any manner as described elsewhere herein.

In these embodiments, one surface, preferably a surface directed towards the surface of the eye 100, is preferably configured to have a removable cover (e.g., peel-off cover, snap-off cover, twist-off cover) and/or may be configured to be permeable for the drug held in this space 800. In some embodiments, the surface may be impermeable for the drug under some conditions, but permeable to the drug under other conditions (e.g., certain temperatures, light ranges, ultrasound transmissions, with the addition of certain solutions).

In an embodiment of the invention, the drug receiving space 800 is configured to receive a volume of a drug. The volume of the drug is preferably ranging from 10 µL to 1 mL. In some embodiments the volume of drug may be greater than 1 µL, 5 µL, 10 µL, 20 µL, 30 L, 50 µL, 75 µL, 100 µL, 150 µL, 200 µL, 300 µL, 400 µL, 500 µL, 700 µL, 1 mL, 1.5 mL, 2 mL, 3 mL, or 5 mL. The volume of drug may be less than any of the values provided herein or may fall within a range between any two of the values provided herein. Additionally or optionally a further substance can be inserted into the drug receiving space 800 to improve the delivery of the drug and/or improve at least one chemical, physical and/or pharmaceutical property of the drug. Examples of such further substances may include, but are not limited to, deionized water, buffer solution (e.g., phosphate buffered saline), or surfactant (e.g., benzyl alcohol) which may dissolve hydrophobic drug molecules.

Figure 7B:
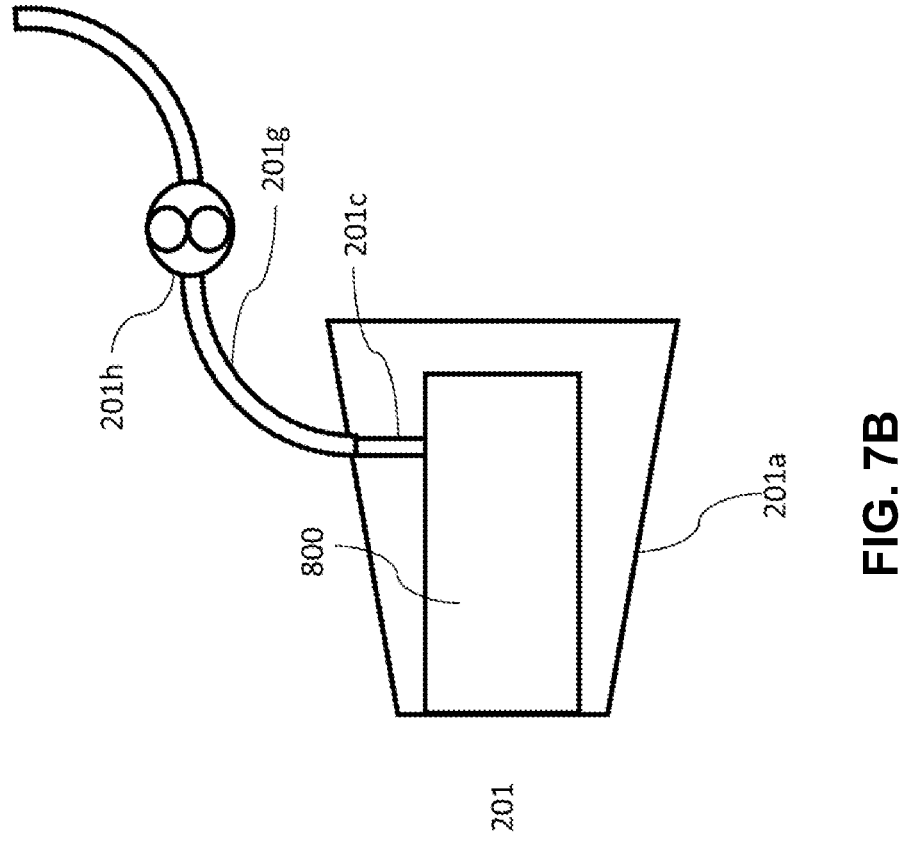
FIGS. 7A to 7B show examples of drug loading mechanisms for a drug applicator.
Figure 7A:
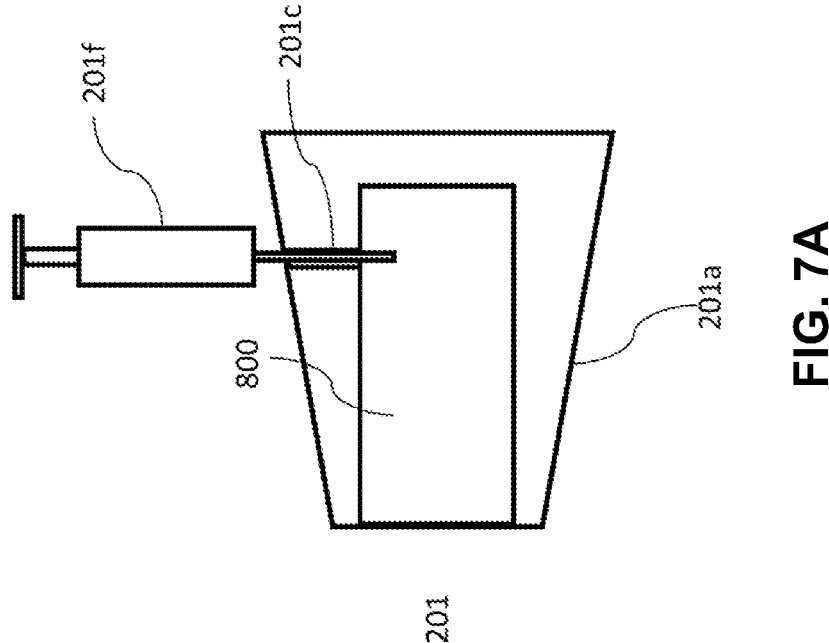

In an embodiment of the port structure 201c, the port structure is configured to be pierced by an injection needle, as illustrated in FIG. 7A. The injection needle allows liquid communication between the drug receiving space 800 and a drug reservoir or container 201f coupled to the injection needle. The drug is preferably inserted from the drug reservoir or container into the drug receiving space 800 by applying a pressure. It is preferred that the port structure 201c is self-sealing after the injection needle has been removed.

FIG. 7B shows an example of another drug filling mechanism. The port structure 201c may be coupled to a drug conveyance mechanism, such as a tube 201g. A flow control regulator 201h may be employed to control delivery of the drugs to or from the interior space 800. The flow control regular may be a binary regulator which merely controls whether drug is permitted to flow or is not permitted to flow. The flow control regulator may control the amount/rate of drug that may flow. In some embodiments, drugs may be pumped to the interior space from a drug reservoir. Positive pressure from outside the reservoir may be used to 'push' the drugs into the interior space. In some instances, negative pressure from within the interior space may be used to 'pull' the drugs into the interior space. In some embodiments, both positive and negative pressure may be used to deliver the drugs into the interior space.

These loading mechanism may be used for in situ loading. The in situ loading may occur by medical practitioners, or other users, manually. Examples of medical practitioners may include, but are not limited to, physicians, nurses, clinicians, or individuals employed by a hospital, clinic, or site that owns or operates the drug delivery devices. An individual using the device to administer to a subject may or may not have received training in the use of the device. An individual using the device may administer the device to other individuals, or may self-administer. An individual using the device may manually load the device in situ. The drug applicator may be loaded with the drug prior to using the drug. The drug applicator may be loaded with the drug prior to attaching the drug applicator to the drug delivery device, or while the drug applicator is attached to the drug delivery device. The drug applicator may be loaded with the drugs within 24 hours, 12 hours, 6 hours, 4 hours, 3 hours, 2 hours, 1 hour, 45 minutes, 30 minutes, 15 minutes, 10 minutes, 5 minutes, 3 minutes, 2 minutes, 1 minutes, 30 seconds, or 15 seconds of using the drug delivery device on a subject. The drug applicator may be loaded with the drugs while the subject is present, or while the subject is on-site. A subject may be a human subject or an animal subject. A subject may be a patient that is undergoing treatment through use of the device.

A drug may be pre-loaded into the drug applicator during a manufacturing process. A benefit of loading a drug during the production in the open space of the drug applicator may be an optimized or increased volume or concentration within sterile conditions. An interface 601b may be sealed with a sealing material to prevent contamination of the drug prior to application. The sealing material may comprise a biocompatible film. The sealing material may be a plug or other type of cover. The drug applicator may be coupled to the drug delivery device prior to treatment of the subject. The sealed interface may be unsealed by hand or with aid of a removal device. In some embodiments, the seal may comprise a porous film or membrane, which may directly face the delivery site on the eye. The drug may penetrate through the film or membrane under particular conditions. For example, the drug may penetrate through the porous film or membrane upon application of the ultrasound.

Figure 8:
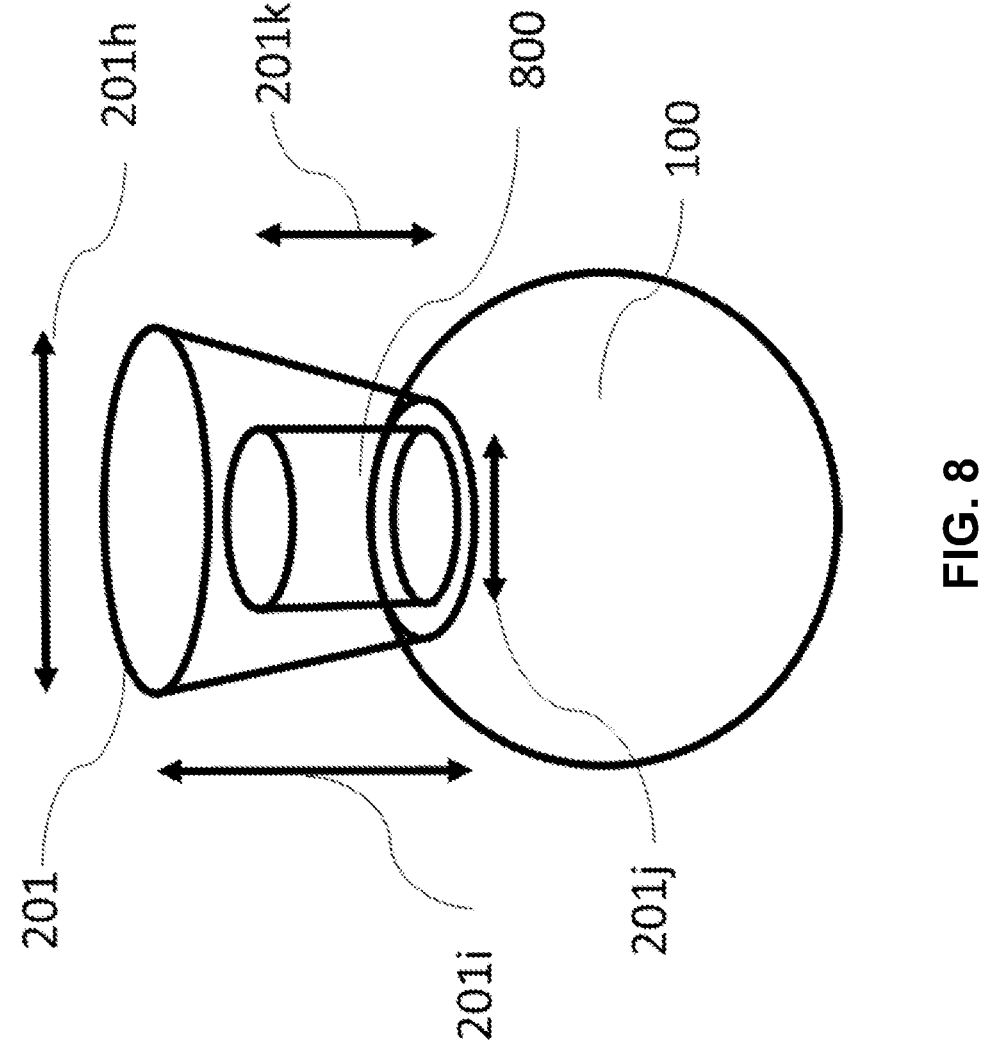
FIG. 8 shows a schematic of a drug applicator configured to be applied to an eye.

FIG. 8 shows a schematic of a drug applicator 201 configured to be applied to an eye 100. The eye may comprise a target site for delivery of drugs. The target site may be on a surface of the eye or within an intraocular space of the eye. It may be desirable for the drugs to penetrate into the intraocular space of the eye, to be delivered to a target site. Delivery of drugs to the target site may aid in the treatment of eye. The target site may be at any depth within the eye. For instance, the target site may be at least 0 mm, 0.1 mm, 0.3 mm, 0.5 mm, 0.7 mm, 1 mm, 1.2 mm, 1.5 mm, 1.7 mm, 2 mm, 2.5 mm, 3 mm, 3.5 mm, 4 mm, 4.5 mm, 5 mm, 6 mm, 7 mm, 8 mm, 9 mm, 1 cm, 1.1 cm, 1.2 cm, 1.3 cm, 1.5 cm, 1.7 cm, 2 cm, 2.5 cm, or 3 cm within the eye. The target site may have a depth less than any of the values provided or within a range falling between any two of the values provided.

The eye may comprise a delivery site that may be configured to come into initial contact with the drugs. The delivery site may be a site where the drug applicator comes into contact with the eye. The delivery site may be a site where the ultrasound is delivered to the eye. The delivery site may be provided on a surface of the eye. The delivery site may be on a sclera of the eye. The delivery site may be on a cornea of the eye. The delivery site may be on a front region of the eye on or surrounding the cornea. The delivery site may be a cornea surface, limbus, pars plana scleral surface, and/or posterior scleral surface. The delivery site may on a top region of the eye. The delivery site may on a lower region of the eye. The delivery site may on a right region or left region of the eye. The delivery site may be selected based on a target site for drug delivery. The delivery site may be selected based on the type of drug being administered. For example, for a first type of drug, a first delivery site may be selected, and for a second type of drug different from the first type of drug, a second delivery site different from the first delivery site may be selected. The delivery site may depend on a disease or eye condition being treated. For example, for a first disease or eye condition, a first delivery site may be selected, and for a second disease or eye condition different from the first disease or eye condition, a second delivery site different from the first delivery site may be selected.

The systems and method provided herein may be used to deliver drugs to an eye. The systems and methods provided herein may be used to deliver drugs to a target site of the eye. The systems and methods provided herein may allow for transscleral and/or transcorneal delivery of drugs to a target site of the eye. This may be useful for the treatment of eye diseases or conditions, such as but not limited to, prophylaxis of central retinal vein occlusion, branch retinal vein occlusion, central serous retinopathy, cytomegalovirus retinitis, retinoblastoma, intraocular lymphoma, ocular melanoma, giant cell arteritis, histoplasmosis, ischemic optic neuropathy, macular pucker, macular telangiectasia, uveitis, choroidal neovascularization, age-related macular degeneration, diabetic retinopathy, glaucoma, retinitis pigmentosa, macular edema, macular degeneration, multirecurrent ptergia, ocular toxoplasmosis, proliferative vitreoretinopathy (PVR), Stevens-Johnson syndrome, ocular cicatricial pemphigoid, an ocular degenerative condition, a post-surgery condition, or any other disease or condition as provided elsewhere herein. This may be useful for treatment of eyes, even for relatively healthy eyes, such as delivery of vitamins or other substances beneficial for eyes. This may be useful for conducting diagnostics on the eye to deliver substances that may aid in imaging or measuring characteristics of the eye.

A chosen target site and/or delivery site may depend on soft human or animal tissues. A subject, such as a human or animal subject, may have protective layers, such as an epidermis or dermis to protect the body from the environment. More soft tissue layers can be more easily penetrated or stimulated by directed ultrasound. Any of the applications provided herein for delivery to the eye may apply to other targets of a subject, such as, but not limited to, tongue, oral mucosa, nasal lining, vaginal tissue, anal tissue, or other portions of the subject's body. Indirectly accessible targets may include, but are not limited to, brain or muscles, bone, or other tissue.

The drug applicator, as described elsewhere herein, may have any form factor. For example, the drug applicator may have a tip format, ring format, or any other format. In some embodiments, the drug applicator may have a substantially spherical form, semi-spherical form, cylindrical form, conical form, form of a conical frustum, toroidal form, ellipsoidal form, prismatic form, or any other form. The drug applicator may optionally have a concave surface that may fit an eyeball curvature. A surface of the drug applicator configured to come into contact with the eyeball may have a convex, flat, or concave shape.

The drug applicator may be formed of a malleable material that may conform to fit an eyeball curvature. The drug applicator may be formed of a material that may conform to provide an increased surface area of contact between the drug applicator and the eyeball. The drug applicator may be configured to come into contact with any portion of the surface of the eye, such as a cornea surface, limbus, pars plana scleral surface, and/or posterior scleral surface. The drug applicator may or may not be configured to conform to a variety of curvatures of the eyes or features of the eye. The drug applicator may or may not be configured to conform to a variety of regions on the surface of the eye.

The drug applicator may have any dimension. In one example, the drug applicator 201 may have an outer diameter 201$h$ or at least 1 mm, 2 mm, 3 mm, 4 mm, 5 mm, 6 mm, 7 mm, 8 mm, 9 mm, 1 cm, 1.1 cm, 1.2 cm, 1.3 cm, 1.5 cm, 1.7 cm, 2 cm, 2.2 cm, 2.5 cm, or 3 cm. The outer diameter may be less or equal to than any of the values provided or fall within a range between any two of the values provided herein. The drug applicator 201 may have an inner diameter 201$j$ or at least 0.1 mm, 0.5 mm, 1 mm, 2 mm, 3 mm, 4 mm, 5 mm, 6 mm, 7 mm, 8 mm, 9 mm, 1 cm, 1.1 cm, 1.2 cm, 1.3 cm, 1.5 cm, 1.7 cm, 2 cm, 2.2 cm, or 2.5 cm. The inner diameter may be less or equal to than any of the values provided or fall within a range between any two of the values provided herein. In one example, the drug applicator 201 may have an outer height 201$i$ or at least 0.5 mm, 0.8 mm, 0.9 mm, 1 mm, 2 mm, 3 mm, 4 mm, 5 mm, 6 mm, 7 mm, 1 cm, 1.2 cm, 1.5 cm, 1.7 cm, 2 cm, 2.2 cm, 2.5 cm, 3 cm, 3.5 cm, 4 cm, 4.5 cm, 5 cm, 5.5 cm, 6 cm, 7 cm, 10 cm, 12 cm, 15 cm, 20 cm, 25 cm, or 30 cm. The outer height may be less or equal to than any of the values provided or fall within a range between any two of the values provided herein. In one example, the drug applicator 201 may have an inner height 201$k$ or at least 0.1 mm, 0.3 mm, 0.5 mm, 0.8 mm, 0.9 mm, 1 mm, 2 mm, 3 mm, 4 mm, 5 mm, 6 mm, 7 mm, 1 cm, 1.2 cm, 1.5 cm, 1.7 cm, 2 cm, 2.2 cm, 2.5 cm, 3 cm, 3.5 cm, 4 cm, 4.5 cm, 5 cm, 7 cm, 10 cm, 12 cm, 15 cm, 20 cm, or 25 cm. The outer height may be less or equal to than any of the values provided or fall within a range between any two of the values provided herein.

The dimensions of the drug applicator may be selected to hold a desired volume of the drug. The volume of drug within the various drug applicators may vary depending on a treatment plan that a drug applicator is used for. In some embodiments, the drug applicator may be configured to hold a volume of 100 μL to 5 mL. The drug applicator may be configured to hold any volume of drug, as described elsewhere herein.

The dimensions of the drug applicator may depend on a desired delivery site on the eye. For example, depending on the delivery site, different dimensions or form factors of the drug applicator may be used to deliver the drugs. In one example, a drug applicator configured to deliver drugs to the cornea with an average diameter of 11 mm may result in a minimum applicator tip inside diameter of 12 mm and a radium 6 mm which may result in an inner height of 0.884 mm-44 mm to hold a volume of 100 μL-5 mL respectively. A drug applicator configured to deliver drugs to the sclera may have below a 12 mm inner diameter with similar chosen volumes for the space. A drug applicator configured to deliver drugs to the limbus may have a 1-2 mm inner diameter. In some embodiments, for stability and accuracy of targeting the delivery area, the minimum inner diameter would need to be at least 5 mm, which would result in an inner height of 5 mm-254.71 mm for a volume of 100 μL to 5 mL respectively.

An interior space 800 of the drug applicator may determine the volume of the drug that may be held by the drug applicator. The interior space may be defined by an inner diameter and an inner height. The interior space may have a cylindrical shape. Alternatively, the interior space may have any other shape or configuration, (e.g., spherical, semi-spherical ellipsoidal, prismatic, conical, conical frustum, porous), as described elsewhere herein.

Figure 9:
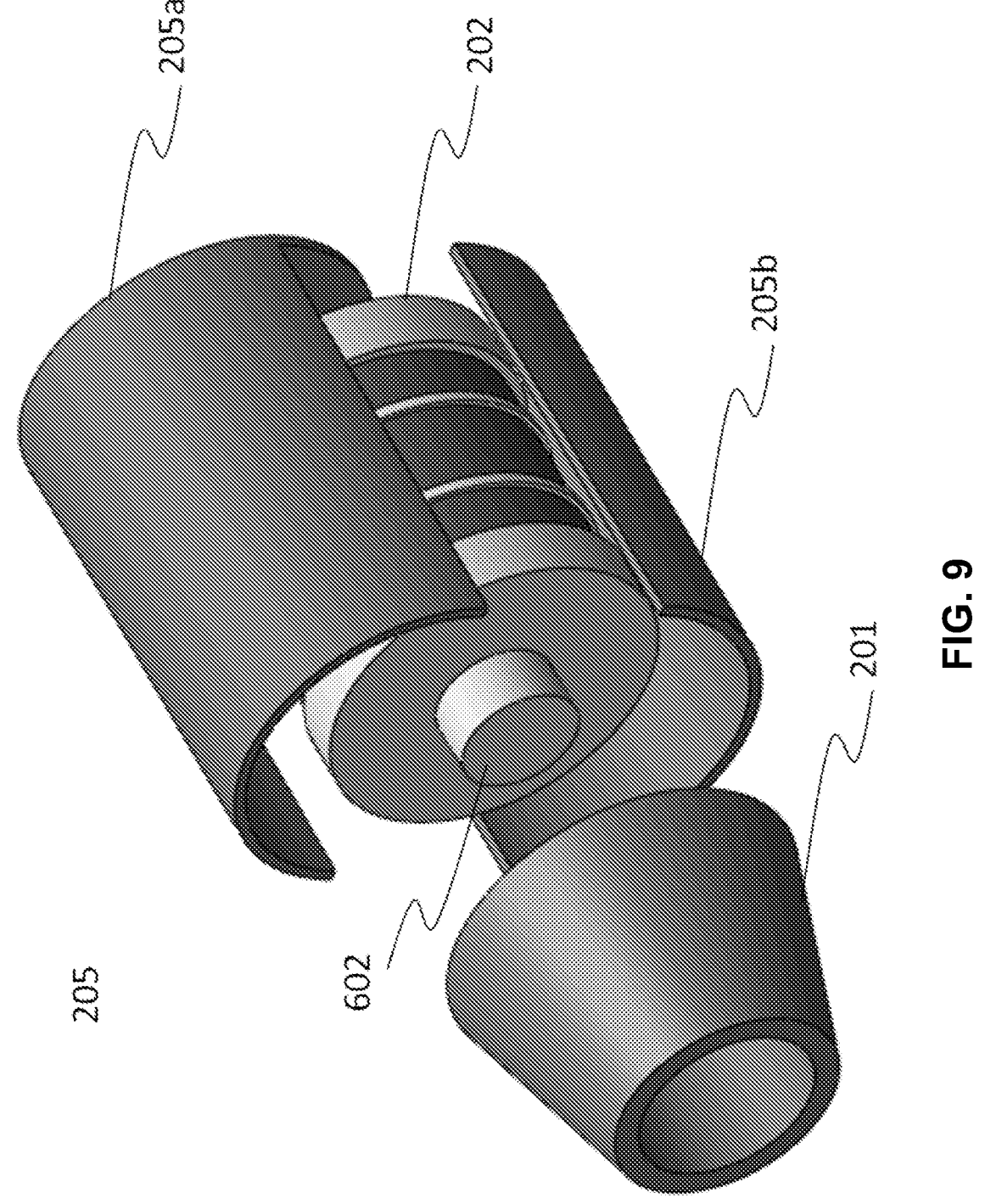
FIG. 9 shows a perspective view of an embodiment of an application head of the system.

FIG. 9 shows a perspective view of one embodiment of an application head 205 of the system. The application head may comprise a delivery unit 200. The application head 205 may be configured to accommodate the ultrasound transducer 202. Additionally and/or optionally the application head 205 is further configured to allow mechanical coupling and ultrasound coupling of the drug applicator 201 to the ultrasound transducer 202.

The outer appearance of the application head 205 may be defined by an external housing. The external housing may partially or completely enclose the ultrasound transducer. The external housing may or may not partially or completely enclose the drug applicator. In some embodiments, the drug applicator may be removable from the ultrasound transducer and may not be enclosed within the housing. The housing may be formed form a single piece. Alternatively, the housing may be formed from multiple pieces. For instance, the external housing may comprise a first housing part 205$a$ and a second housing part 205$b$. In one example, the first housing part may be an upper housing part and a second housing part may be a lower housing part. The first and second housing parts, alone or in combination with additional housing parts, may enclose the ultrasound transducer. The housing may or may not enclose additional sections, such as a signal generating unit 300 and/or a display and/or input unit 400.

A drug delivery device may comprise the ultrasound transducer. The drug delivery device may comprise the housing. The drug delivery may or may not comprise the signal generating unit and/or the display and/or input unit. The drug delivery device may have a relatively compact size. In some embodiments, the drug delivery device may have a volume of less than or equal to about 1, 5, 10, 50, 75, 100, 150, 200, 300, 400, 500, 600, 700, 800, 900, 1000, 1100, 1250, 1500, 1750, 2000, 2250, 2500, 2750, 3000, 3250, 3500, 4000, 5000, 6000, or 7000 cm³. The drug delivery device may have a volume greater than or equal to any of the values provided herein or falling within a range between any two of the values provided herein. The housing of the drug delivery device may have a volume less than any of the values provided herein, greater than any of the values provided herein, or falling within a range between any two of the values provided herein. In some embodiments, the drug delivery and drug applicator may have a volume less than any of the values provided herein, greater than any of the values provided herein, or falling within a range between any two of the values provided herein, when the drug applicator is coupled to the drug delivery device.

In some embodiments, the drug delivery device may have a maximum dimension of less than or equal to about 0.1 mm, 0.5 mm, 1 mm, 1.5 mm, 2 mm, 3 mm, 4 mm 5 mm, 7 mm, 1 cm 1.5 cm, 2 cm, 3 cm, 4 cm, 5 cm, 6 cm, 7 cm, 8 cm, 9 cm, 10 cm, 12 cm, 15 cm, 17 cm, 20 cm, 22 cm, 25 cm, 30 cm, 35 cm, 40 cm, 45 cm, 50 cm, 55 cm, 60 cm, or 70 cm. A maximum dimension may be a dimension of the device with the greatest length. A maximum dimension may be a length, width, height, diagonal, or diameter of the device. The drug delivery device may have a maximum dimension greater than or equal to any of the values provided herein or falling within a range between any two of the values provided herein. The housing of the drug delivery device may have a maximum dimension less than any of the values provided herein, greater than any of the values provided herein, or falling within a range between any two of the values provided herein. In some embodiments, the drug delivery and drug applicator may have a maximum dimension less than any of the values provided herein, greater than any of the values provided herein, or falling within a range between any two of the values provided herein, when the drug applicator is coupled to the drug delivery device.

The drug delivery device may have a weight of less than or equal to about 0.1 g, 0.5 g, 1 g, 5 g, 10 g, 50 g, 75 g, 100 g, 150 g, 200 g, 250 g, 300 g, 350 g, 400 g, 450 g, 500 g, 600 g, 750 g, 1 kg, 2 kg, 3 kg, 4 kg, 5 kg, 6 kg, 7 kg, 8 kg, 9 kg, 10 kg, 11 kg, 12 kg, 13 kg, 15 kg, 20 kg, 25 kg, 30 kg, 35 kg, 40 kg, or 50 kg. The drug delivery device may have a weight greater than or equal to any of the values provided herein or falling within a range between any two of the values provided herein. The housing of the drug delivery device may have a weight less than any of the values provided herein, greater than any of the values provided herein, or falling within a range between any two of the values provided herein. In some embodiments, the drug delivery and drug applicator may have a weight less than any of the values provided herein, greater than any of the values provided herein, or falling within a range between any two of the values provided herein, when the drug applicator is coupled to the drug delivery device.

The device may be sufficiently compact to be a handheld device. The device may be configured to be carried in a single human hand. The device may be configured to operate using a single human hand. The device may be carried or operated using two human hands. The device may comprise a gripping region configured to be gripped by a single human hand. The gripping region may optionally be contoured to be gripped by a human hand. The contouring may allow the various fingers of the human hand to be received on the grip. The contouring may allow the device to be held in an ergonomic manner while the device is used to administer ultrasound to a subject.

The device may be configured to be a wearable device. The device may be worn on any portion of a subject's body. For instance, the device may be worn on a subject's head, face, neck, torso, arm, hands, legs, or feet. The device may be worn to at least partially cover one or more of the subject's eyes. The device may be supported on a subject's head. In some embodiments, the device may be supported with aid of at least a top portion of the head. In some embodiments, the device may be supported with aid of a forehead of the subject. The device may be supported with aid of one or more ears of the subject. For examples of wearable configurations are provided in greater detail elsewhere herein.

Figure 10:
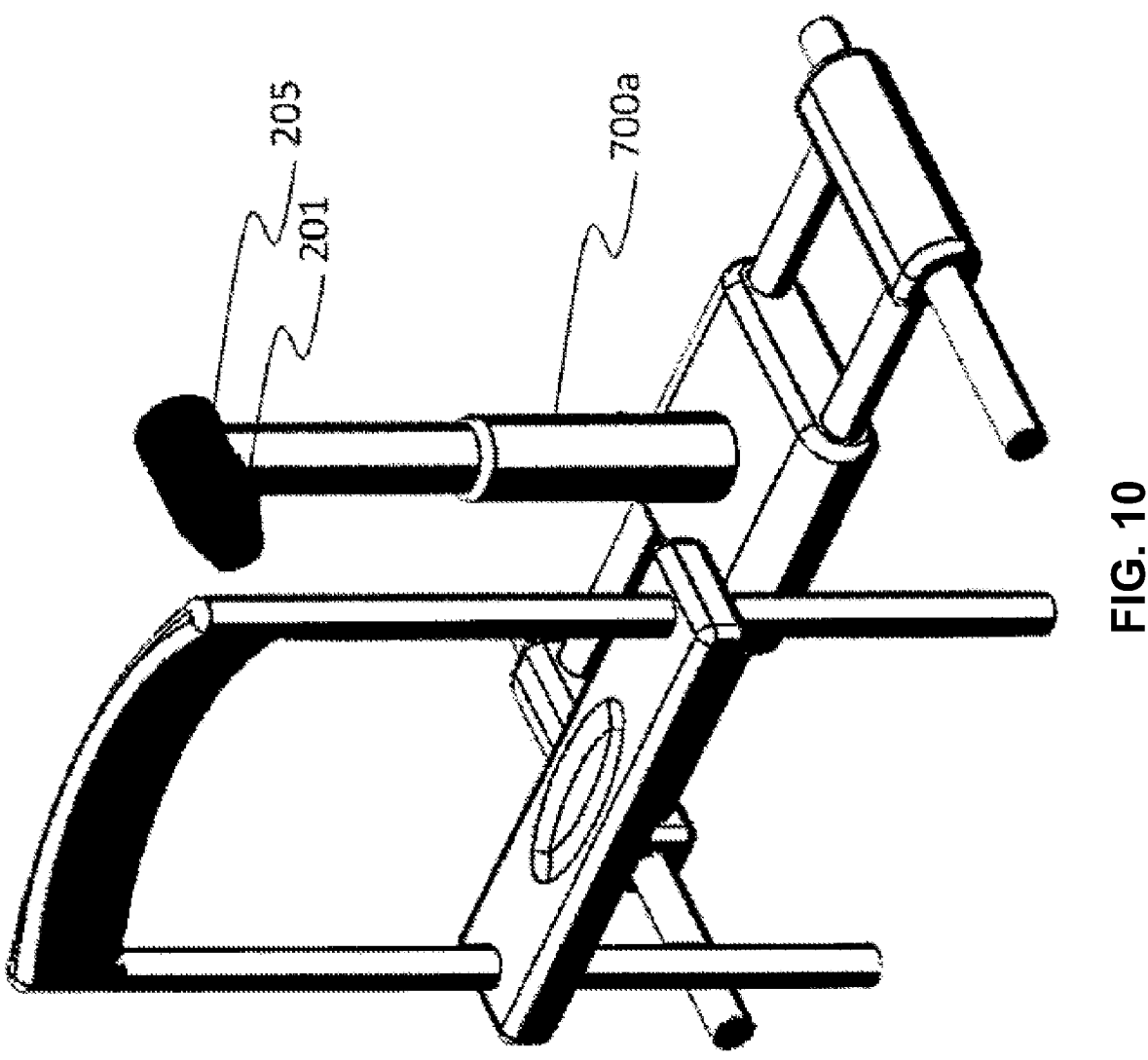
FIG. 10 shows a perspective view of an embodiment of the system according to one aspect of the invention.

FIG. 10 shows a perspective view of an embodiment of the system according to one aspect of the invention. The system may comprise an application head 205, the drug applicator 201, and additional housing and holding parts 700a. The additional housing and holding parts preferably accommodate all components of the system. Alternatively, some components of the system are accommodated in the at least one further housing (not shown). A signal generating unit 300 may or may not be incorporated as part of the additional housing and holding parts. A display and/or input unit 400 may or may not be incorporated as part of the additional housing and holding parts. The drug applicator may or may not be removable from the application head. The application head may or may not be removable from the additional housing and holding parts. The application head may be coupled or decoupled from the additional housing and holding parts in a repeatable manner.

The additional housing and holding parts 700a may be configured to receive a patient's head. To receive a patient's head, preferably a chin-rest and/or forehead-rest are provided. In one embodiment of the invention the application head 205 is an attached to a flexible arm, allowing for an adjustment of the application head 205 and the drug applicator 201 relatively to the rest of the additional housing and holding parts 700a. For example, a height of the application head 205 may be adjusted relative to the patient's eye when the patient's head is resting on the chin-rest and forehead-rest. The adjustment of the height of the application head may allow the accommodation of various facial features, sizes, and shapes. The application head may be adjusted to be brought to a desired position relative to an eye of the patient. The flexural arm may extend and/or retract to adjust the height of the application head. In some embodiments, the flexural arm may comprise one or more telescoping components that may allow for adjustment of length of the arm. The length of the flexural arm may be manually adjusted, or may be adjusted with aid of one or more actuator that may be capable of causing one or more sections of the arms to move relative to one another in response to a signal or command. The chin-rest and forehead-rest may allow a patient's eye to remain at a substantially static location, while the application head is brought to a desired position relative to the eye. The flexural arm may also optionally allow the application head to move laterally further and/or closer to the eye. The application head may be brought to a desired position relative to the eye to deliver the ultrasound and/or drugs.

As previously described, the drug delivery device may have any form factor, such as a wearable form factor. The drug delivery device may be configured to worn on the head of the subject. The drug delivery device may be configured to cover at least a portion of a face of the subject. The drug delivery device may be configured to cover a single eye or both eyes of the subject. The drug delivery device may be configured to at least partially cover an eye of the subject. The drug delivery device may be configured at least partially wrap around the subject's head.

In some embodiments, the drug delivery device may be supported with aid of a top of the subject's head. For instance, the drug delivery device may have the form of a hat or helmet. The hat or helmet may cover at least a portion of the top of the subject's head. A portion of the drug delivery device may extend down from the hat or helmet to cover the subject's eye or eyes. For instance, the portion extending down may have a form factor of a visor, goggles, or glasses. The drug delivery device may have the form factor of a visor, headband, or other object that may completely or partially encircle the subject's head without necessarily covering the top of the subject's head. One or more straps that may partially or completely circle the subject's head may be used to support the device on the subject's head. The drug delivery device may have the form factor of goggles or glasses. The drug delivery device may be at least partially supported by one or more ears of the subject. For instance, the drug delivery device may comprise portions that may extend past the subject's ears. The portions that extend past the subject's ears may include portions of glasses that may partially wrap behind the ear, or may include portions of goggles or headbands that may extend beyond the ear, or may include portions of hats or helmets that may extend beyond the ear. For instance, the drug delivery device may comprise a temple and/or ear piece that may extend to the ear and/or wrap behind the ear. The drug delivery device may have any form factor of any type of eyewear. The drug delivery device may comprise an eyewear frame comprising at least one extension configured to extend behind a subject's ear when the device is worn by the subject.

Figure 11:
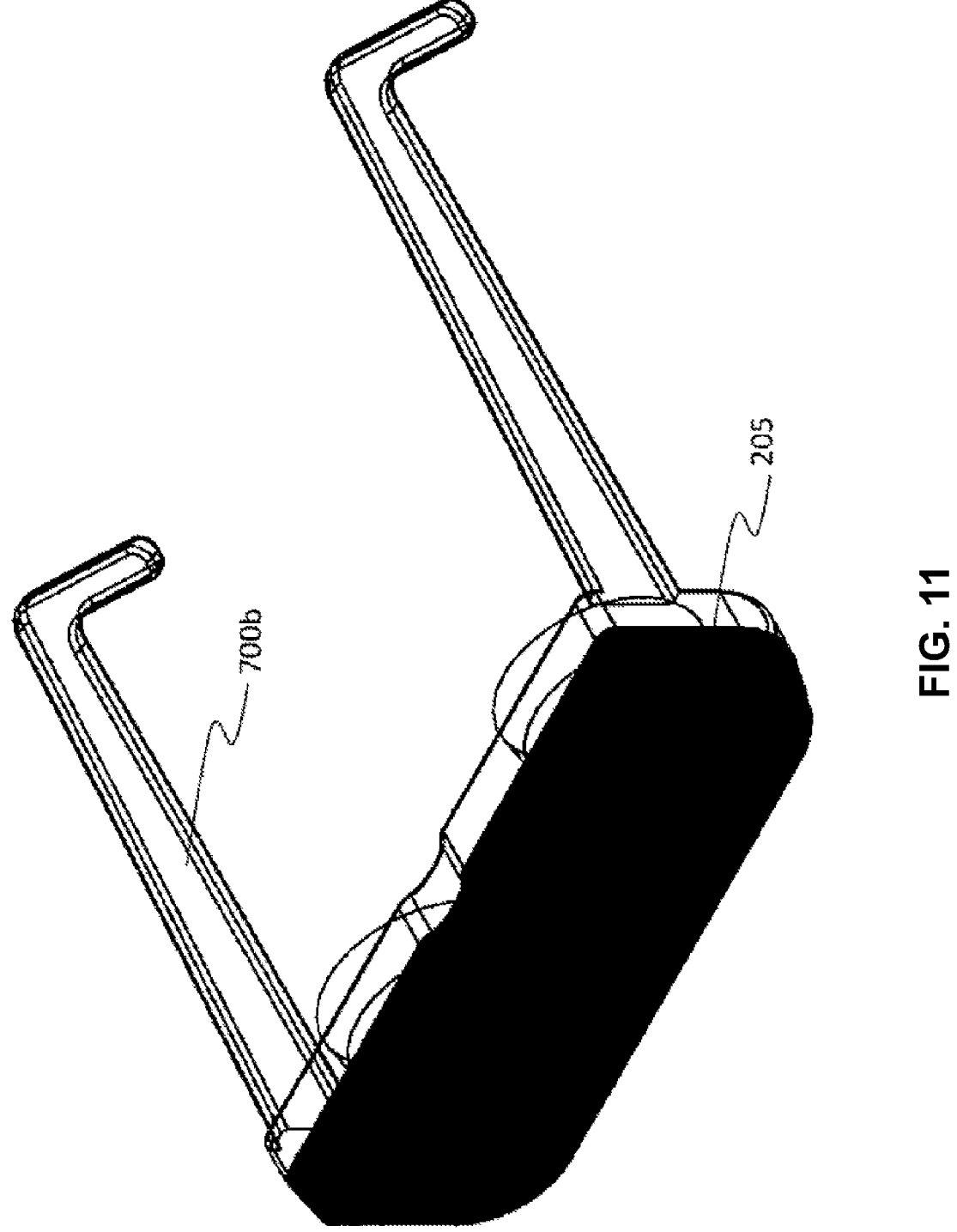
FIG. 11 shows a perspective view of a wearable embodiment of the system according to one aspect of the invention.
Figure 12:
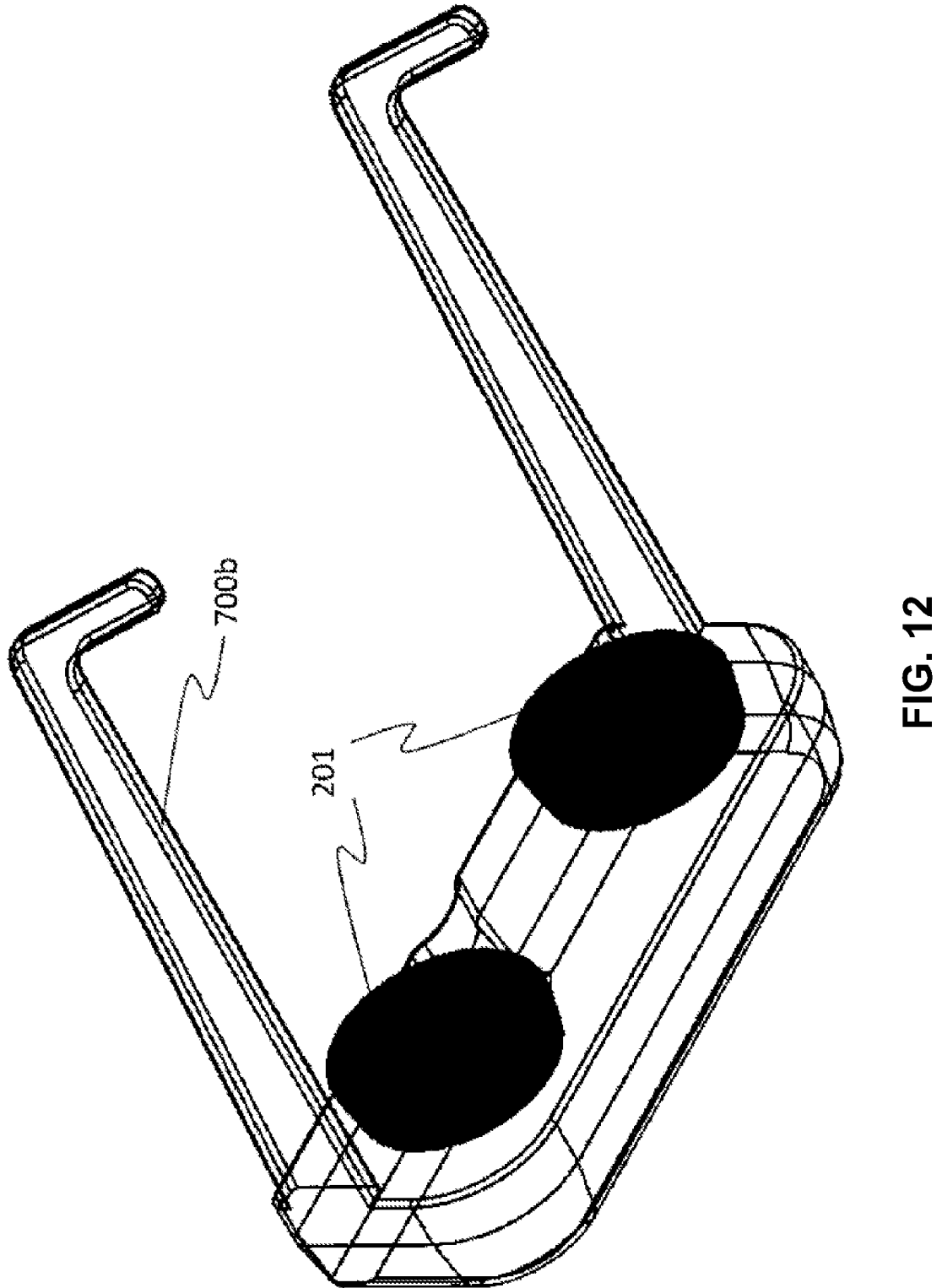
FIG. 12 shows a perspective view of a wearable embodiment of the system according to one aspect of the invention.

FIG. 11 shows a perspective view of an embodiment of the system according to one aspect of the invention. FIG. 12 shows a perspective view of another embodiment of the system according to one aspect of the invention. The application head 205 and the system may be integrated into a device that resembles the outer appearance of a pair of glasses, or other type of eyewear or wearable device. Any description herein of glasses may apply to any other type of eyewear or wearable device.

Directions such as front, left, and right are derived from directions during normal use of a glasses device. The application head 205 may be formed in a front portion of the glasses device. The drug applicator 201 may be attached to the application head 205 at a position in front of the left and/or right eye. Further housing and holding parts 700b are preferably forming a frame and/or yokes of the glasses device. The housing and holding parts may or may not comprise a signal generating unit 300 and/or a display and/or input unit 400.

An application head may be supported by an eyewear frame. One or more ultrasound-generating devices may be supported by the eyewear frame. Each ultrasound-generating device may be configured to generate ultrasound that is delivered to a desired site of the eye when the device is worn by the subject. In some embodiments, a single ultrasound-generating device may be supported by the eyewear frame over a single eye. The ultrasound-generating device may be positioned on the eyewear frame to at least partially cover an eye when the device is worn by the subject. For example, the ultrasound-generating device may be configured to deliver ultrasound to the left eye only, or the right eye only. In some embodiments, the ultrasound-generating device may be affixed to the eyewear frame and may not move relative to the eyewear frame.

In some embodiments, the ultrasound-generating device may be movable relative to the eyewear frame. For instance, the ultrasound-generating device may be configured to slide to the left or to the right, to cover a desired eye. For example, the ultrasound-generating device may be positioned over the left eye to deliver ultrasound to the left eye. When it is desirable to deliver ultrasound to the right eye, the ultrasound-generating device may be moved to be positioned over the right eye. The ultrasound generating device may be capable of moving along the eyewear frame without being removed or separated from the eyewear frame. Alternatively, the ultrasound generating device may be detached from the eyewear frame at a first position and reattached to the eyewear frame at a second position. In some embodiments, the positions relative to the left eye and/or right eye may be adjustable. This may be useful for accommodating different users with different face shapes and sizes. In some instances, the positions relative to the left and and/or right eye may be lockable. This may be advantageous when a repeat subject is wearing the device. The positions may be set for a particular subject, and whenever the subject undergoes a treatment session, the measurements may be fixed for that particular subject to place the ultrasound-generating device at the same position relative to the eye.

Generation of the ultrasound may cause the delivery of at least one drug to a target site in the eye without damaging tissue of the eye. In some embodiments, an eyewear frame may support two ultrasound-generating devices, corresponding to each eye of the subject. In some embodiments, a single ultrasound-generating device may be used to deliver ultrasound to both eyes of the target. The ultrasound-generating device may generate ultrasound which may be conveyed via low attention materials to both eyes. In some embodiments, the ultrasound-generating device may be coupled to two drug applicators which may convey the ultrasound to both eyes.

The ultrasound-generating device may or may not come into direct contact with the eye. In some embodiments, a drug applicator may be coupled to the ultrasound-generating device. The drug applicator may be supported by the eyewear frame. The drug applicator may be supported by a respective ultrasound-generating device. The drug applicator may come into contact with an eye. The drug applicator may be located to at least partially cover one or more eyes of the subject when the device is worn by the subject. The drug applicator may be coupled and/or decoupled from the ultrasound-generating device in a repeatable manner. If the ultrasound-generating device is movable or detachable from the eyewear frame, the drug applicator may be moved and/or detached with the ultrasound-generating device. In some embodiments, the drug applicators may be fixed to the eyewear frame while the ultrasound-generating devices may be detached or movable. In some embodiments, the drug applicators may be movable or detachable relative to the eyewear frame independent of the ultrasound-generating device.

The drug applicators may be positioned relative to the eyewear frame to come into contact with a surface of the eye, or an eyelid of the eye. The ultrasound-generating device and/or drug applicators may move sideways along the frame of the eyewear. The ultrasound-generating device and/or drug applicator may move closer or further away from the surface of the eye (e.g., forwards and backwards). The drug applicator may be configured to deliver drugs to the surface of the eye. The drug applicator may be configured to deliver ultrasound from the ultrasound-generating device to the eye.

Advantages of a wearable design may comprise improved usability, especially the improved user experience during the application process. The wearable design may also allow for easy alignment of the drug applicator and/or ultrasound to a desired site of the eye. In some embodiments, a subject may wear the device. Then the position of the drug applicator and/or ultrasound-generating device may be adjusted for the subject to allow delivery of ultrasound and/or drugs in a desired manner. The subject may wear the device for a duration of a treatment. In some embodiments, there may be treatment plans that call for the subject to wear the device at different times in the day or over the course of multiple days, weeks, or months. The components of the device, such as the ultrasound-generation device and/or drug applicator, may be readjusted every time the subject puts on the device. Alternatively, the previous positions for the components may remain for the eyewear and no adjustment or very little adjustment may be required when the subject puts on the eyewear again.

Figure 13:
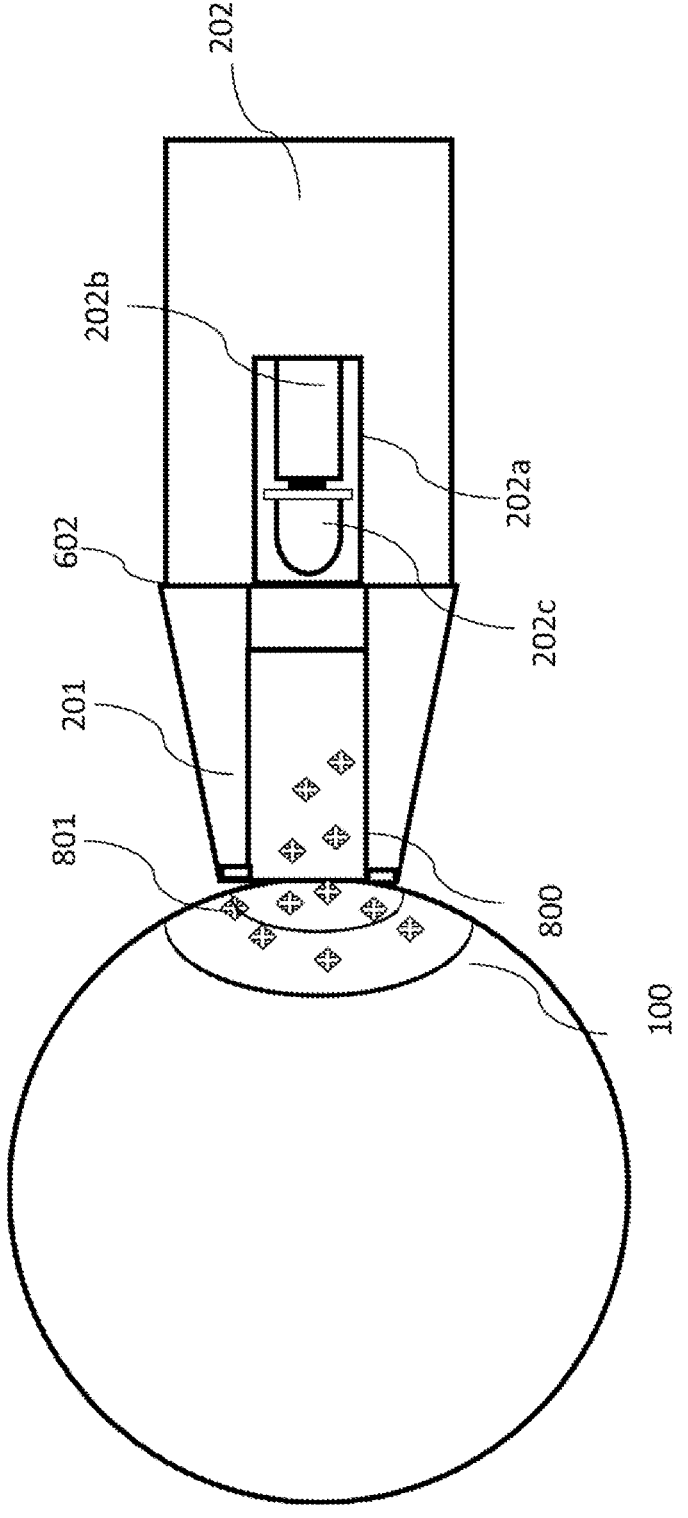
FIG. 13 shows an example of a delivery unit comprising a light source.

FIG. 13 shows an example of a delivery unit comprising a light source, in accordance with embodiments of the invention. In some embodiments, it may be useful to apply light to drugs that are delivered to the eye to produce a desired effect. Examples of desired effects may include triggering a chemical reaction of the drug, such as cross-linking of the drug, altering the properties of the drug for improved penetration or desired effects of delivery.

In some instances, after delivery of drug and the ultra-sound to a desired site of the eye, a light may be provided to the desired site of the eye. In some instances, prior to, concurrently with, and/or subsequent to delivery of the drug to the desired site of the eye, the light may be provided. In some instances, prior to, concurrently with, and/or subsequent to delivery of the drug to the desired site of the eye, the light may be provided. The light may be provided from a source external to a drug delivery device. Alternatively, the light may be provided from the drug delivery device. In one example, an application head may comprise an on-board light source.

A drug delivery device may comprise an ultrasound-generating device and a light source configured to generate light that is delivered to a desired site of the eye. The drug delivery device may be configured to couple with a drug applicator that may aid in delivery of the ultrasound to the desired site of the eye and permit light from the light source on-board the drug delivery device to be delivered to the desired site of the eye.

The drug delivery device may comprise a housing. The light source may be provided within the housing. The ultrasound-generating device and the light source may be provided within a common housing. The housing may prevent light from the light source from escaping the device in an undesired manner. The light source may have a fixed position relative to the ultrasound-generating device. The light source may be coupled to the ultrasound-generating device.

The ultrasound-generating device may comprise an interior space within which the light source resides. In one example, the ultrasound-generating device may have a geometric cross-section with a free space substantially in the middle which forms the interior space. For example, the ultrasound-generating device may have a circular cross-section with a free space at or near the center that forms the interior space. The light source may be provided within the free space and may directly shine light toward the drug applicator. The interior space or another portion of the drug delivery device may optionally comprise an optical element that may modify light emitted by the light source. Examples of an optical element may comprise a lens, filter, condenser, diffractor, prism, mirror, dichroic, beamsplitter, or any other type of optical element. The optical element may change a path of the light, focus the light, diffuse the light, split the light, reflect the light, filter out one or more wavelengths of the light, or modify the light in any other manner.

The light source may be any type of light source. The light source may emit light anywhere along the electromagnetic spectrum. The light source may emit visible light, ultraviolet (UV) light, infrared light, microwaves, or any other type of light. In some embodiments, the light source may emit UV light. The light source may be a UV lamp emitting light along the UV-A wavelengths. In some embodiments, the light source may emit light at UV-B and/or UV-C wavelengths. The light source may emit light having wavelengths within the range of 10 nm to 400 nm. The light source may emit light having wavelengths between 315-400 nm. The light source may emit light having wavelengths less than 10, 30, 50, 100, 150, 200, 250, 280, 300, 315, 325, 350, 400, 450, or 500 nm. The light source may emit light having wavelengths greater than any of these values or falling within a range between any two of these values. The light source may comprise one or more LEDs. The light source may comprise one or more lasers.

In one example, the drug delivery device and/or drug applicator may be used for UV (e.g., UV-A) treatment of a target site. The drug applicator 201 may comprise an inlet 201a facing the gap 601a and/or the ultrasound transducer 202. The ultrasound transducer may be coupled to the light source (e.g., UV lamp) 202c. The light source may be supported by a support structure 202b. The light source and/or support structure may be within an interior space 202a of the ultrasound-transducer. The light source may be partially or completely within the interior space. The light source may or may not protrude from the interior space. In some embodiments, the light source may completely protrude from the interior space.

The emitted wavelengths from the light source may pass through the inlet 201a of the drug applicator, whereby the drug applicator outer shell 201b may be potentially opaque and formed of or coated with material that may prevent the light from escaping through the drug applicator shell. For example, if the light from the light source comprises UV light, the drug applicator may comprise a shell that is formed of or coated with UV reflecting material to prevent any UV exposure to the outer environment. The only outlet for the UV light may be via the side facing the delivery site (e.g., the surface of the eye). In some embodiments, less than 20%, 10%, 5%, 3%, 2%, 1%, 0.5%, or 0.1% of the light emitted may escape through the housing of the ultrasound-generating device and/or the outer shell of the drug applicator.

Thus, the drug applicator may comprise a first portion formed of an opaque material configured to at least partially define one space configured to hold the drug, and a second portion formed from a material that is at least partially transparent to light of a selected wavelength, configured to permit the light to pass from one side of the drug applicator to another side of the drug applicator. The space configured to hold the drug may be a single continuous space. The space configured to hold the drug may comprise multiple discontinuous spaces. The multiple discontinuous spaces may comprise pores. The first portion may be configured so that the light from the light source may not penetrate into the space to hold the drugs. This may be useful for preventing a reaction that may be initiated by the light source (e.g., cross-linking) until the drug is delivered to the desired site. The first portion may comprise a surface that is coated with a material that reflects light of selected wavelengths. For instance, if the light from the light source is a UV light, the coating may reflect UV light. The coating may be provided on an outer surface of the drug applicator. This may reduce any UV exposure to an outer environment. The coated may be provided on an inner surface of the drug applicator. This may reduce any UV exposure to the drugs within the space of the first portion. In some embodiments, the material that forms the first region may be reflective of the selective wavelengths (e.g., UV wavelengths).

The first portion may comprise a target side that may be configured to contact a desired site of the eye. The target side may come into contact with an eyelid or a surface of the eye, such as the sclera, cornea, and/or limbus. In some embodiments, the target side may be formed from a soft, biocompatible material. The soft material may allow for comfortable contact with the eye, and/or increased surface area between the drug applicator and the eye, which may allow improved delivery of ultrasound to the eye. The target side may be configured to deliver reagents that may improve delivery of the drug to the target side. Further description of this is provided in greater detail elsewhere herein. In some embodiments, the first portion may be formed from an elastic material. The first portion may have any material property as described elsewhere herein for a drug applicator. The first portion may allow for soft comfortable contact with the eye without requiring a separate layer at the target side. The material for the entirety of the first portion may be the same, or a different material may be provided at the target side. The material provided at the target side may be softer than the rest of the material.

In some embodiments, the material used by the first portion of the drug applicator may be formed from an opaque elastic material, such as polymers or silicone.

The second portion of the drug applicator may be transparent to selected wavelengths of light. For instance, the second portion of the drug applicator may be transparent to at least a subset of the light emitted by the light source. In some instances, the second portion of the drug applicator may be transparent to an entirety of the wavelength range of light emitted by the light source. The second portion of the drug applicator may be transparent to UV light (e.g., UV-A light, UV-B light, and/or UV-C light). The second portion may be at least partially surrounded by the first portion. In some embodiments, the first portion may surround an interior space. The second portion may occupy a portion or an entirety of the interior space. In some embodiments, one or more drugs may be provided within the interior space, and the second portion may occupy a portion of the interior space to help contain the drugs. The second portion may comprise a solid, liquid, gel, and/or other type of material.

The drugs held by the drug applicator may be any type of drug that may be delivered the eye. In some embodiments, the light source may be configured to initiate a reaction by the drug. For example, the light source may be configured to initiate cross-linking by the drug. In one example, the drug may be riboflavin. In some embodiments, collagen at the delivery site may be cross-linked using light from the light source.

In one implementation, UV wavelengths can be generated via the light source at the ultrasound-generating device. The light may penetrate through the transparent applicator inlet 201a, and the space 800. The space may be used to hold drugs. The light may reach the delivery site 100 without scattering through the drug applicator outer shell 201b. This may result in specific focused UV light for potential treatment of keratoconus treatment and/or LASIK/SMILE-related corneal ectasia. This may occur by cross-linking riboflavin or any other cross-linking agents at the delivery site, making it corneal cross-linking CXL.

The combination of opaque and transparent material used by the drug applicator may be configured to allow UV illumination in selected areas and reduced overexposure of two other areas due to safety considerations.

Drug applicators can have any form factor, such as those described elsewhere herein. For example, drug applicators may be, but are not limited to, round, cylindrical, conical, oval, triangle, square or rectangular. The drug applicator surface facing the gap 601a and/or target site 100 can have the same shape or different shapes. They may have the same or different shapes relative to one another or the rest of the drug applicator. The target-facing surface may be coated with a biocompatible material which may be in contact with the target surface. The material can cover or close the space 800 of the drug applicator to prevent contamination of the drug. The material may also prevent spilling and loss during handling of the drug applicator.

FIGS. 14A to 14G show examples of various configurations of a delivery unit or portion thereof. An ultrasound-generating device 202 may be provided.

Figures 14A, 14B, 14C, 14D, 14E, 14F, 14G:
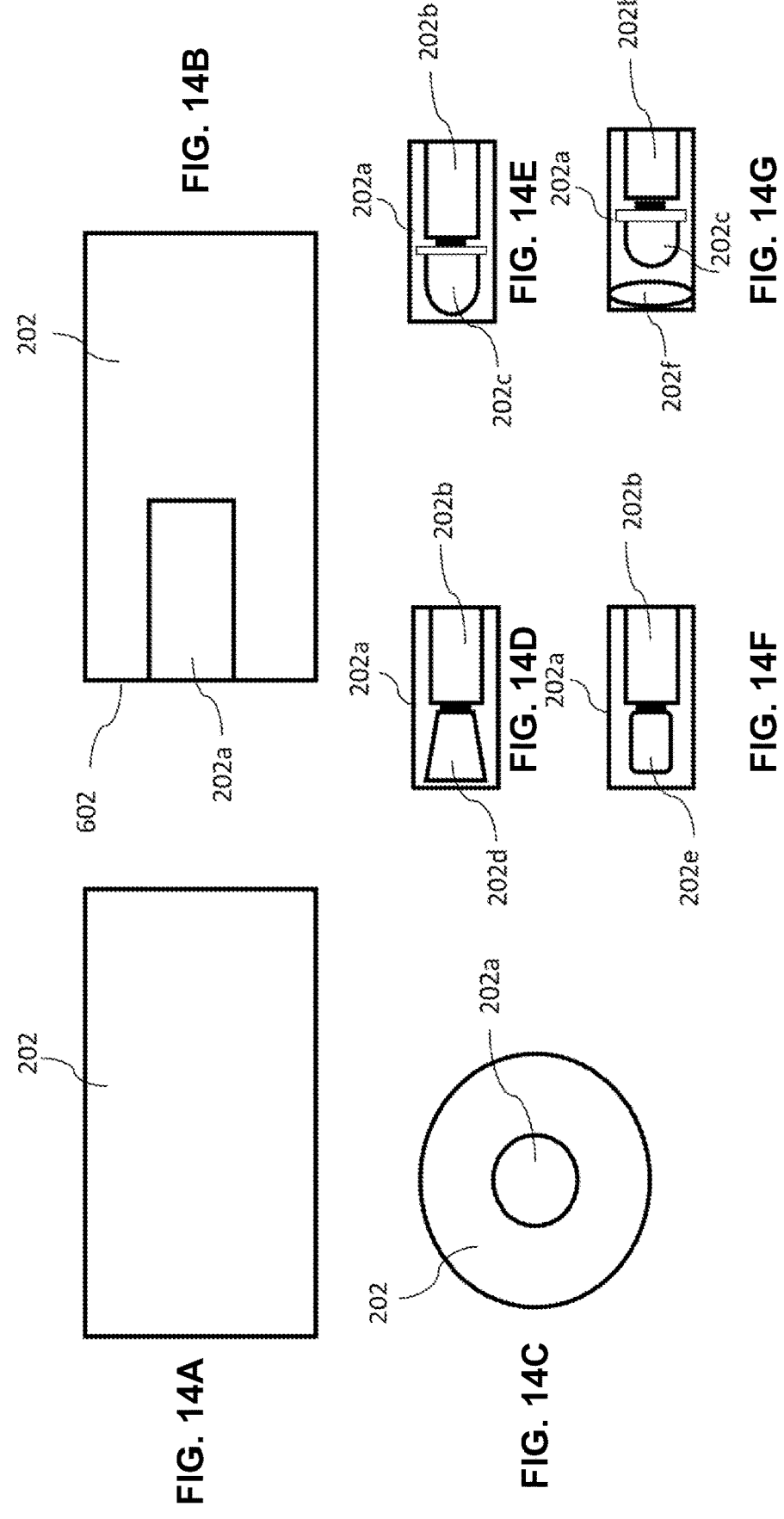
FIGS. 14A to 14G shows examples of various configurations of a delivery unit.

FIG. 14A shows an example of an ultrasound-generating device 202. The ultrasound-generating device may comprise a transducer which may not require an interior space.

FIG. 14B shows an example of an ultrasound-generating device 202 which may comprise an interface 602 configured to face a drug applicator. The interface may permit coupling between the ultrasound-generating device and the drug applicator. The interface may be provided on a side of the ultrasound-generating device that may be facing toward the eye. The ultrasound-generating device may comprise an interior space 202a.

FIG. 14C may show a cross-section of the ultrasound-generating device 202 having an interior space 202a. The ultrasound-generating device may have any cross-sectional shape. For example, the ultrasound-generating device may have a circular, elliptical, triangular, square, rectangular, trapezoidal, pentagonal, hexagonal, octagonal, or any other shaped cross-section. The interior space may have any cross-sectional shape. For instance, the interior space may have a circular, elliptical, triangular, square, rectangular, trapezoidal, pentagonal, hexagonal, octagonal, or any other shaped cross-section. The interior space may have any cross-sectional shape. The ultrasound-generating device and the interior space may be concentrically arranged. The ultrasound-generating device and the interior space may each comprise an axis extending through their respective lengths. The axes may pass through the center of their respective portions. The axes of each of these may be parallel to one another. The axes of each of these may directly overlay one another.

In some embodiments, an emitter, such as a light source, may be provided within the interior space. Alternatively or in addition, a data collection device may be provided. The data collection device may comprise one or more sensors that may be capable of collecting data. For example, the data collection device may comprise one or more cameras, microphones, infrared detectors, UV detectors, lidar, or any other type of data collection device.

FIG. 14E shows an example of a light source 202c that may be within the interior space 202a of the ultrasound-generating device. The light source may be supported by a support structure 202b. The support structure may provide connection of the light source to a power source, such as one more batteries provided elsewhere herein. In some instances, the support structure itself may comprise a power source, such as a battery, that may directly provide power to the light source. The ultrasound-generating device and the light source may or may not be powered by the same power source. They may be powered by different power sources. In some embodiments, the support structure may be formed of a high ultrasound attenuation material, which may reduce the influence of the ultrasound on the light source. In some embodiments, it may be desirable for the support structure to provide active or passive damping on ultrasound generated by the ultrasound-generating device. This may allow the light source to experience less or no ultrasound signals. Any description herein of a support structure for a light source may apply to a support structure for any other object, such as an emitting device or data collection device, provided within the interior space.

FIG. 14G shows another example of a light source 202c that may be within the interior space 202a of the ultrasound-generating device. The light source may be supported by a support structure. One or more optical elements 202f may be provided. The one or more optical elements may modify the light that has been emitted. Alternatively or in addition, one or more optical elements may be provided in the drug applicator. In some instances, one or more adjustment mechanisms 202f may be provided, which may be provided for an emission device or a data collection device. The adjustment mechanism may be an optical element or other type of adjustment mechanism. The adjustment mechanism may modify emission from a device within the interior space, or emissions from outside the interior space coming into the interior space.

FIG. 14D shows an example of a data collection device, such as a camera 202d. The camera may be supported on a support structure 202b. The camera may be useful to image the delivery site. The camera may be used to capture still images or dynamic images. The camera may be a video camera that may be capable of capturing streamed images. The camera may be useful for collecting data about the delivery site and how the treatment is going. The transparent portion of the drug applicator may permit the camera to image the delivery site through the drug applicator. In some embodiments, the camera may be used in conjunction with the light source. The light source may be used to illuminate the region that is being imaged. In some embodiments, the light source may be to initiate a reaction by the drug, which may be imaged.

FIG. 14F shows another example of a data collection device, such as a microphone 202e. The microphone may be supported on a support structure 202b. The microphone may be useful to collect acoustic data from the delivery site. In some embodiments, the microphone may be useful for collecting ultrasonic data. In some embodiments, the microphone may be used in conjunction with the light source.

In some embodiments, one or more modules may be swapped in an out of the interior space of the ultrasound-generating device. For example, a light source may be swapped in and out with a different light source, or with a data collection device. A single module may fit within the interior space or multiple modules may fit within the interior space. For example, both a light source and a data collection device, or multiple types of data collection devices, may fit within the interior space.

A drug applicator may be used to deliver drugs to a delivery site on the eye. The drug applicator may also be used to deliver ultrasound to the delivery site on the eye.

Alternatively or in addition, a drug-holding overlay may be used to deliver drugs to a delivery site on the eye. The drug-holding overlay may be configured to contact a surface of the eye. The drug-holding overlay may be positioned on the surface of the eye and/or may at least partially adhere to the eye.

The drug holding overlay may be configured to permit closure of the eye while the drug-holding overlay is applied to the surface. The drug holding overlay may have a low profile that may allow it to not protrude from the eye by more than 5 mm, 4 mm, 3 mm, 2.5 mm, 2 mm, 1.5 mm, 1.3 mm, 1.2 mm, 1 mm, 0.9 mm, 0.8 mm, 0.7 mm, 0.6 mm, 0.5 mm, 0.3 mm, 0.1 mm, 0.05 mm, or 0.01 mm. In some embodiments, the drug-holding overlay may be a contact lens, film, membrane, layer, or sheet. The drug holding overlay may be formed from a flexible material. The drug holding overlay may be malleable or may flex to conform to a shape of the surface of the eye.

The drug holding overlay may have any shape. For instance, the drug holding overlay may have a substantially circular shape. The drug holding overlay may have an elliptical shape, rectangular shape, triangular shape, crescent shape, ring shape, or any other shape. The drug holding overlay may be substantially curved when in a natural state, similar to a curved surface of the eye. Alternatively, the drug holding overlay may be flat when in a natural state.

The drug holding overlay may be formed of a porous material. The porous material may enable the drug holding overlay to hold at least one drug within the pores. The drug holding overlay may be formed of a hydrophilic, hydrophobic, amphiphilic, and/or sterile material. In some instances, the drug holding overlay may comprise a microcellular foam. In one example, the drug holding overlay may comprise a hydrophilic microcellular foam adjoined with a hydrophobic barrier film. The drug holding overlay may comprise a polymeric material, such as a polymeric film. The drug holding overlay may be formed from a low attenuation material. Any of the characteristics of the low attenuation material as described elsewhere herein may apply to the drug holding overlay. For example, the drug holding overlay may have an attenuation coefficient of less than 20, 15, 12, 10, 9, 8, 7, 6, 5, 4, 3, 2, 1, 0.5, or 0.1 dB/(MHz cm).

At least one drug may be encapsulated in the drug holding overlay. At least one drug may be adhered or applied on a surface of the drug-holding overlay.

A method for delivery of at least one drug may comprise applying the drug-holding overlay to a surface of the eye. An ultrasound-generating device may be positioned relative to a desired site of the eye. Ultrasound may be generated with aid of the ultrasound-generating device, and ultrasound may be applied to the desired site.

Figure 15:
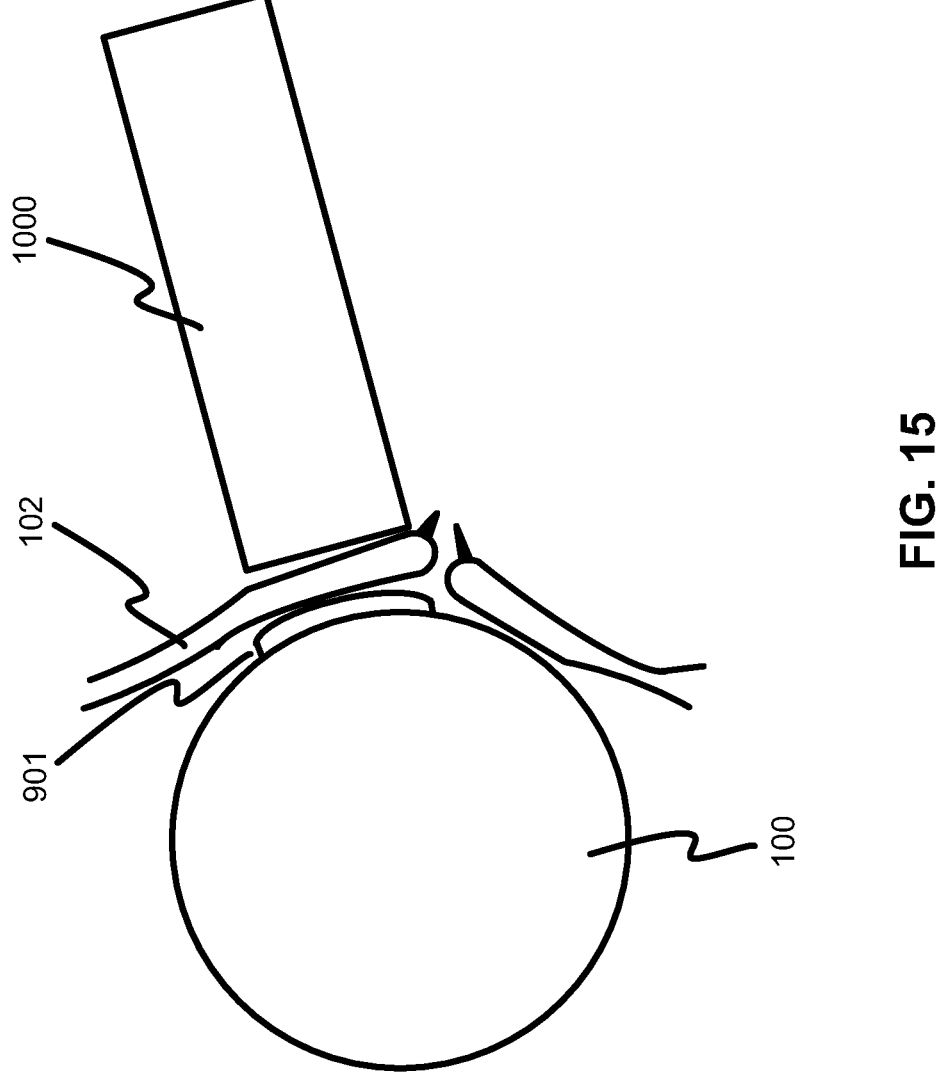
FIG. 15 shows an example of an application using a drug-holding overlay on a surface of the eye.

FIG. 15 shows an example of an application using a drug-holding overlay 901 on a surface of the eye 100, in accordance with embodiments of the invention. An ultrasound-generating device 1000 may be positioned over an eyelid 102 of the eye. In some embodiments, the drug-holding overlay may be positioned on the surface of the eye beneath the eyelid. The drug-holding overlay may be positioned directly beneath the portion of the eyelid that is contacted by the ultrasound-generating device. Alternatively, the drug-holding overlay may be positioned beneath a different portion of the eyelid than the portion that is contacted by the ultrasound-generating device. The ultrasound-generating device may contact a portion of the eyelid when delivering ultrasound. The drug holding overlay may or may not be directly beneath the ultrasound-generating device when the ultrasound-generating device is contacting the eyelid. In some embodiments, the drug-holding overlay may be provided at a completely different portion of the eye. However, the ultrasound signals that may be provided to the eye may still aid in the delivery of drugs from the drug-holding overlay.

The eye may be completely closed or partially closed when the ultrasound-generating device delivers ultrasound to the eyelid.

Optionally, a drug applicator may be operably coupled to the ultrasound-generating device. The drug applicator may be positioned over the eyelid of the eye. The drug applicator may be formed of a low attenuation material that may permit the ultrasound to be transmitted to the eyelid. The drug-holding overlay may or may not be directly beneath the drug applicator. In some embodiments, the drug-holding overlay may be provided on a different region of the eye.

Figures 16A, 16B:
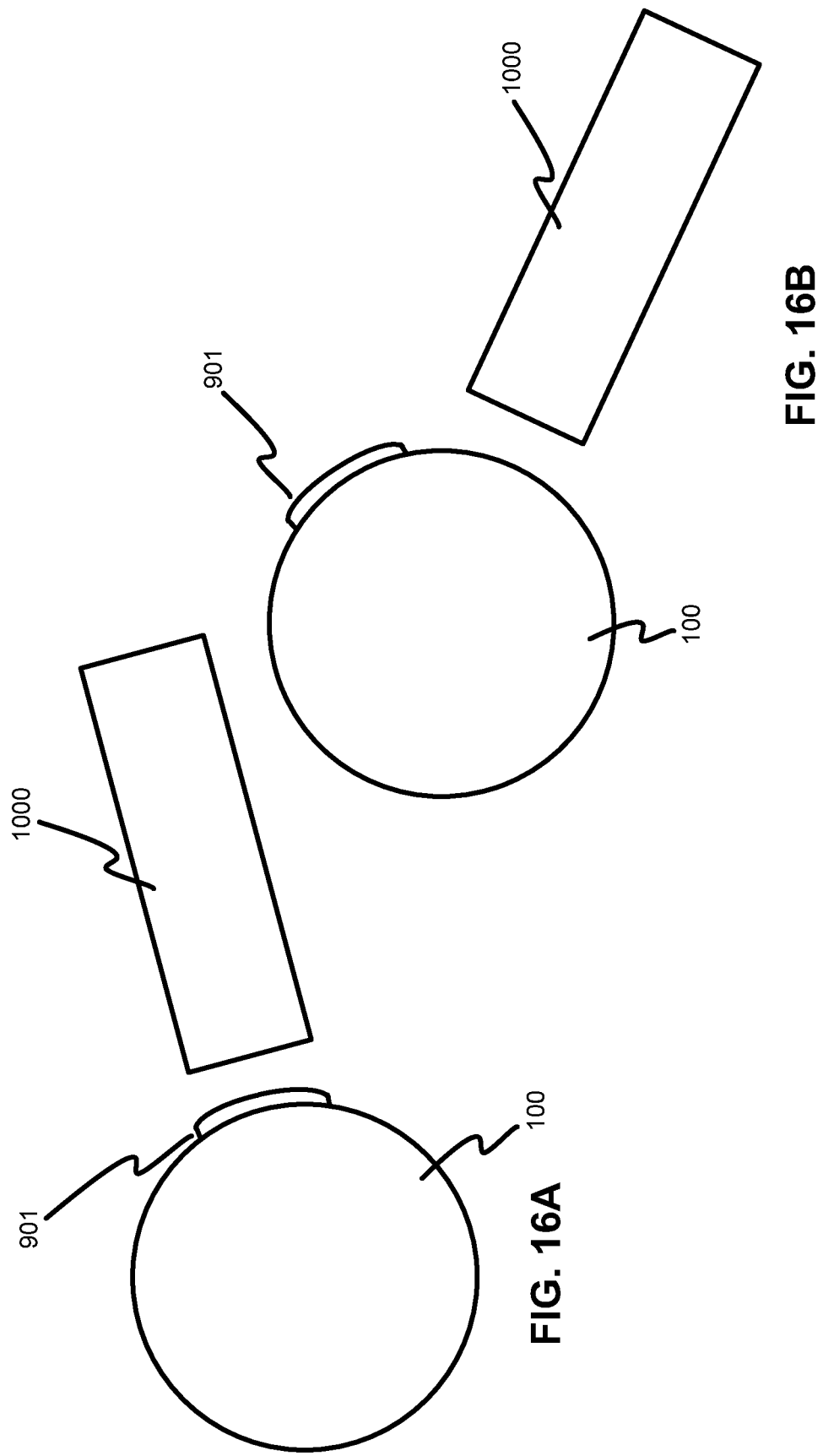
FIGS. 16A to 16B show examples of additional applications using a drug-holding overlay.

FIGS. 16A to 16B show examples of additional applications using a drug-holding overlay 901, in accordance with embodiments of the invention. An ultrasound-generating device 1000 may be positioned over the drug-holding overlay as shown in FIG. 16A, or directly on a surface of the eye 100 while the drug holding overlay is at a different portion of the eye as shown in FIG. 16B. In some embodiments, the drug-holding overlay may be positioned on any portion of the surface of the eye. For instance the drug-holding overlay may be positioned on a sclera, cornea, or limbus of the eye. The ultrasound-generating device may come into contact with the drug-holding overlay when delivering ultrasound. The drug holding overlay may be directly beneath the ultrasound-generating device when the ultrasound-generating device contacting the drug-holding overlay. The ultrasound-generating device may be positioned over a sclera of the eye, cornea of the eye, or limbus of the eye. The drug-holding overlay may be formed from a low attenuation material that may allow the ultrasound from the device to be conveyed to the surface of the eye. This may aid in delivery of the drugs from the drug-holding overlay to a target site of the eye.

In some embodiments, the drug-holding overlay may be provided at a completely different portion of the eye. The ultrasound-generating device may come into direct contact with a surface of the eye. For instance, the ultrasound-generating device may come into direct contact with a sclera, cornea, or limbus of the eye. However, the ultrasound signals that may be provided to the eye may still aid in the delivery of drugs from the drug-holding overlay. The ultrasound-generating device may deliver ultrasound to a different portion of the surface of the eye than the portion of the eye upon which the drug overlay is provided. The ultrasound-generating device may deliver ultrasound to a different portion of the eye than a portion of the surface that receives the drugs.

The eye may be open while the ultrasound-generating device is delivering the ultrasound.

Optionally, a drug applicator may be operably coupled to the ultrasound-generating device. The drug applicator may be positioned over the drug-holding overlay in some embodiments. Alternatively, the drug applicator may directly contact the surface of the eye and the drug holding overlay may be at a different portion of the eye. The drug applicator may be formed of a low attenuation material that may permit the ultrasound to be transmitted to the drug holding overlay and/or the surface of the eye. The drug-holding overlay may or may not be directly beneath the drug applicator. In some embodiments, the drug-holding overlay may be provided on a different region of the eye from the applicator.

In some embodiments, for particular treatment plans, it may be desirable to use the drug-holding overlay which is placed at a desired site of the eye. The drug-holding overlay may optionally be placed for an extended period of time, which may allow long-term delivery of the drugs. The application of ultrasound may provide enhanced delivery. The ultrasound delivery may be provided during the whole time the drug holding overlay is provided to the eye. Alternatively, the ultrasound-delivery may be provided for only a subset of the time that the drug holding overlay is provided to the eye.

Alternatively or in addition, it may be desirable to use ultrasound to provide drainage from the eye, or from a drainage system around the eye. For example, it may be desirable to relieve increased intraocular pressure for certain conditions. In one instance, for treatment of diseases such as glaucoma, where there may be damage to a portion of the eye (e.g., optimal nerve of the eye) due to increased pressure that may result from a blockage of fluid draining from the eye, ultrasound may be applied to aid in drainage of the fluid from the eye. The ultrasound may be used in combination with drugs. For instance, for the treatment of the uveoscleral outflow or to decrease aqueous production, improved delivery of drugs to the target site may aid in the drainage of the fluid and relief from the pressure. Drugs, such as, but not limited to, prostaglandin analogs, beta blockers, adrenergic agents, miotics, carbon anhydrase inhibitors, or any other drugs as provided elsewhere herein, may be delivered to a desired site. Preferably, they may be delivered via a drug applicator to reduce loss of medication by tears, blinking or eye movement (e.g., compared to eye drops).

Ultrasound may be applied which may aid in the delivery of these drugs. In some instances, these drugs may be provided via a drug-holding overlay. The ultrasound-stimulation may help to clear blocked drainage system, which may include an episcleral venous system, aqueous veins, canal of schlemm, and/or trabecular meshwork.

Generation of ultrasound may permit draining of fluid from within the eye to reduce pressure within the eye. The draining of fluid may occur concurrently with delivery of one or more drugs. Draining of fluid may occur prior to delivery of one or more drugs. Draining of fluid may occur subsequent to the delivery of one or more drugs. In some embodiments, the ultrasound may operate at a desired frequency when draining fluid from within the eye. The desired frequency may have any value as provided elsewhere herein. In some instances, the desired frequency may be beneath 1 MHz. In some embodiments, the draining of the fluid may occur without causing any permanent damage to the eye. Optionally, the draining of the fluid may occur by disrupting the intracellular structure of the eye. In some instances, the draining of the eye may occur without increasing the temperature of the eye by a large amount. In some instances, the draining of the eye may occur without raising the temperature of the eye by more than 0.1 degree C., 0.5 degrees C., 1 degree C., 1.2 degrees C., 1.5 degrees C., 1.7 degrees C., 2 degrees C., 2.5 degrees C., 3 degrees C., 4 degrees C., 5 degrees C., 7 degrees C., or 10 degrees C. In some embodiments, the temperature of the eye does not exceed 33 degrees C., 34 degrees C., 35 degrees C., 36 degrees C., 37 degrees C., 38 degrees C., 39 degrees C., 40 degrees C., 41 degrees C., 42 degrees C., 43 degrees C., 44 degrees C., or 45 degrees C. The drainage of fluid may be useful during treatment of reducing intraocular pressure. For example, the drainage of fluid may be useful during glaucoma.

In one example, ultrasound-mediated delivery of glaucoma drug may reach a trabecular meshwork and schlemm's canal. The ultrasound-mediated delivery of the glaucoma drug may occur via the limbus region. Alternatively, the drug may be delivered via other regions, such as the sclera or cornea. The delivery of drugs for treating glaucoma may occur concurrently with reducing aqueous production or increasing liquid outflow. The ultrasound could temporarily disrupt the trabecular meshwork, schlemm's canal and promote fluid outflow, thus reducing intraocular pressure. In some embodiments, high intensity ultrasound (e.g., 1 to 20 MHz) may be applied to reduce intraocular pressure. In some embodiments, the systems and methods provided herein may use lower intensity ultrasound, such as less than 1 MHz, 900 kHz, 800 kHz, 700 kHz, 600 kHz, 500 kHz, 400 kHz, 300 kHz, 250 kHz, 200 kHz, 150 kHz, 100 kHz, 80 kHz, 60 kHz, 50 kHz, 40 kHz, 30 kHz, or 20 kHz to reduce intraocular pressure. In other embodiments, low intensity ultrasound (e.g., with 2-4 W/cm$^2$) may be provided.

A drug delivery device may aid in the delivery of drugs and/or ultrasound to a desired site of the eye. This may allow drugs to be delivered to a target site of the eye, which may include a target site in an intraocular space of the eye. In some embodiments, depending on the drug to be delivered, or a treatment plan to be followed, different parameters may be provided for operation of an ultrasound-generating device of the drug delivery device. Instructions for operation of the ultrasound-generating device may be generated depending on the identity of the drug or a treatment plan for the eye.

Figure 17:
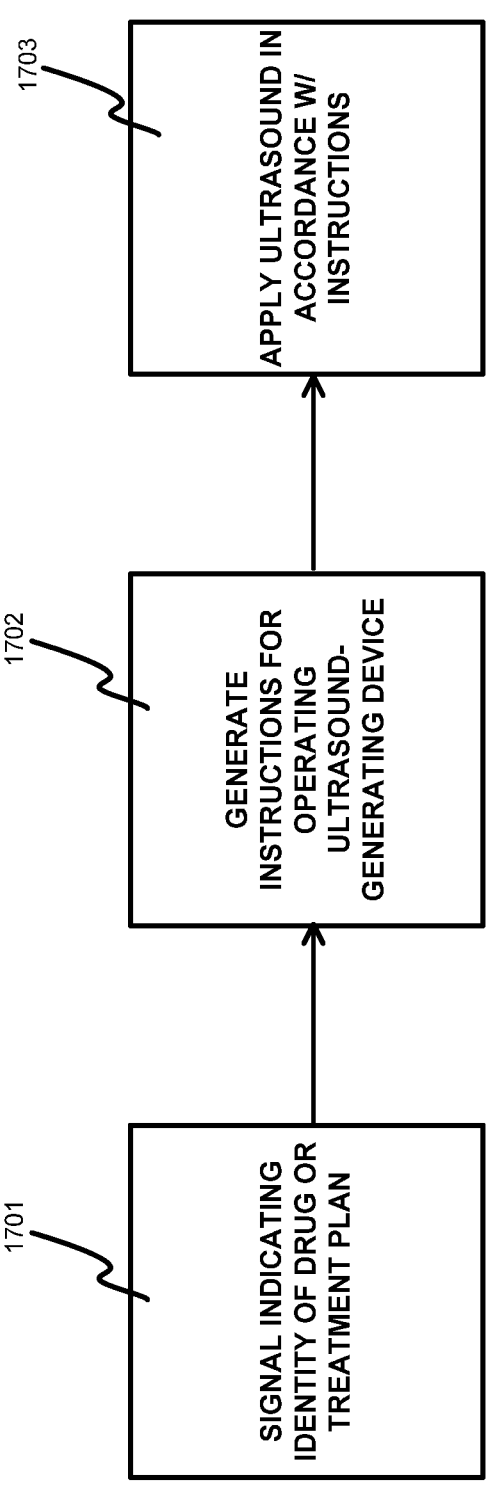
FIG. 17 shows an example of a process for generating instructions for operation of an ultrasound-generating device.

FIG. 17 shows an example of a process for generating instructions for operation of an ultrasound-generating device. A method of generating instructions for delivery of the drug may comprise obtaining a signal indicative of an identity of the at least one drug to be delivered or an identity of a treatment plan for the eye 1701. The method may also comprise generating instructions operation of the ultrasound-generating device, based on the signal indicative of the identity of the drug or treatment plan 1702. Ultrasound may be applied in accordance with the instructions, which may effect delivery of the drug 1703.

A signal indicative of an identity of the at least one drug to be delivered or an identity of a treatment plan for the eye may be obtained 1701. The signal may be received at a drug delivery device, a display and/or input device, or a separate device. In some embodiments, the signal may be provided in response to a user input. The user input may be an input of an identity of the drug (e.g., a name of the drug, a selection of the drug from a plurality of drugs, a batch number or other identifier of the drug, a type of drug). The user input may be an input of an identity of a treatment plan for the eye. The identity of the treatment plan may comprise an identity of a disease or condition that is being treated for the eye (e.g., glaucoma, macular degeneration, diagnostic, vitamin delivery, prophylactics, or any other disease or condition as described elsewhere herein). The identity of a treatment plan may include a specific treatment plan identifier (e.g., name of plan, alphanumeric string identifying the plan, type of plan) which may or may not be unique for a particular subject or type of subject. A specific treatment plan for a subject may be generated with aid of a medical practitioner treating the subject. A specific treatment plan for the subject may be generated with aid of one or more processors based on certain inputs about the subject's conditions.

In some embodiments, a user may be able to access settings for a disease/condition to be treated, ultrasound intensity, ultrasound frequency, cycle time, start, stop and/or timer. The user may be able to input or view patient information and/or a profile. For instance, the patient's name, medical records, disease/condition, stage of treatment, picture, may be accessed. In some instances, a user input may just be a patient identity, and the disease identity and/or treatment identity may be pulled from the patient's records. In some instances, the user input may just be the disease identity and/or treatment identity and the device or system may automatically generate operating parameters for the ultrasound-generating device. Alternatively, a user may manually adjust the operating parameters for the ultrasound-generating device, such as frequency, mechanical index, intensity, cycle time, cycle number, wait time, etc.

The user input may be provided via a user interface. The user interface may be on-board the drug delivery device. For example, the user may directly input the identity of the drug and/or treatment plan directly into the drug delivery device. In another example, the user may interact with a display and/or input device which may be part of the drug delivery device or provided separately from the drug delivery device. In some instances, the display and/or input unit may communicate with the drug delivery device. The user input may be provided from any other external device. For example, the user may provide an input into a device, such as a computer, tablet, or smartphone, that may be in communication with the drug delivery device.

In some embodiments, the signal indicative of the identity of the drug or identity of the treatment plan may be provided from one or more processors. The identity of the drug or identity of the treatment plan may be provided on a label of a drug applicator that may be coupled to the device. The drug applicator may be pre-loaded with at least one drug. The drug applicator may be coupled to the device in a removable fashion. When the drug applicator is coupled to the device, a sensor may be used to read the label of the drug applicator. Further details of reading the label from the drug applicator are provided in greater detail elsewhere herein. The label may provide information such as identity of the drug, volume of drug, identity of treatment plan, length of time for the treatment plan, specifics of the treatment plan, disease to be treated, identity of the subject, batch, time of manufacture, location of manufacture, manufacturer ID, expiration date, or other information relating to the drug applicator and/or drug. The information may be directly provided by the label, or the label may allow the drug delivery device to access a memory that may store the information. For example, if a treatment plan identifier is provided, the drug delivery device may access a memory storage on-board or off-board the device. The memory storage may have the additional information associated with the treatment plan identifier.

In some embodiments, the drug applicator may 'push' information, such as the identity of the drug or treatment plan to the drug delivery device. For instance, the drug applicator may broadcast information, such as the identity of the drug or treatment plan, which may be read by a communication unit of the drug delivery device.

One or more processors may be used to generate instructions for operation of the ultrasound-generating device based on the signal indicative of the identity of the drug or treatment plan 1702. The processors may be on-board the drug delivery device. Alternatively, the processors may be off-board the drug delivery device. The processors may optionally be on-board a display and/or input device. The processors may be provided at a separate device. The processors may be provided as part of a cloud computing infrastructure.

Generating instructions may comprise selecting instructions from a plurality of instruction options for various drugs or treatment plans. For example, a first set of instruction options may be provided for a first drug or treatment plan. A second set of instructions different from the first set of options may be provided for a second drug or treatment plan. A pre-set universe of sets of instructions may be provided. Based on which drug or treatment plan was identified, the appropriate set of instructions corresponding to the identified drug or treatment plan may be selected.

In other instances, the instructions may be generated de novo and not selected from an existing pool of instructions. The instructions may be generated based on known parameters of the drugs and/or treatment plans. The instructions may be generated based on a subject's identity or characteristics of the subject. For example, if the subject is a 40 year old female, the instructions may be different from if the subject is a 60 year old male. If the subject has any known interactions with drugs, this may affect the instructions as well. For example, Person A may be more sensitive to drug A than Person B.

The instructions may define operation of the ultrasound-generating device. This may include determining the frequency of the ultrasound, the mechanical index of the ultrasound, timing information for the ultrasound (e.g., a time duration TA of the ultrasound, a waiting period TW of the ultrasound, a number of duty cycles of the ultrasound, a length of the treatment plan of the ultrasound), a wave form of the ultrasound, and/or an intensity of the ultrasound.

The ultrasound may be generated in accordance with the instructions 1703. The generation of the ultrasound may effect delivery of drugs to the target site. In some embodiments, the ultrasound may be applied prior to, concurrently with, and/or subsequent to the drug applicator making contact with the eye.

Further embodiments of the invention relate to integration of the system according to one aspect of the invention into existing treatment apparatuses for diseases of the eye. The system is preferably combined and/or integrated with other diagnostic and/or treatment devices.

Figures 18A, 18B, 18C:
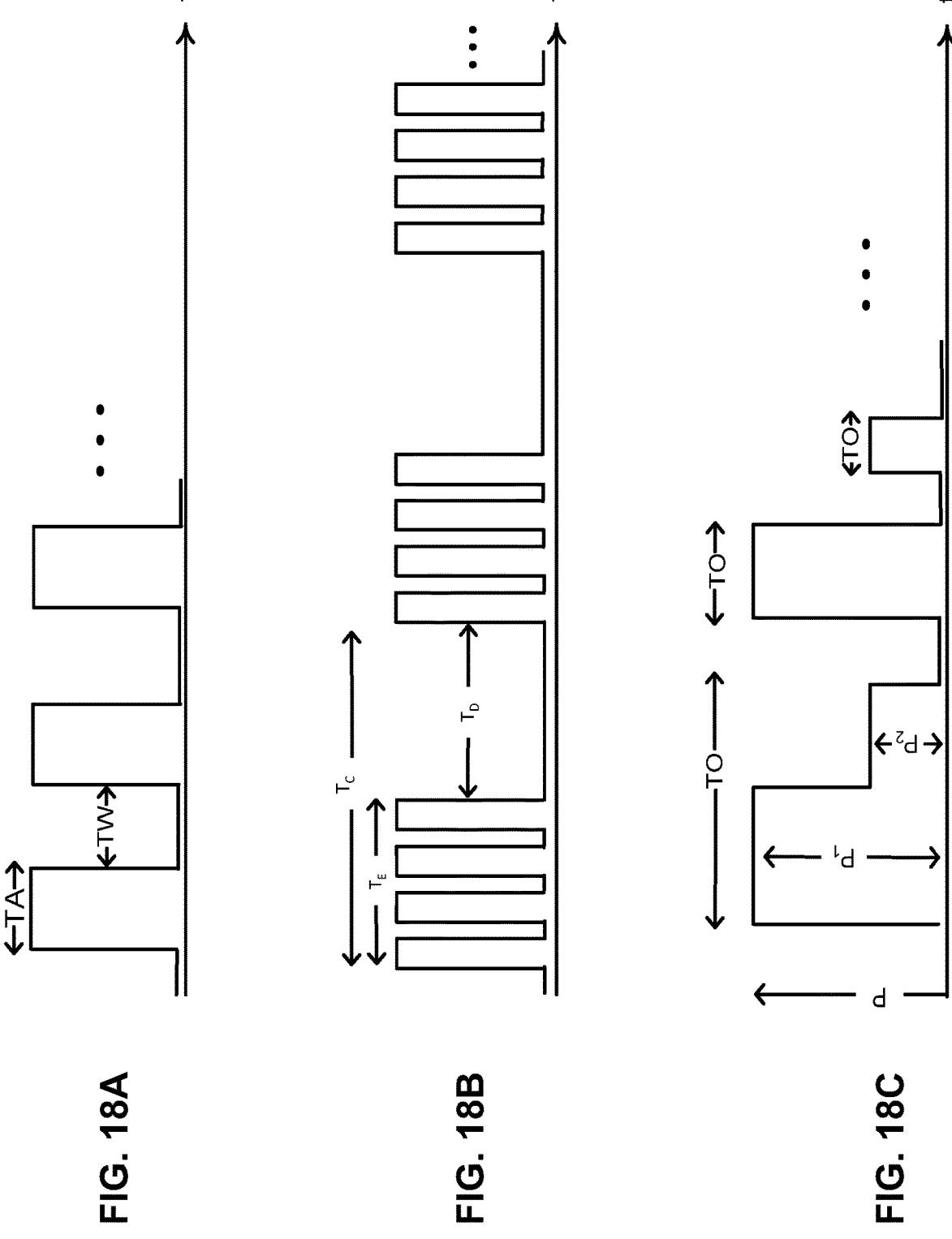
FIGS. 18A to 18C show examples of application of ultrasound in accordance with various treatment plans.

FIGS. 18A to 18C show examples of application of ultrasound in accordance with various treatment plans.

FIG. 18A shows examples of ultrasound that may be applied in accordance with a treatment plan. The ultrasound may be delivered in pulses of on and off. The system may be operated in at least one application cycle. Each application cycle comprises at least one ultrasound emitting event with a time duration TA and a subsequent waiting period with a time duration TW. During the ultrasound emitting event the ultrasound device is operated and during the waiting period the ultrasound device is not operated. The drug applicator may be in contact with a surface of the eye such as a scleral surface, corneal surface, or limbus, for the complete duration of the at least one application cycle.

Depending on the physical, chemical, and pharmaceutical properties of the drug different parameters for the application cycle are required. In one embodiment of the invention the system is configured to control at least one parameter, preferably a subset, selected from the following list: the time duration TA of the ultrasound emitting event, the time duration TW of the wait period after the ultrasound emitting event, the number of application cycles, the intensity of the ultrasound emitting event, the central frequency of the ultrasound emitting event, the mechanical index of the ultrasound emitting system, and in case of a pulsed ultrasound emitting event: the repetition rate of the ultrasound emitting event and the duty cycle of the ultrasound emitting event.

Any number of application cycles may be provided. In some embodiments, a preset number of application cycles may be provided. In some instances, a preset duration for the application cycles to run may be provided.

FIG. 18B shows an example of multiple application cycles that may be clustered together, in accordance with embodiments of the invention. The clusters of cycles may or may not be repeated. In some embodiments, a cluster may have a length of time Tc. The length of the application cycles may collectively be about TE. The amount of time between the clusters may be a dormant period TD. The clusters may repeat any number of times. The clusters may repeat for a predetermined number of times, or during a preset duration.

FIG. 18C shows an example of how parameters P may be varied over time/during a treatment plan. There may or may not be regular application cycles. In some embodiments, a series of application cycles with various characteristics may repeat, or may not repeat. For example, an amount of time that the ultrasound is 'on' To may be fixed or may vary. A waiting period Tw during which the ultrasound is 'off' may be fixed or may vary. Similarly, a cluster length TE may be fixed or may vary. Time between clusters Tp may be fixed or may vary.

One or more parameters may be fixed for a particular application cycle. One or more parameters may be fixed for an entirety of a cluster. One or more parameters may be fixed for an entirety of a treatment plan. Alternatively, one or more parameters may be varied during a treatment plan. One or more parameters may be varied during a cluster. One or more parameters may be varied during an application cycle. Any parameter may be varied including, but not limited to, intensity of the ultrasound emitting event, the central frequency of the ultrasound emitting event, or the mechanical index of the ultrasound emitting system.

For any of the times (e.g., TA, TW, TC, TD, TE), the amount of time may be on the order of microseconds, milliseconds, seconds, tens of seconds, minutes, or more. For instance, ultrasound may be generated for a time duration of less than or equal to about 0.001 s, 0.005 s, 0.01 s, 0.05 s, 0.1 s, 0.5 s, 1 s, 3 s, 5 s, 10 s, 15 s, 20 s, 30 s, 45 s, 60 s, 90 s, 120 s, 150 s, 180 s, 210 s, 240 s, 270 s, 300 s, 360 s, 420 s, 480 s, 540 s, 600 s, 1000 s, 2000 s, 3000 s, or 6000 s. Ultrasound may be generated for a time duration greater than any of the values provided herein or within a range falling between any two of the values provided herein. Similarly, a wait time may be provided for a time duration less than or equal to any time duration provided herein. A wait time may be greater than any time duration provided herein, or falling within a range between any time durations provided herein. Any other time associated with the ultrasound treatment profile (e.g., TC, TD, TE) may have a time duration less than, greater than, or falling between any two of the time durations provided herein. In some embodiments, an entire treatment plan may span on the order of seconds, minutes, hours, days, weeks, months, or years. A patient may receive ultrasound treatment at different points in time and may be re-acquainted with a drug delivery system as needed.

For different drugs and/or treatment plans different ultrasound profiles may be provided over time.

Figure 19:
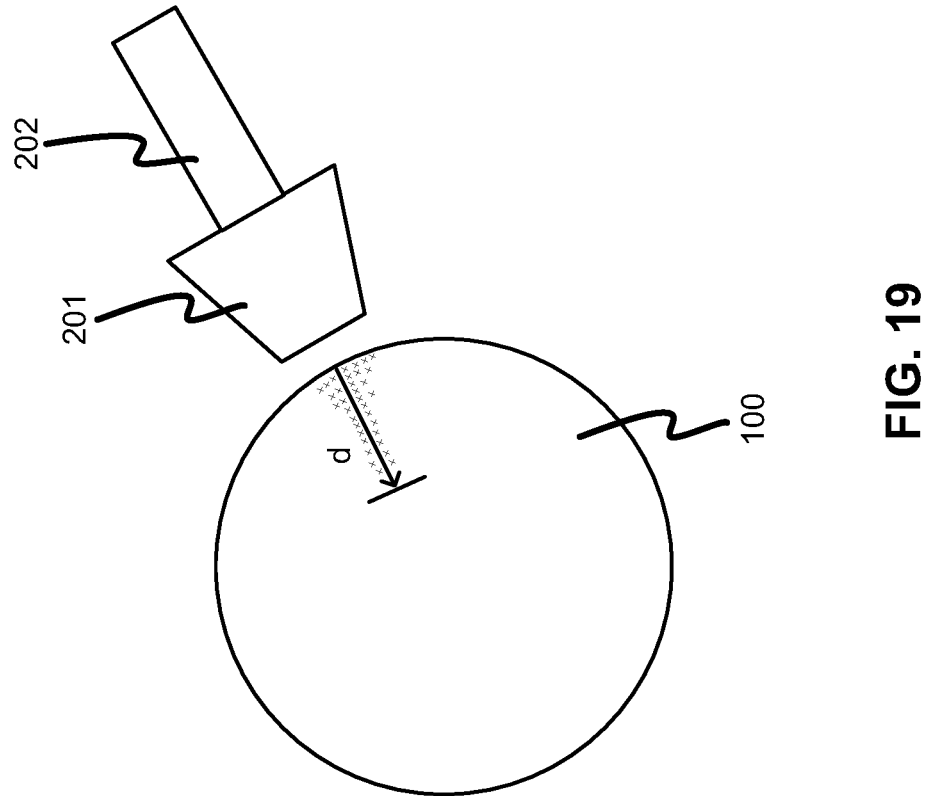
FIG. 19 shows an example of penetration of drugs to a target site within an intraocular space of the eye.

FIG. 19 shows an example of penetration of drugs to a target site within an intraocular space of the eye, in accordance with embodiments of the invention. An ultrasound-generating device 202 and drug applicator 201 may deliver drugs and ultrasound to an eye 100. The ultrasound-generating device may advantageously permit penetration of drugs to a distance d within the eye.

In some embodiments, it may be desirable to for the drug to penetrate to a posterior part of the eye. For example, for diseases such as diabetic retinopathy or macular degeneration, the drugs may be delivered to the posterior part of the eye. In some embodiments, the drugs may be corticosteroid or anti-VEGF drugs. Some of the drugs may include, but are not limited to triamicolone with trade names of aristocort, kencaort, or kenalog, or anti-VEGF with trade names of lucentis, eylea, or avastin. Through the ultrasound treatment as described herein, the drugs may be delivered to the back side of the eye, the retina. The concentration at which the drugs may be delivered may be the same, or at least 50%, 60%, 70%, 80%, 90%, 95%, 97%, or 99% of the drug concentrations provided with intravitreal injections without requiring such invasive techniques.

The drug may be capable of penetrating to a depth d of at least 4 cm, 3.5 cm, 3 cm, 2.5 cm, 2 cm, 1.5 cm, 1 cm, 0.8 cm, 0.7 cm, 0.6 cm, 0.5 cm, 0.4 cm, 0.3 cm, 0.2 cm, or 0.1 cm. Such distance may be penetrated when the ultrasound is operating at any frequency value, such as less than or equal to 1 MHz, 900 kHz, 800 kHz, 700 kHz, 600 kHz, 500 kHz, 400 kHz, 300 kHz, 250 kHz, 200 kHz, 150 kHz, 120 kHz, 100 kHz, 90 kHz, 80 kHz, 70 kHz, 60 kHz, 50 kHz, 40 kHz, 30 kHz, 20 kHz, or 10 KHz. Such a distance may be penetrated when the ultrasound is operating at a frequency value greater than any of the values provided, or falling within a range between any two of the values provided. Such distance may be penetrated when the ultrasound is operating at any mechanical index, such as less than or equal to 0.01, 0.05, 0.1, 0.13, 0.15, 0.17, 0.18, 0.19, 0.2, 0.21, 0.22, 0.23, 0.24, 0.25, 0.3, 0.35, 0.4, 0.45, 0.5, 0.6, 0.7, 0.8, 0.9. Such a distance may be penetrated when the ultrasound is operating at a mechanical index greater than any of the values provided, or falling within a range between any two of the values provided. Such distance may be penetrated when the ultrasound is operating at any intensity, such as less than or equal to 10, 9, 8, 7.5, 7, 6.5, 6, 5.5, 5, 4.5, 4, 3.5, 3, 2.5, 2, 1.5, 1, 0.5, 0.1 W/cm$^2$. Such a distance may be penetrated when the ultrasound is operating at a mechanical index greater than any of the values provided, or falling within a range between any two of the values provided. The drug may be capable of penetrating to any of the depths indicated within 600 seconds, 480 seconds, 420 seconds, 360 seconds, 300 seconds, 240 seconds, 180 seconds, 120 seconds, 90 seconds, 60 seconds, 30 seconds, 20 seconds, 15 seconds, 10 seconds, 5 seconds, 3 seconds, 2 seconds, 1 second, 0.5 seconds, or 0.1 seconds. The drug may be capable of penetrating to such depths within any of the indicated time values of the ultrasound being applied. The drug may be capable of penetrating to such depths within any of the indicated time values of the drug applicator making contact with a surface of the eye. The drug may be capable of penetrating to a maximum depth that the drug may travel within any of the time values provided.

The drug may be configured to penetrate to a target site at any concentration. In some embodiments, the drug may delivered into the vitreous and the retina of the eye at any concentration. The drug may be delivered to a target site at a concentration of greater than or equal to 0.01, 0.05, 0.1, 0.3, 0.5, 0.7, 1, 1.2, 1.3, 1.4, 1.5, 1.6, 1.7, 1.8, 2, 2.5, 3, 3.5, 4, 5, 7, 10, 12, 15, 17, 20, 25, 30, 35, 40, 50, 60, 70, 80, 100, 150, 200, 250, 300, 400, 500, 700, 1000, 1200, 1500, 2000, 2500, 3000, 3500, 4000, 5000, 7000, 10000 μg/mL. The drug may be delivered at a concentration less than any of the values provided or falling within a range between any two of the values provided. The drug may be capable of penetrating at any speed. The drug may be capable of being delivered at a speed of at least 5, 10, 20, 30, 40, 50, 60, 70, 80, 90, 100, 110, 120, 130, 150, 175, 200, 250, 300, 350, 400, 450, 500, 600, 700, 800, 900, 1000 μm$^2$/s.

The drugs that may be penetrating to such depths may be any type of molecule. The drugs may be penetrating to such depths under such ultrasound frequencies, intensities, or mechanical indexes. The drugs may be penetrating under any such concentrations or at any such speeds. The drugs may be penetrating to such depths within the time periods indicated. Such penetration may occur without damaging the eye tissue (e.g., sclera, retina, cornea, limbus). Such penetration may occur without damaging the eye tissue in a permanent manner. Such penetration may occur without increasing temperature of the eye by more than 0.1 degrees, 0.5 degrees, 1 degree, 1.5 degrees, 2 degrees, 2.5 degrees, 3 degrees, 3.5 degrees, 4 degrees, 5 degrees, 6 degrees, 7 degrees, 8 degrees, 9 degrees, or 10 degrees C., or any other temperature value provided elsewhere herein. Such penetration may occur without causing the temperature of the eye to rise beyond 33 degrees, 34 degrees, 35 degrees, 36 degrees, 37 degrees, 38 degrees, 39 degrees, 40 degrees, 41 degrees, 42 degrees, 43 degrees, 44 degrees, or 45 degrees C.

The drug molecules may be small organic molecules, proteins, monoclonal antibodies, antibody fragments, or nanoparticles. Any size of molecule may be delivered to the target site. In some embodiments, the size of the molecules may be less than or equal to about 10 Da, 50 Da, 100 Da, 300 Da, 500 Da, 700 Da, 900 Da, 1 kDa, 2 kDa, 3 kDa, 5 kDa, 7 kDa, 10 kDa, 20 kDa, 30 kDa, 40 kDa, 50 kDa, 60 kDa, 70 kDa, 80 kDa, 90 kDa, 100 kDa, 120 kDa, 150 kDa, 170 kDa, 200 kDa, 220 kDa, 250 kDa, 280 kDa, 300 kDa, 350 kDa, 400 kDa, 450 kDa, 500 kDa, 600 kDa, 700 kDa, 800 kDa, 900 kDa, or 1 MDa. In some instances, the size of the molecules may be greater than any of the sizes provided herein. The size of the molecules may fall within a range between any two of the sizes provided herein.

The size of the molecules comprising the drug to be delivered may be important for the parameters of the application cycle. For relatively small molecules, i.e., preferably having a size of less than 70 kDa, the drug delivery rate is primarily controlled by the duration of the ultrasound emission event TA. For relatively large molecules, i.e., preferably having a size of more than 70 kDa, the drug delivery rate is primarily controlled by the duration of the wait time TW after the ultrasound emission event.

Since the optimal set of parameters of the application cycle varies for different drugs and/or different users, in it is preferred that the system comprises one or more processors for assisting the setting of parameters of the application cycle. The information sending and/or receiving unit 203 may be used to retrieve information about the drug from the drug applicator 201. The display and input unit 400 may be provided to allow for changing of preset parameters.

In an embodiment of the invention, the system is connected to a central database and the database manages information about optimal sets of parameters of the application cycle. The database may be provided on a cloud computing infrastructure. One or more drug delivery devices may be capable of communicating with the database. For instance, a drug delivery device may receive instructions about an optimal set of parameters for a particular treatment plan, drug, and/or patient. The drug delivery device may send information to the database about a drug, treatment plan and/or patient and the database may return the optimal set of parameters. Alternatively or additionally, optimal sets of parameters of the application cycle are stored on/in the drug applicator and are preferably retrieved by the information sending and/or receiving unit 203. In some embodiments, the optimal sets of parameters on-board the drug delivery device. The optimal sets of parameters may be updated periodically or in response to an event from the central database.

In an embodiment of the invention, the system comprises input means configured to manually set the parameters of the application cycle.

The system according to one aspect of the invention is configured to carry out the method according other aspects of the invention. In the following aspects of preferred embodiments of the method for ultrasound enhanced delivery of drugs are described. The skilled person realizes that certain above described embodiments of the system relate to certain embodiments of the method described hereinafter.

In an embodiment of the invention, the drug to be delivered is stored in the drug applicator 201. Prior to the delivery operation the drug applicator 201 is coupled to the application head 205. Prior to the coupling, a used drug applicator 201 is required to be removed. Prior or after the coupling the drug applicator 201 is prepared for the delivery operation. Preparing for the delivery operation preferably comprises removing a peel-off seal and/or removing a protective cover.

In an alternative embodiment, the drug is stored in a container holding several doses of the drug. A drug applicator 201 is preferably permanently coupled to the application head 202 and/or a drug applicator 201 is coupled to the application head 202. The drug applicator 201 is optionally cleaned prior to loading the drug into the drug applicator 201. After the optional cleaning the drug is loaded into a drug receiving space 800 in the drug applicator 201. The loading can be carried out while the drug applicator 201 is attached to the application head 205 or while the drug applicator 201 is not attached to the application head 205.

In an embodiment of the invention, after the drug applicator 201 has been prepared for the delivery operation the system is prepared for the delivery operation. In an alternative embodiment of the invention the system is prepared for the delivery operation prior to preparing the drug applicator 201 for the delivery operation. Preparing the system for the delivery operation preferably comprises setting the optimal set of parameters of the application cycle and/or adapting the parameters of the application cycle. Prior to setting and/or adapting the parameters of the application cycle information about the drug and/or information about the drug applicator 201 are preferably retrieved by the information sending and/or receiving unit 203.

In an embodiment of the invention, after the system and/or the drug applicator 201 have been prepared for the delivery process the system is positioned such that the drug applicator touches the scleral surface. In an alternative embodiment, the system is positioned prior to preparing the system and/or the drug applicator.

Positioning the system preferably comprises applying an ultrasound transmission gel to an interface 601*b* between the drug applicator 201 and the scleral surface. Positioning the system alternatively or additionally comprises pressing the drug applicator 201 against the scleral surface.

In an embodiment of the invention, after the system has been positioned the at least one application cycle is performed. During the application cycle the drug applicator 201 is in permanent contact with the sclera surface.

In an embodiment of the invention, during the at least one application cycle the temperature of the sclera surface is measured this measurement means. Measurement means preferably include a thermocouple and/or an infrared thermometer. It is preferred that the temperature of the scleral surface does not increase by more than 1° C. during the at least one application cycle. The system is preferably configured to control the ultrasound emission event to prevent excessive heating of the scleral tissue.

In an embodiment of the invention, after the at least one application cycle and additional wait time is required for the drug to be delivered most efficiently.

In an embodiment of the invention after the at least one application cycle the drug applicator 201 is removed from the scleral surface. Depending on the embodiment of the invention the drug applicator 201 is preferably configured to be reused at a later time or is configured to be a single use drug applicator 201. Depending on the embodiment of the invention the drug applicator 201 is removed from the application head 205 after the at least one application cycle and/or remain on the application head 205 for later use.

Figure 20:
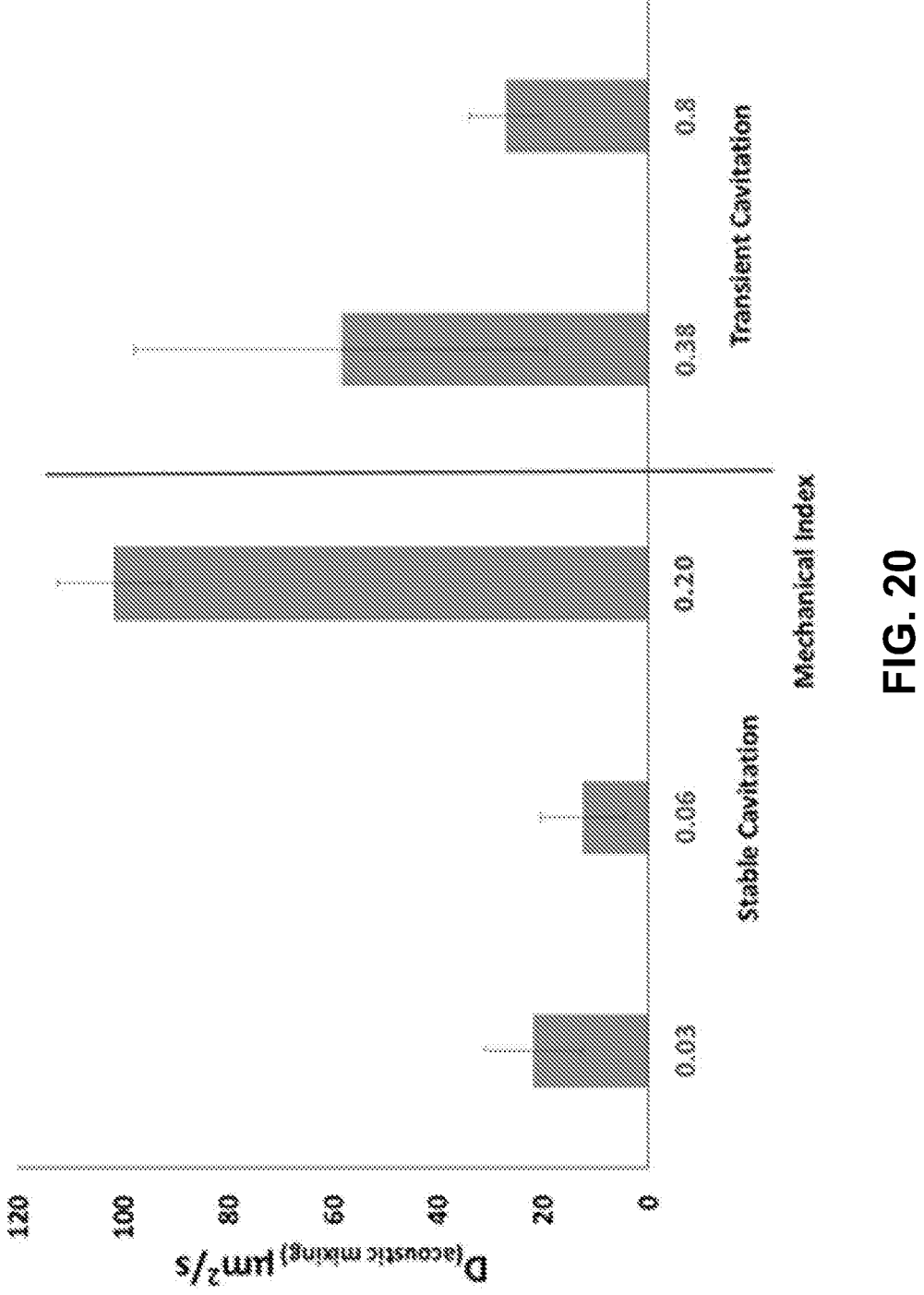
FIG. 20 shows effects of various mechanical indexes.

FIG. 20 shows effects of various mechanical indexes, in accordance with embodiments of the invention. For instance, different values for diffusivity (e.g., D) acoustic mixing of BSA) are provided for various mechanical indices. Such values are provided during 30 s 40 kHz ultrasound application N>=3. An error bar is provided that represents the standard deviation of the fitted diffusivity values. The highest degree of diffusivity may be provided for a mechanical index of 0.2.

Figure 21:
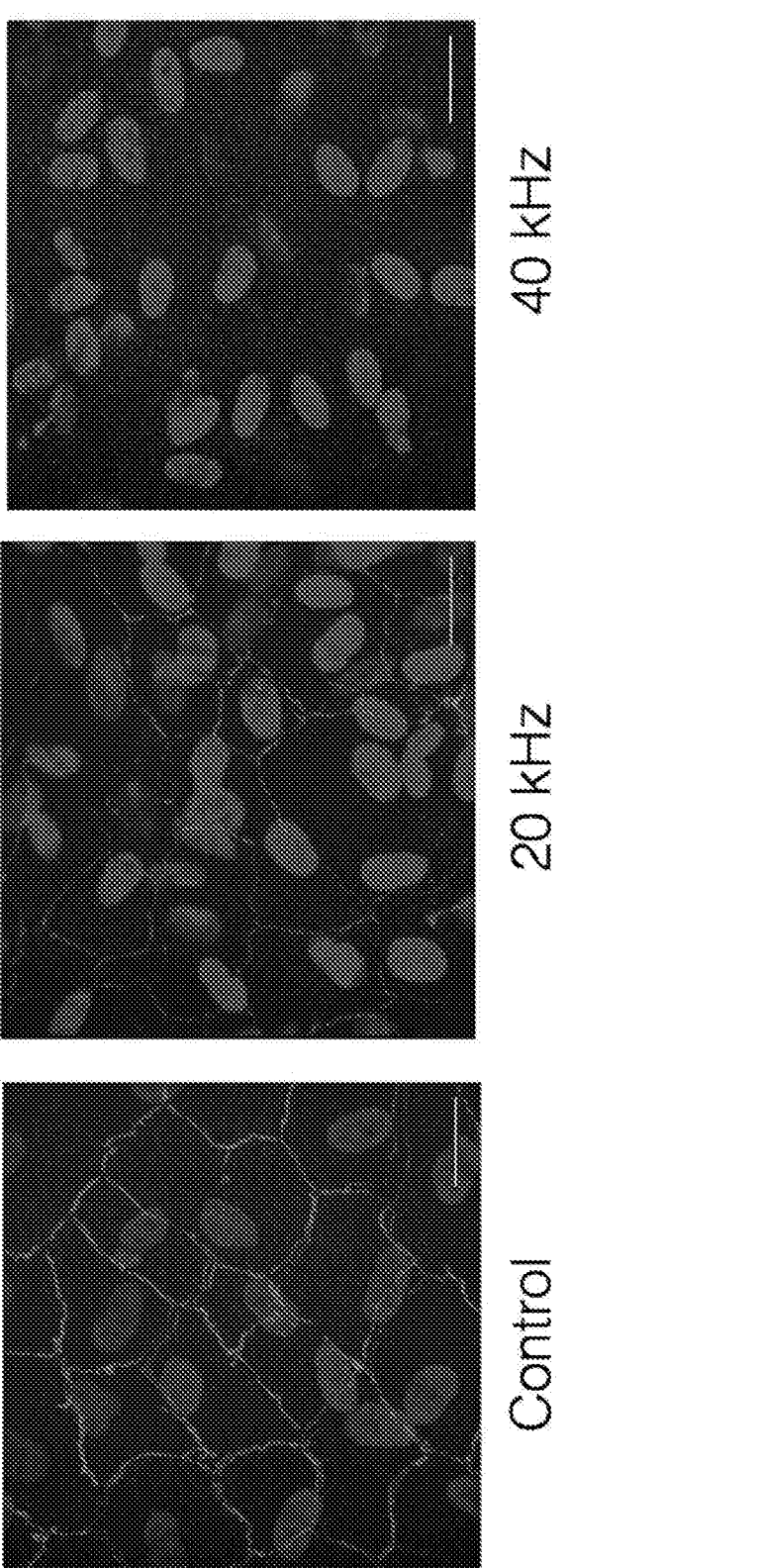
FIG. 21 shows how various frequencies affect intracellular junctions.

FIG. 21 shows how various frequencies affect intracellular junctions, in accordance with embodiments of the invention. For instance, using a 20 kHz ultrasound at a mechanical index=0.2 allows drug molecules (e.g., any type of molecules with any characteristics or parameters as provided elsewhere herein) to be delivered into the surface of the eye (e.g., the sclera, cornea, limbus) and/or suprachoroidal space, but not crossing the retina. The drug molecules may be delivered at any speed, such as any of the values described elsewhere herein, without damaging the eye tissue.

Tight junction staining images are provided, which shows that at 20 kHz, the ultrasound does not disrupt the tight junctions of the retinal epithelium cells. At 40 kHz, ultrasound disrupted all the intercellular junctions. With the intercellular junctions intact, drug molecules cannot pass through the epithelial cell layer, and thus remain in the suprachoroidal space.

Figure 22:
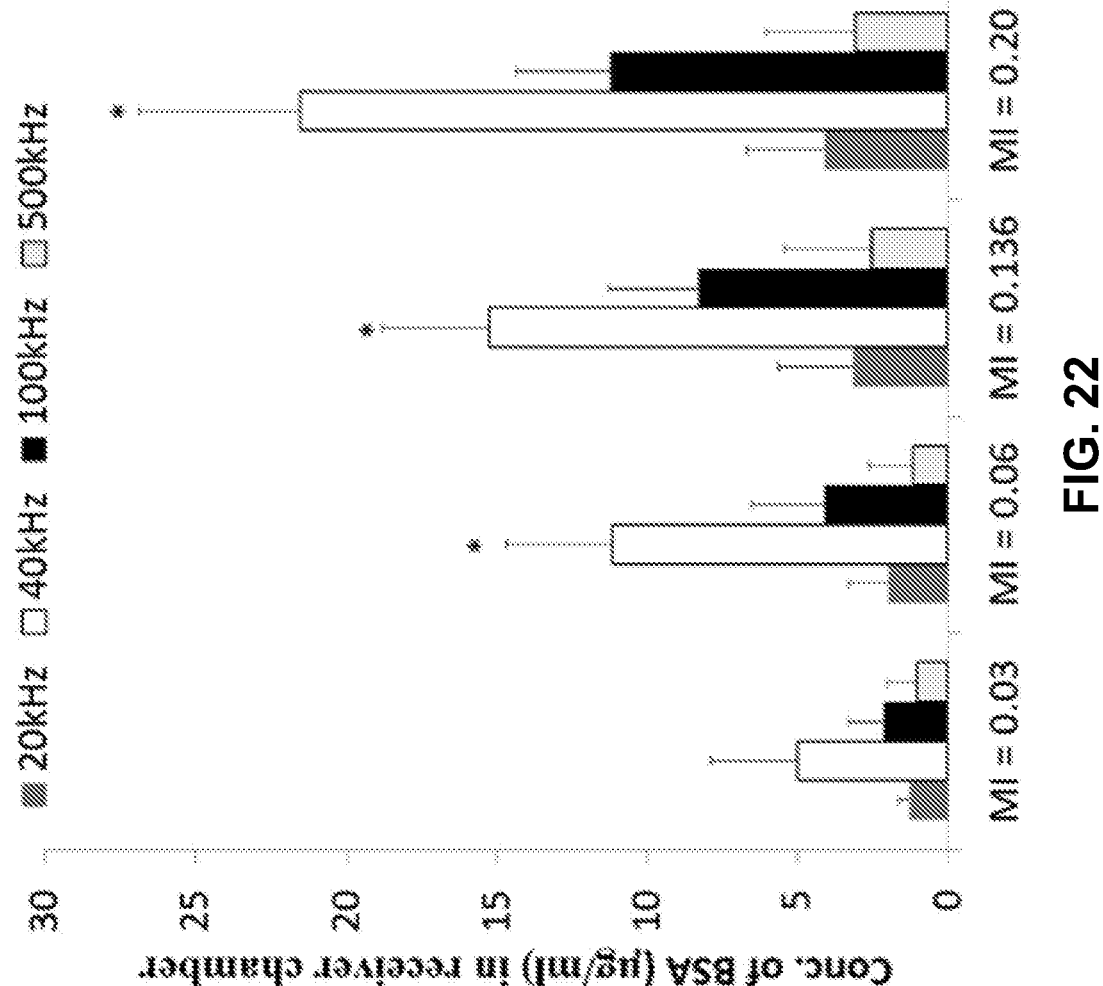
FIG. 22 shows additional effects of various mechanical indexes and frequencies.

FIG. 22 shows additional effects of various mechanical indexes, in accordance with embodiments of the invention. Concentration of BSA in a receiver chamber is shown for various mechanical indexes and frequencies.

FIG. 23 shows further examples of effects of various mechanical indexes, in accordance with embodiments of the invention. At various mechanical indexes, different changes in BSA partition relative to control may be provided. In some embodiments, mechanical indexes of different cavitation regimes may be provided. For instance, lower mechanical index values may correspond to sable cavitation and higher mechanical indexes may correspond to transient cavitation.

Figure 24:
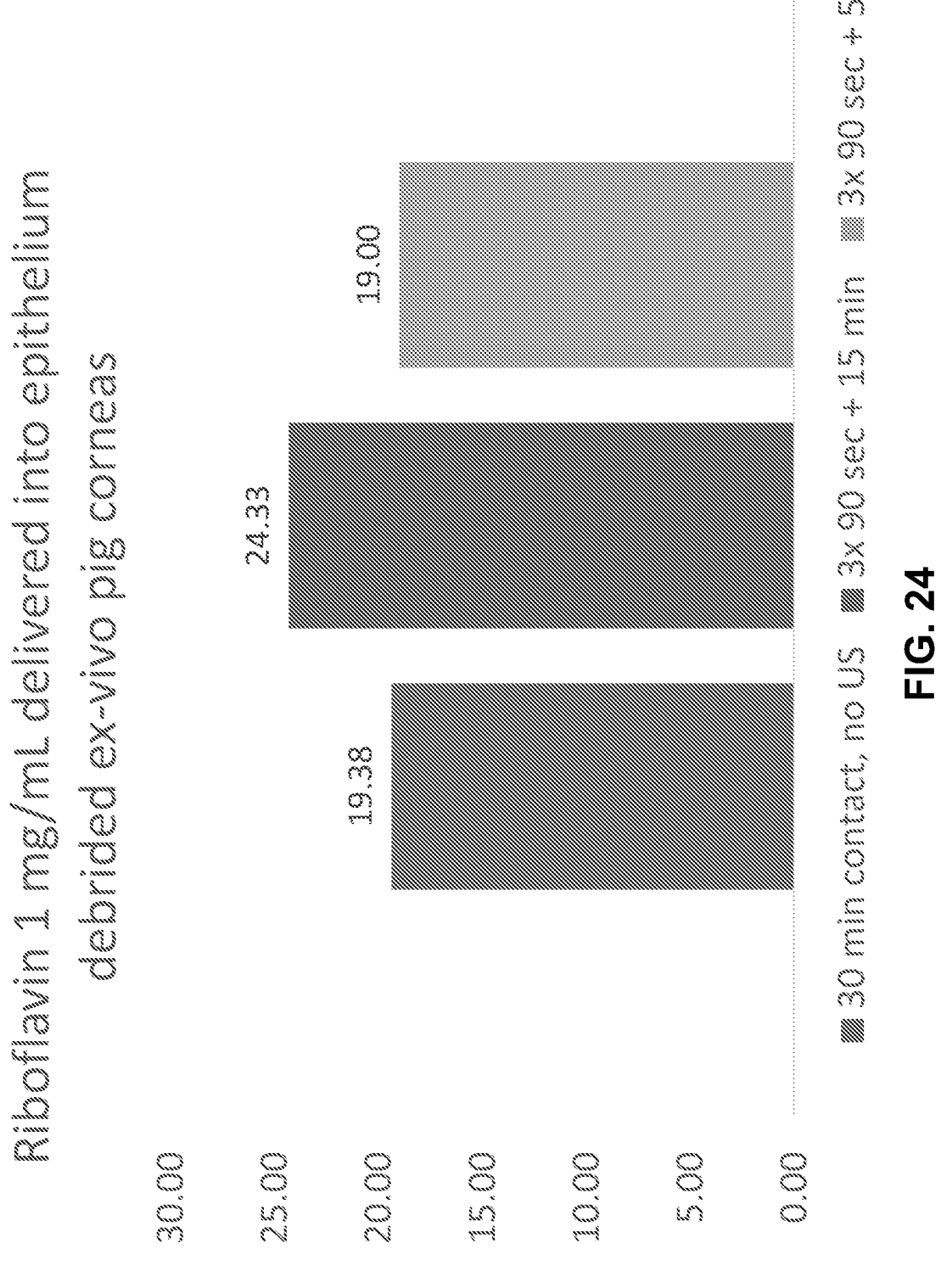
FIG. 24 shows examples of data pertaining to riboflavin delivery to a target site.

FIG. 24 shows examples of data pertaining to riboflavin delivery to a target site. For example, a riboflavin molecule may be delivered into a cornea by ultrasound. An ex vivo study was conducted of delivering small molecules into porcine corneal tissue. The small molecules used was riboflavin. The small molecules may have a molecular weight of about 376 g/mol or less. By using ultrasound at 40 kHz, at least 15 µg/mL of riboflavin was delivered into the deep corneal stromal tissue.

An illustration is provided of riboflavin 1 mg/mL delivered into ex vivo pig corneas. The riboflavin concentration in µg/mL is shown for different circumstances, such as epithelium debrided (Epi-off) cornea with 30 minutes riboflavin contact, Epi-Off with 3 cycles of 90 seconds ultrasound +15 minutes breaks in between and Epi-Off with 3 cycles of 90 seconds ultrasound+5 minutes break in between. 0.1% Riboflavin solution, Peschke D was delivered in ex-vivo pig corneas. The 15 µg/mL safety threshold is exceeded by applying 3 cycles of 90 seconds ultrasound with 5 minute breaks in between.

Figure 25:
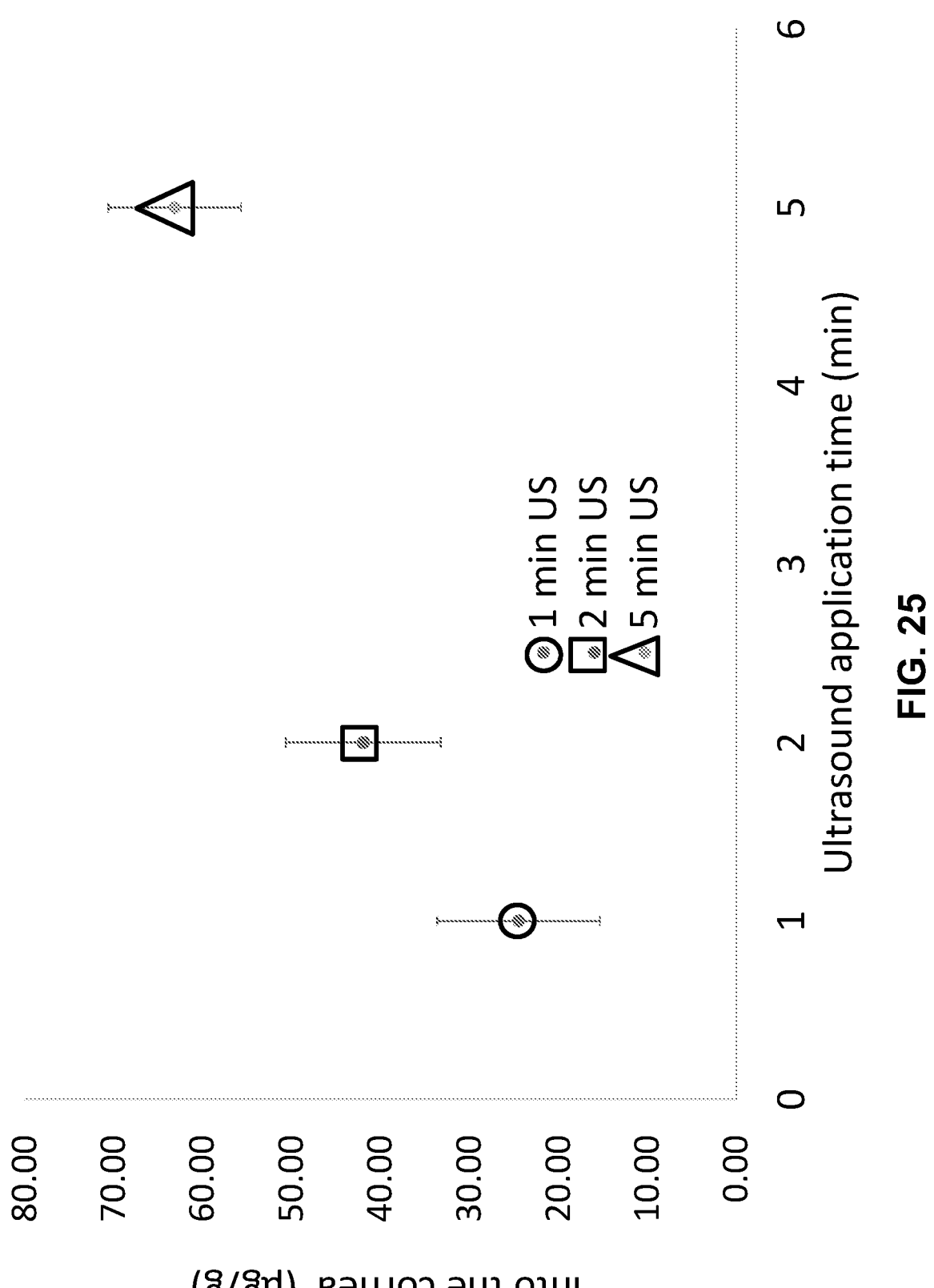
FIG. 25 shows another example of data pertaining to riboflavin delivery to a target site.

FIG. 25 shows another example of data pertaining to riboflavin delivery to a target site. This data shows the concentration of riboflavin molecules delivered into the cornea by ultrasound at indicated durations. The concentration of Riboflavin-5-Phosphate delivered into porcine corneas by ultrasound for 5 minutes or less reached the therapeutic threshold when compared with the concentration delivered via typical Dresden protocol (30 minutes instillation of riboflavin solution on the porcine cornea).

Riboflavin-5-Phosphate (R5P), 1.5 mL, 0.1% solution was applied to a porcine eyeball, epi-off. The ultrasound parameters were 40 kHz, mechanical index 0.2. The cornea was in full contact with R5P over indicated time period. The cornea was excised and weighed. Extracted supernatant with R5P was used for fluorescent measurement.

Figure 26:
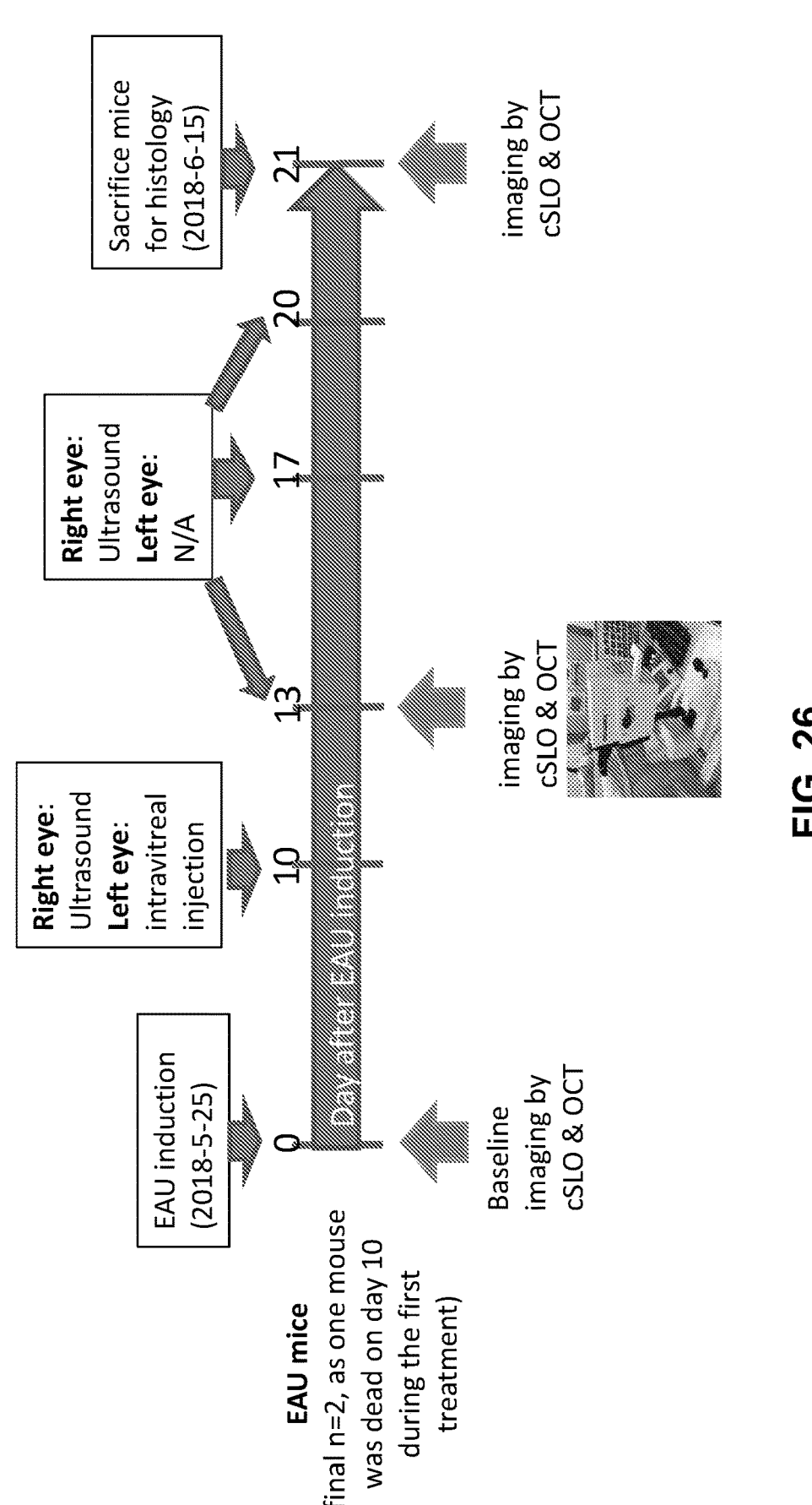
FIG. 26 shows an example of an experimental procedure implementing the systems and methods described herein.

FIG. 26 shows an example of an experimental procedure implementing the systems and methods described herein. The procedure relates to an in vivo study of delivering small molecules into mice eyes for treatment of experimental autoimmune uveitis (EAU). The small molecules used were dexamethasone, with of a molecular weight of about 376 g/mol. For a given animal subject, the drug was delivered via intravitreal injection (10 µg in 1 µL balanced salt solution), to the left eye. For the right eye, the drug (10 µg in 1 µL balanced salt solution, repeat 3 times) was delivered by 40 kHz ultrasound.

A timeline is illustrated of the experimental procedure. EAU mice were provided as described. The final n=2, as one mouse was dead on day 10 during the first treatment. The data for Mouse 1 and Mouse 2 were collected as detailed in greater detail below. On day 0, EAU induction occurred. Baseline imaging by confocal scanning laser ophthalmology (cSLO) and optical coherence tomography (OCT) occurred on day 0. On day 10, the drug was applied via ultrasound on the right eye. The drug was applied via intravitreal injection to the left eye. On day 13, imaging was conducted via cSLO and OCT. On days 13, 17, and 20, the drug was delivered to the right eye via ultrasound. On day 21, the mice were sacrificed for histology. Imaging was conducted by cSLO and OCT.

Figure 27:
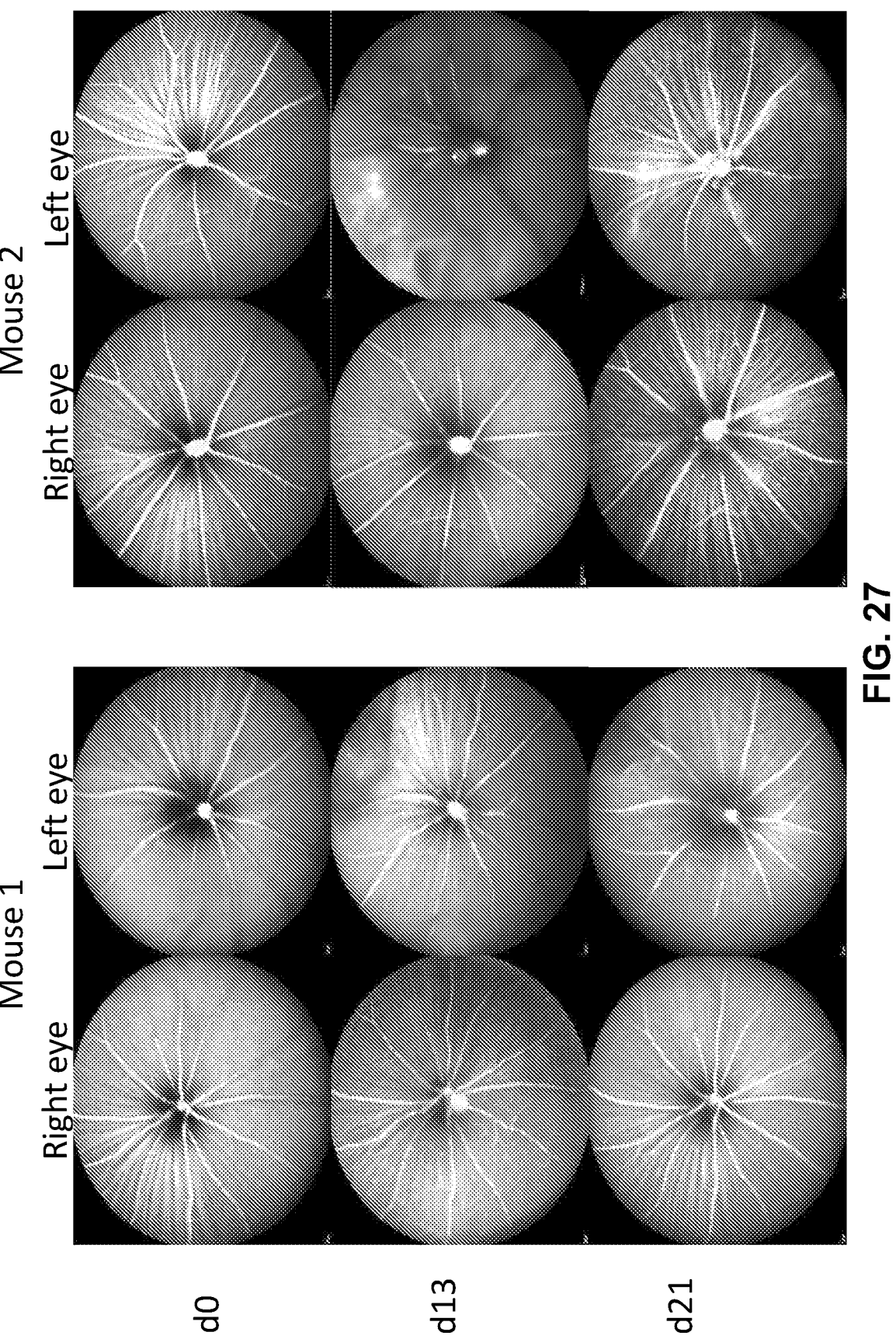
FIG. 27 shows images of effects of the systems and methods described herein as illustrated by the experimental procedure.

FIG. 27 shows images of effects of the systems and methods described herein as illustrated by the experimental procedure. Images of the right eye and the left eye of Mouse 1, and the right eye and left eye of Mouse 2 are provided. The images are fundus photos, which may be taken via fundus fluorescein angiography (FFA). The images are provided for day 0, day 13, and day 21. Mouse 1 right eye shows no injury of retina and less infiltrated cells around the optic nerve head compared to the left eye. Mouse 2 right eye shows no injury of retina and less severe vasculitis compared to the left eye. This suggests that the application of the drug via the ultrasound results in less severe vasculitis and/or infiltrated cells around the nerve head compared to intravitreal injection.

Figure 28:
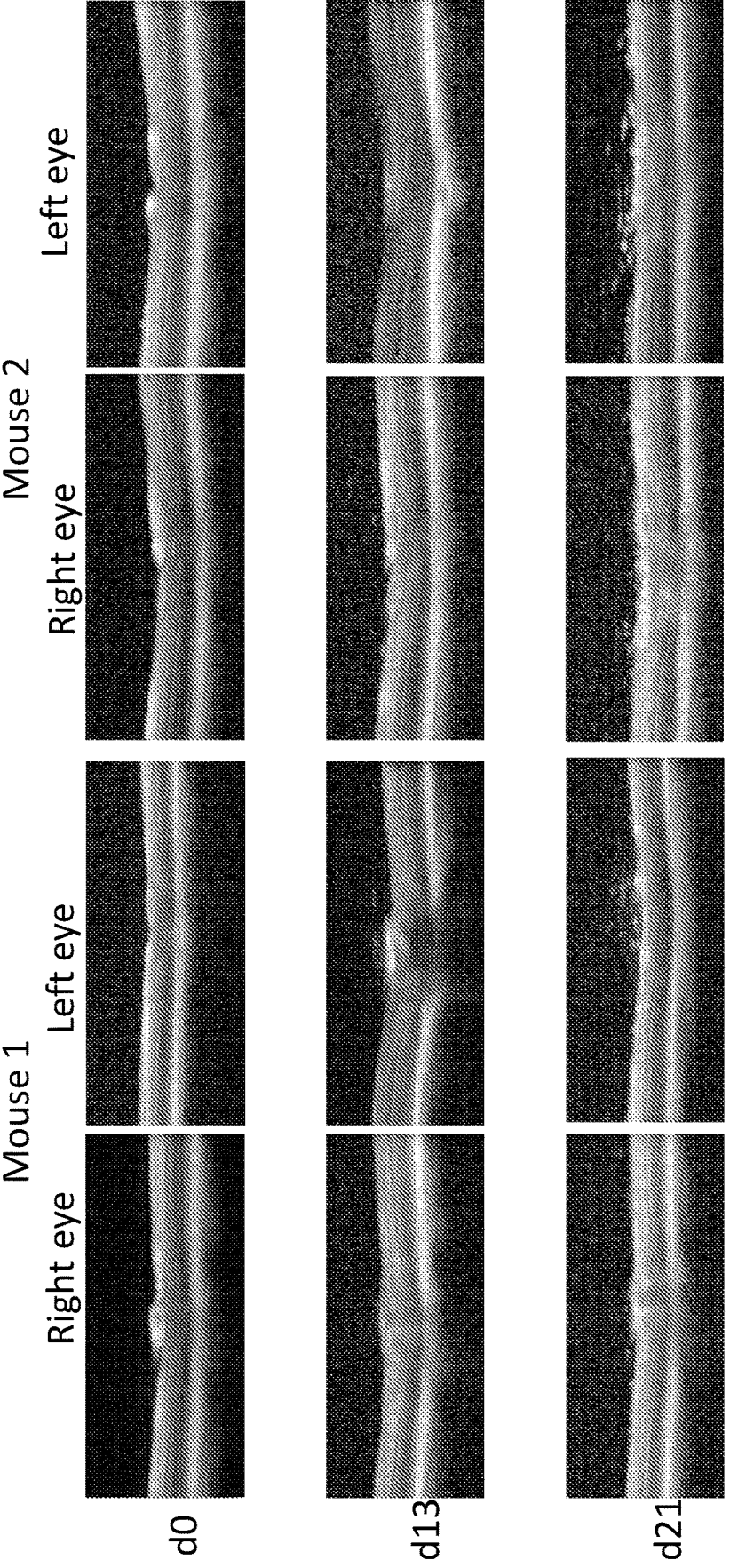
FIG. 28 shows further illustrations of the effects of the systems and methods.

FIG. 28 shows further illustrations of the effects of the systems and methods. OCT sections are provided for the right eye and left eye of Mouse 1, and the right eye and left eye of Mouse 2. The images are provided for day 0, day 13, and day 21. The right eye of Mouse 1 shows less infiltrated cells around the optic nerve head compared to the left eye. The right eye of Mouse 2 shows less infiltrated cells around the optic nerve head compared to the left eye. This suggests that the application of the drug via the ultrasound results in less infiltrated cells around the optic nerve head compared with the intravitreal injection.

Figure 29:
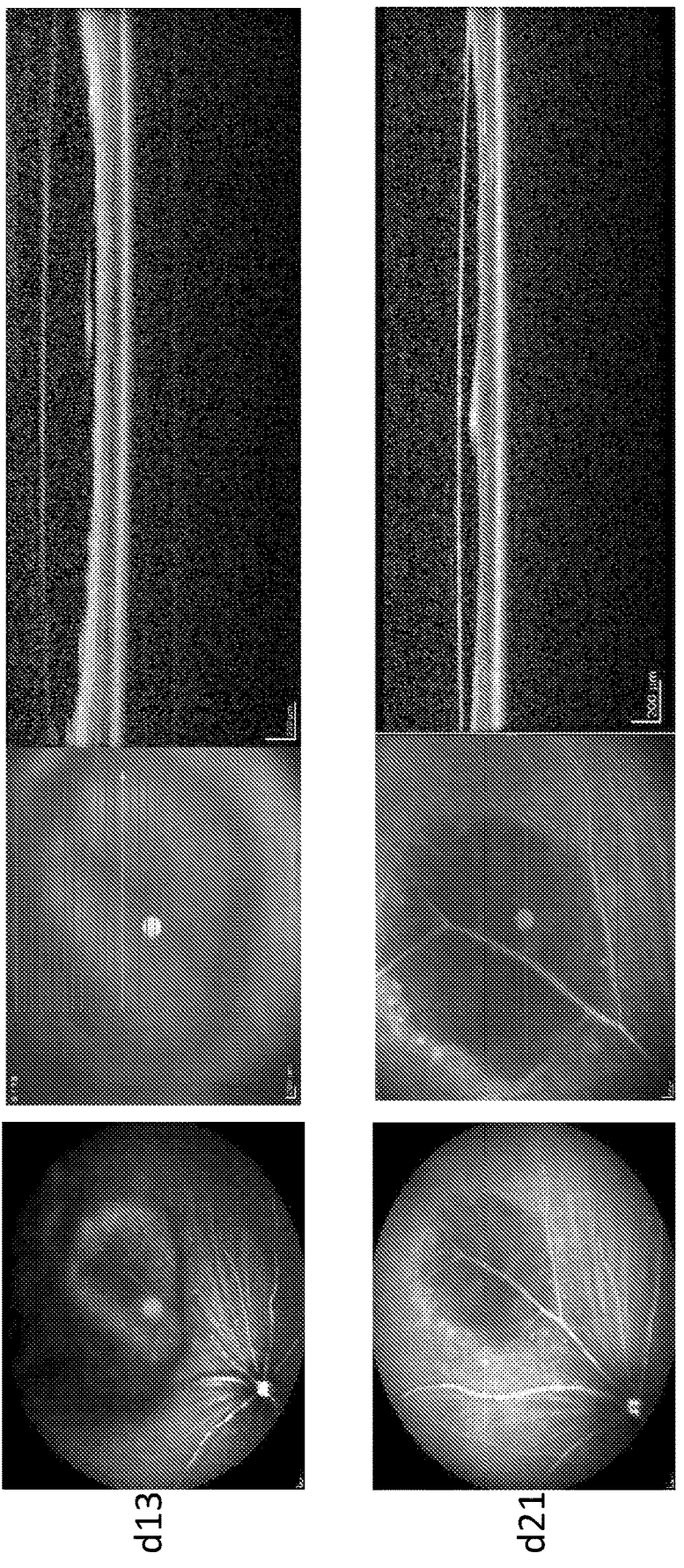
FIG. 29 shows an illustration of a first mouse left eye from the experimental procedure.

FIG. 29 shows an illustration of a first mouse left eye from the experimental procedure. The FFA photo and OCT sections are illustrated, showing that the left eye of Mouse 1 has retina injury caused by intravitreal injection. The retinal change still existed at day 21 when the animal was sacrificed.

FIG. 30 shows an illustration of a second mouse left eye from the experimental procedure. The FFA photo and OCT sections are illustrated, showing that the left eye of Mouse 2 has retina injury caused by intravitreal injection. The retinal change still existed at day 21 when the animal was sacrificed, although the reginal damage at the injection site was reduced compared to Mouse 1, possibly due to improved technique.

A drug delivery system or component thereof may be provided as a kit comprising instructions of use thereof. For instance, a kit comprising a drug delivery device may be provided with instructions of use thereof. A drug applicator may be provided together with the drug delivery device or may be provided separately. A kit comprising a drug applicator may be provided with instructions of use thereof. The kit may comprise information about drugs loaded onto the drug applicator. One or more settings for use of the drug delivery device for the particular drug and/or drug applicator may be provided in the instructions. In some embodiments, a drug delivery device may be reusable. A drug applicator may be coupled to the drug delivery device. The drug applicator may be reusable or may be disposable. Optionally, the drug applicator may be refilled or loaded with drugs. In some instances, the drug applicator may be disposable after a single use.

Throughout this application the terms "drug", "therapeutic agent", and the more general term "molecules" are considered to be interchangeable and the respective use depends on the technical context. The use of one specific wording is not meant to limit the scope of the subject-matter protection is sought for. For example, a therapeutic agent may comprise a drug and/or a drug may comprise molecules.

The term "drug", as used herein, means a pharmaceutical formulation containing at least one pharmaceutically active compound. In one embodiment of the invention the pharmaceutically active compound has a molecular weight up to 70 kDa and/or comprises antibodies, biologics conjugates, protein drug conjugates, corticosteroid drug conjugates, drug-encapsulated nanoparticles, drug-conjugated nanoparticles, protein drugs, biologics, corticosteroid drugs, nonsteroidal anti-inflammatory drugs, charged molecules, uncharged molecules, or a mixture of the above-mentioned pharmaceutically active compounds. In an alternative embodiment of the invention the pharmaceutically active compound has a molecular weight of more than 70 kDa and/or comprises antibodies, biologics conjugates, protein drug conjugates, corticosteroid drug conjugates, drug-encapsulated nanoparticles, drug-conjugated nanoparticles, protein drugs, biologics, corticosteroid drugs, nonsteroidal anti-inflammatory drugs, charged molecules, uncharged molecules, or a mixture of the above-mentioned pharmaceutically active compounds. In some instances, drugs may include any compounds or molecules that may be useful for treating a disease or condition of the eye, performing diagnostics, promoting health of the eye, or any other portion of the body. In some embodiments, examples of drugs may include but are not limited to: prostaglandin or analogs like latanoprost (Xalatan), bimatoprost (Lumigan) and travoprost (Travatan) which may increase uveoscleral outflow of aqueous humor; topical beta-adrenergic receptor antagonists such as timolol, levobunolol (Betagan), and betaxolol which may decrease aqueous humor production by the ciliary body; Alpha2-adrenergic agonists such as brimonidine (Alphagan) which may work by a dual mechanism, decreasing aqueous production and increasing uveo-scleral outflow; less-selective sympathomimetics like epinephrine and dipivefrin (Propine) which may increase outflow of aqueous humor through trabecular meshwork and possibly through uveoscleral outflow pathway; miotic agents (parasympathomimetics) like pilocarpine which work by contraction of the ciliary muscle, tightening the trabecular meshwork and allowing increased outflow of the aqueous humour; carbonic anhydrase inhibitors like dorzolamide (Trusopt), brinzolamide (Azopt), acetazolamide (Diamox) which may provide a reduction of aqueous humor production by inhibiting carbonic anhydrase in the ciliary body; betablockers; Bevacizumab (Avastin); Ranibizumab (Lucentis); Triamcinolone acetonide (Kenalog) (Triesence/Trivaris); Ganciclovir Intravitreal; Foscarnet Intravitreal; Cidofovir; Fomvirsen; Methotrexate; Vancomycin; Ceftazidime; Amikacin; Amphotericin B; Voriconazole; Dexamethasone; riboflavin; Nesvacumab or other monoclonal antibody that may target protein angiopoetin 2 (ANG2) or other proangiogenic cytokine; or Fovisa, Zimura or other aptamers which may bind with specificity and affinity to targets such as platelet-derived growth factor (PDGF).

In an embodiment the pharmaceutically active compound is useful for the treatment and/or prophylaxis of central retinal vein occlusion, branch retinal vein occlusion, central serous retinopathy, cytomegalovirus retinitis, retinoblastoma, intraocular lymphoma, ocular melanoma, giant cell arteritis, histoplasmosis, ischemic optic neuropathy, macular pucker, macular telangiectasia, uveitis, choroidal neovascularization, age-related macular degeneration, diabetic retinopathy, glaucoma, retinitis pigmentosa, macular edema, cystoid macular edema, macular degeneration, multirecurrent pterygia, ocular toxoplasmosis, proliferative vitreo-retinopathy (PVR), Stevens-Johnson syndrome, ocular cicatricial pemphigoid, endophthalmitis, an ocular degenerative condition, or a post-surgery condition which requires the delivery of a drug into an intrascleral space.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A drug applicator for a system for ultrasound-enhanced delivery of at least one drug to a target site in an intraocular space, the system comprising a signal generating unit and a controller operationally connected to an ultrasound transducer, wherein the drug applicator:
(a) comprises at least one space configured to hold the drug,
(b) is made from a low ultrasound attenuation material that provides an ultrasound attenuation of less than 10 dB/(Mhz cm), wherein the low ultrasound attenuation material is configured to minimize attention of ultrasound and facilitate transport of the ultrasound emitted from the ultrasound transducer to the drug applicator towards the target site in the intraocular space,
(c) provides less than 20% ultrasound loss coupling of the system to a sclera or cornea, and
(d) is mechanically coupled to the system and further configured to be coupled to the ultrasound transducer with ultrasound loss of less than 20%;
wherein the controller generates a signal that causes the ultrasound transducer to emit an ultrasound wave form in at least one application cycle, the application cycle comprising at least one ultrasound emitting event with a time duration TA and a waiting period with a time duration TW, and wherein when the drug comprises molecules with a size of more than 70 kDa, the controller is configured to control the time duration TW to be between 60s and 600s and the drug applicator is configured such that the molecules drug transit through the sclera during the time duration TW.

2. The applicator according to claim 1, wherein the at least one space has at least one opening at a surface directed towards a desired site of the eye, and wherein an ultrasound coupling agent is filled in a gap between the drug applicator and the desired site of the eye.

3. The applicator according to claim 1, wherein the drug applicator is configured to be exchangeable and/or designed for a single use application.

4. The applicator according to claim 1, wherein the drug receiving space is sealed at a surface designated for coupling with a desired site of the eye and the seal is configured to allow for drug permeation.

5. The applicator according to claim 1, wherein the drug receiving space is open at a surface designated for coupling with the sclera.

6. The applicator according to claim 1, wherein the drug applicator is configured to be filled and/or refilled, and wherein the drug applicator receives between 10 μL and 1.5 mL of the drug.

7. The applicator according to claim 1, wherein the drug applicator receives at least one additional substance.

8. The applicator according to claim 1, wherein the drug applicator is made from an elastic material having Young's Modulus of greater than 10 GPa.

9. The applicator according to claim 1, wherein the drug applicator is made from at least one of the following materials:

epoxy resin, polyurethane rubber, polycarbonate, nylon 6-6, polyvinyl chloride, polyester, ultra-high molecular weight polyethylene, polypropylene, teflon, polystyrene, neoprene rubber, polyvinyl alcohol, polydimethylsiloxane, silicone-containing rubber, silicon hydrogel, silicone rubber, and silicon rubber doped with at least one of the following materials: nickel, silver, palladium, tungsten, gold, platinum, silicon oxide, titanium oxide, aluminum oxide, barium sulphate, iron oxide, zirconium dioxide, cerium oxide, bismuth oxide, ytterbium oxide, lutetium oxide, hafnium oxide.

10. The applicator according to claim 1, wherein the drug applicator is configured to deliver the at least one drug to the target site during both the time duration TA and the time duration TW.

11. The applicator according to claim 10, wherein the drug applicator is configured to deliver the at least one drug to the target site based in part on a molecule size of the at least one drug.

12. A system for ultrasound-enhanced transscleral delivery of at least one drug to a target site in an intraocular space, the system comprising:

a signal generating unit, a drug applicator and a controller operationally connected to an ultrasound transducer, wherein the drug applicator:

(a) comprises at least one space configured to hold the drug, (b) is made from a low ultrasound attenuation material that provides an ultrasound attenuation of less than 10 dB/(Mhz cm), wherein the low ultrasound attenuation material is configured to minimize attention of ultrasound and facilitate transport of the ultrasound emitted from the ultrasound transducer to the drug applicator towards the target site in the intraocular space, (c) provides less than 20% ultrasound loss coupling of the system to a sclera or cornea, and (d) is mechanically coupled to the system and further configured to be coupled to the ultrasound transducer with ultrasound loss of less than 20%;

wherein the controller generates a signal that causes the ultrasound transducer to emit an ultrasound wave form in at least one application cycle, the application cycle comprising at least one ultrasound emitting event with a time duration TA and a waiting period with a time duration TW, wherein when the drug comprises molecules with a size of more than 70 kDa, the controller is configured to control the time duration TW to be between 60s and 600 s and the drug applicator is configured such that the molecules drug transit through the sclera during the time duration TW.

13. The system according to claim 12, wherein, when the drug comprises molecules with a size of 70 kDa or less, the controller is configured to control the time duration TA to be between 30s and 300 s and the drug applicator is configured such that the drug transit through the sclera during the time duration TA.

14. The system according to claim 12, wherein the controller is configured to control at least one of a plurality of parameters of the application cycle, the plurality parameters of the application cycle are selected from the following:

(a) the time duration TA of the ultrasound emitting event, (b) the time duration TW of a wait period after the ultrasound emitting event, (c) a number of application cycles, (d) an intensity of the ultrasound emitting event, (e) a central frequency of the ultrasound emitting event, (f) a mechanical index of an ultrasound emitting system, and in case of a pulsed ultrasound emitting event, (g) a repetition rate of the ultrasound emitting event, and (h) a duty cycle of the ultrasound emitting event.

15. The system according to claim 12, further comprising an information receiving unit, information sending unit, or information receiving and sending unit, wherein the information receiving unit or information sending unit is configured to receive information or send information related to the drug, respectively; and wherein the information receiving unit, information sending unit, or information receiving and sending unit is operationally connected to the signal generating unit, the controller, or the signal generating unit and the controller.

16. The system according to claim 15, wherein the controller is configured to control at least one of a plurality of parameters of the application cycle based on the information related to the drug.

17. The applicator according to claim 15, wherein the information related to the drug is stored on the drug applicator.

18. The system according to claim 12, wherein the system further comprises display and/or manual input unit configured to display and/or manually set at least one of a plurality parameters of the application cycle.

19. The system according to claim 12, wherein the system further comprises a temperature sensor configured to sense a temperature of a surface of the sclera or cornea, and wherein the controller is configured to control the ultrasound emission event such that during the time TA the temperature of the surface of the sclera or cornea does not increase by more than 1° C.

20. The system according to claim 19, wherein the system further comprises a thermocouple and/or an infrared thermometer.

* * * * *